United States Patent
Liu et al.

(10) Patent No.: US 12,291,522 B2
(45) Date of Patent: May 6, 2025

(54) GALECTIN-3 INHIBITORS

(71) Applicant: BRISTOL-MYERS SQUIBB COMPANY, Princeton, NJ (US)

(72) Inventors: Chunjian Liu, Pennington, NJ (US); Wei Wang, Princeton, NJ (US); Bruce A. Ellsworth, Princeton, NJ (US); James Aaron Balog, Lambertville, NJ (US); Alicia Regueiro-Ren, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 172 days.

(21) Appl. No.: 17/927,426

(22) PCT Filed: May 27, 2021

(86) PCT No.: PCT/US2021/034454
§ 371 (c)(1),
(2) Date: Nov. 23, 2022

(87) PCT Pub. No.: WO2021/242982
PCT Pub. Date: Dec. 2, 2021

(65) Prior Publication Data
US 2023/0303538 A1    Sep. 28, 2023

Related U.S. Application Data

(60) Provisional application No. 63/030,968, filed on May 28, 2020.

(51) Int. Cl.
*C07H 19/056* (2006.01)
*C07D 405/14* (2006.01)
*C07H 17/02* (2006.01)

(52) U.S. Cl.
CPC ......... *C07D 405/14* (2013.01); *C07H 19/056* (2013.01)

(58) Field of Classification Search
None
See application file for complete search history.

(56) References Cited

FOREIGN PATENT DOCUMENTS

WO    2019067702 A1    4/2019

OTHER PUBLICATIONS

Bricelj et al., "E3 Ligase Ligands in Successful PROTACs: An Overview of Syntheses and Linker Attachment Points", Frontiers in Chemistry, vol. 9 (2021).
Ross, A., "Exploring Novel Approaches Towards Anti-Cancer Galectin-3 Chemotherapeutics", pp. 1-186 (2020).

*Primary Examiner* — Traviss C Mcintosh, III
(74) *Attorney, Agent, or Firm* — Jing G. Sun

(57) ABSTRACT

The present disclosure relates to compounds of Formula (I), which inhibit Gal-3, and include pharmaceutically acceptable salts, compositions comprising such compounds, and methods using and making such compounds and compositions.

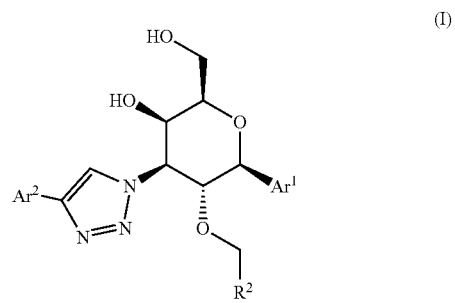

16 Claims, No Drawings

GALECTIN-3 INHIBITORS

CROSS-REFERENCE TO RELATED APPLICATIONS

This application is a 371 of International Application No. PCT/US2021/034454 filed on May 27, 2021, which claims the priority benefit of U.S. Provisional Application No. 63/030,968, filed May 28, 2020; the content of which is herein incorporated by reference in its entirety.

BACKGROUND OF THE INVENTION

Galectin-3 (Gal-3) is a β-galactoside binding lectin of about 30 KDa (Cell 76:597-598), that is involved in the regulation of inflammatory and fibrotic processes. (Immunological Reviews 230:160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involvement of Gal-3 in the development of fibrotic process in multiple organs such as lung (Am J. Respir. Crit. Care Med. 185:537-546), liver (PNAS 103: 5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, WO2014067986, WO2017080973, WO2016120403, US20140099319, WO2018209255, WO2019067702, WO2019/075045, and WO2019/241461.

The present disclosure relates to bifunctional compounds that combine a moiety that binds to Gal-3 and E3 ubiquitin ligase binding moiety and their methods of use. The bifunctional compounds are useful degraders/or inhibitors of Gal-3.

DESCRIPTION OF THE INVENTION

The present disclosure relates to compounds of the present invention, which inhibit Gal-3, and include pharmaceutically acceptable salts, compositions comprising such compounds, and methods using and making such compounds and compositions.

In a 1st aspect, the present invention provides, inter alia, a compound of Formula (I):

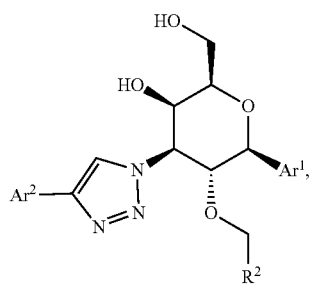

or a pharmaceutically acceptable salt thereof, wherein:
$Ar^1$ is independently

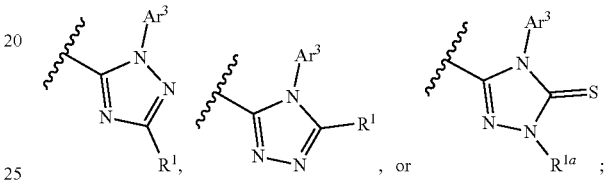

$Ar^2$ is independently phenyl or naphthyl; and wherein each ring moiety is substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy;

$Ar^3$ is independently phenyl, pyridinyl, quinolone, isoquinoline, or benzothaizolyl, wherein each ring moiety is substituted with 0 to 3 substituents selected from cyano, halogen, $C_{1-4}$ alkyl, $C_{1-4}$ haloalkyl;

$R^1$ and $R^{1a}$ are independently H or $C_{1-4}$ alkyl;

$R^2$ is independently —C(=O)NR$^3$R$^4$ or —OR$^4$;

$R^3$ is independently H, $C_{1-4}$ alkyl, or $C_{1-4}$ haloalkyl;

$R^4$ is independently -(L$^1$)$_{1-4}$-L$^2$-C(=O)NHR$^5$, -(L$^1$)$_{1-4}$-L$^2$-NHC(=O)R$^5$, (L$^1$)$_{1-4}$-NHC(=O)-L$^2$-OR$^5$,

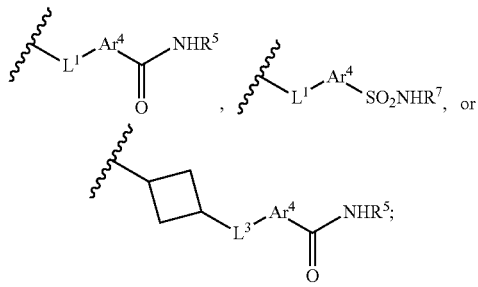

alternatively, —NR$^3$R$^4$ is independently

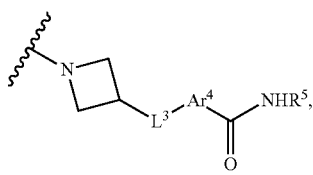

-continued

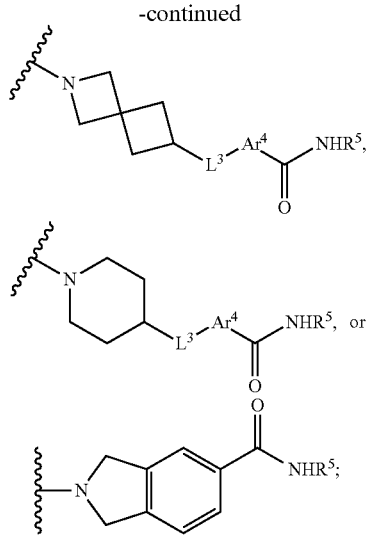

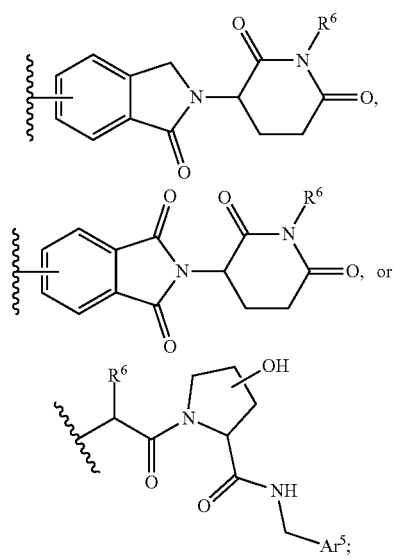

$L^1$ is independently $C_{1-3}$ alkylene or $-C_{1-3}$ alkylene-O—;
$L^2$ is independently a bond or $C_{1-3}$ alkylene;
$L^3$ is independently —O—, —CH$_2$—, —CH$_2$O—, —OCH$_2$—, or —CH$_2$OCH$_2$—;
$Ar^4$ is independently phenylene or pyridinylene; and wherein each ring moiety is substituted with 0 to 2 substituents selected from cyano, halogen, $C_{1-4}$ alkyl, $C_{1-4}$ haloalkyl, $C_{1-4}$ alkoxy, and $C_{1-4}$ haloalkoxy;
$R^5$ is independently $R^6$ is independently H or $C_{1-4}$ alkyl;
$R^7$ is independently indolyl substituted with 0 to 2 substituents selected from cyano, halogen, $C_{1-4}$ alkyl, $C_{1-4}$ haloalkyl, $C_{1-4}$ alkoxy, and $C_{1-4}$ haloalkoxy; and
$Ar^5$ is independently phenylene or pyridinylene; and wherein each ring moiety is substituted with a thiazolyl substituted with 0 to 2 substituents selected from cyano, halogen, $C_{1-4}$ alkyl, $C_{1-4}$ haloalkyl, $C_{1-4}$ alkoxy, and $C_{1-4}$ haloalkoxy.

In a 2nd aspect, within the scope of the 1st aspect, wherein:

$Ar^1$ is

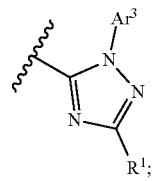

$Ar^2$ is independently phenyl substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy; and
$Ar^3$ is independently phenyl substituted with 0 to 3 substituents selected from cyano, halogen, $C_{1-4}$ alkyl, $C_{1-4}$ haloalkyl, $C_{1-4}$ alkoxy, $C_{1-4}$ haloalkoxy and $C_{3-6}$ cycloalkyl.

In a 3rd aspect, within the scope of the 2nd aspect, wherein:
$Ar^2$ is independently phenyl substituted with 1 to 4 substituents selected from F, Cl and Br;
$Ar^3$ is independently phenyl substituted with 0 to 3 substituents selected from Cl, CH$_3$, CF$_3$, and —OCF$_3$;
$R^3$ is independently H, $C_{1-3}$ alkyl, or $C_{1-3}$ haloalkyl;
$R^4$ is independently -L$^1$-L$^2$-C(=O)NHR$^5$, -(L$^1$)$_{1-3}$-L$^2$-NHC(=O)R$^5$,
-(L$^1$)$_{1-3}$-NHC(=O)-L$^2$-OR$^5$,

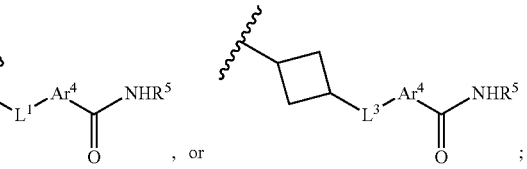

and althernatively, —NR$^3$R$^4$ is independently

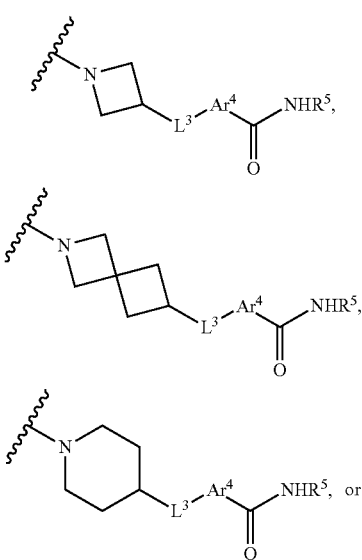

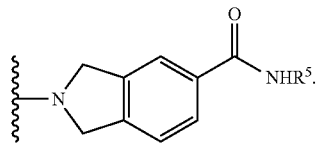

In a 4th aspect, within the scope of the 2nd or 3rd aspect, wherein:

$Ar^2$ is independently

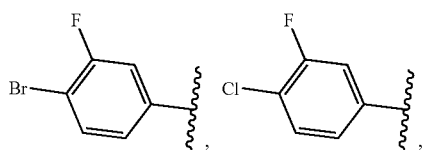

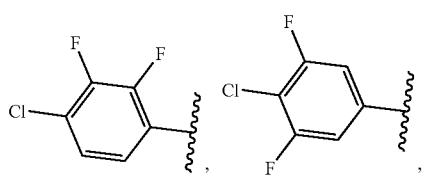

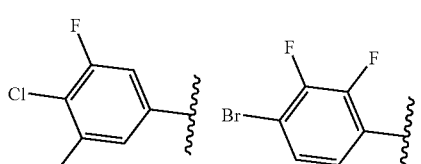

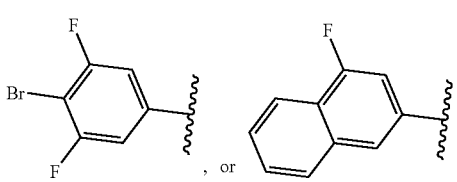

In a 5th aspect, within the scope of any of the 1st to 4th aspects, $Ar^3$ is independently

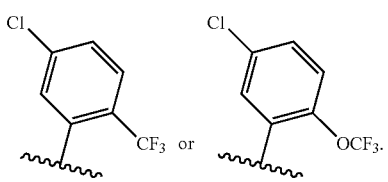 [SMILES: *c1cc(Cl)ccc1C(F)(F)F ; *c1cc(Cl)ccc1OC(F)(F)F]

In a 6th aspect, within the scope of the 1st aspect, wherein the compound is of Formula (Ia):

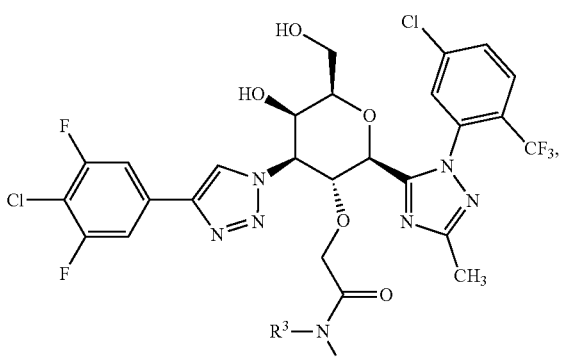

or a pharmaceutically acceptable salt thereof, wherein:

$R^3$ is independently H or —$CH_2Cl$;

$R^4$ is independently —$CH_2CH_2OCH_2C(=O)NHR^5$, —$(CH_2CH_2O)_{1-3}(CH_2)_{1-2}NHC(=O)R^5$, —$(CH_2CH_2O)_{1-3}(CH_2)_2NHC(=O)CH_2OR^5$,

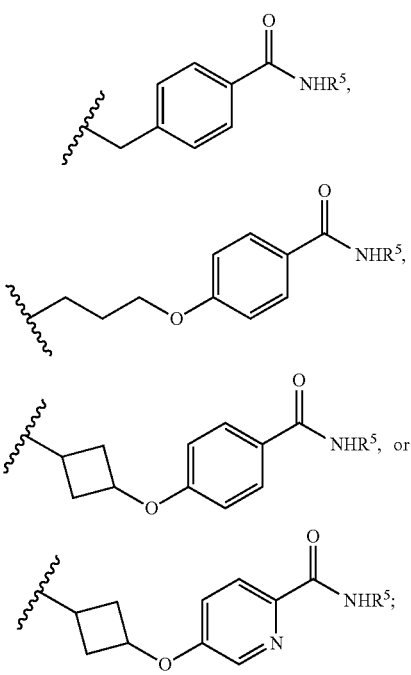

alternatively, —$NR^3R^4$ is independently

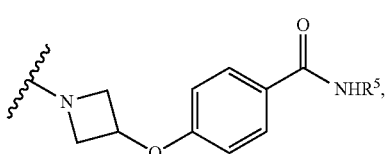

-continued
R⁵ is independently
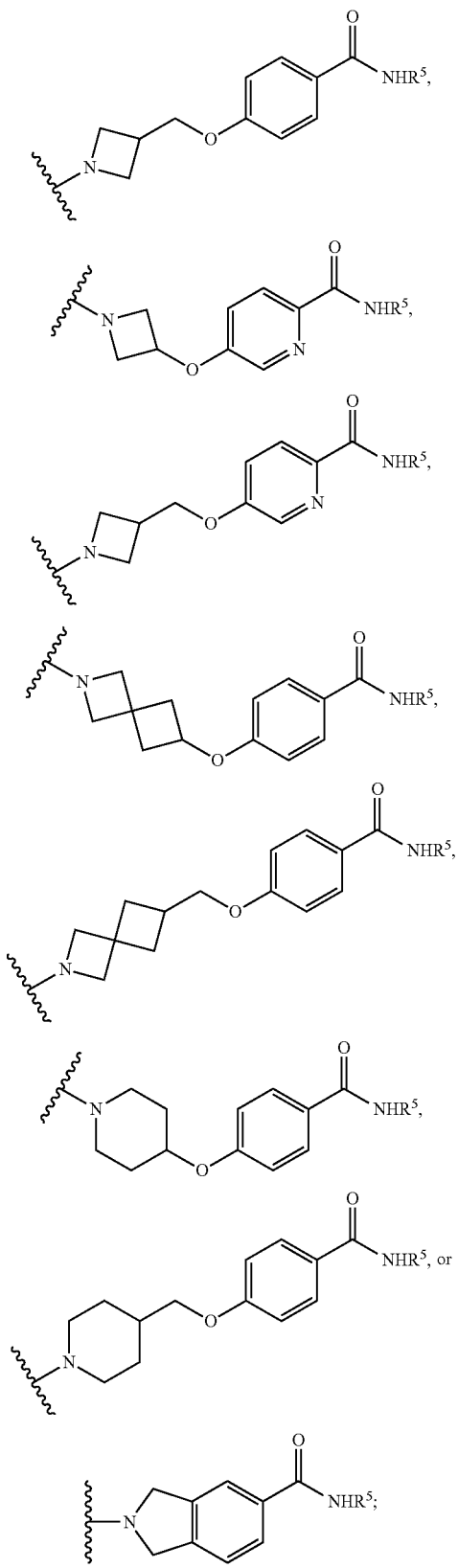
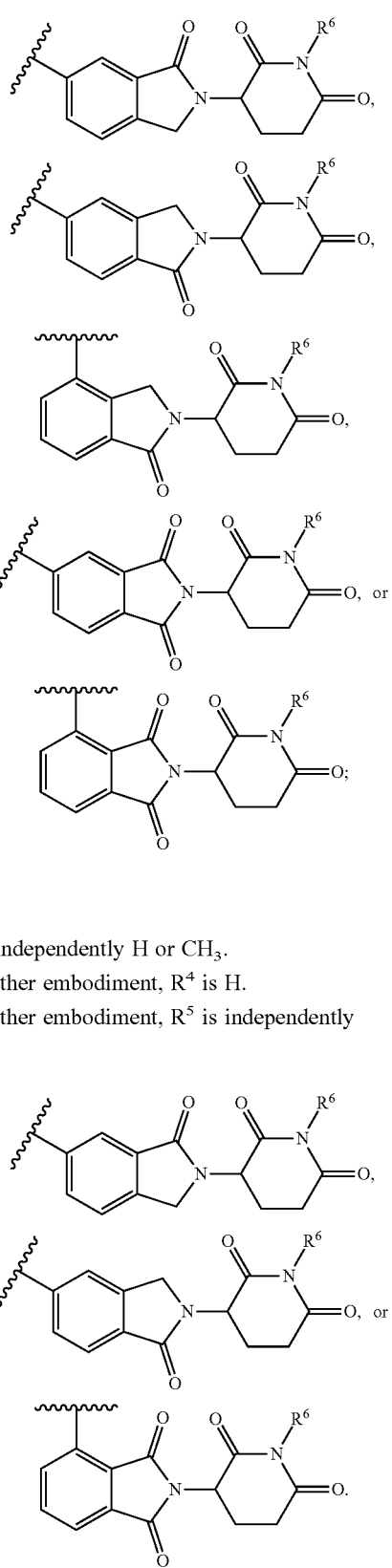
and
R⁶ is independently H or CH₃.
In another embodiment, R⁴ is H.
In another embodiment, R⁵ is independently In another embodiment, $R^5$ is independently

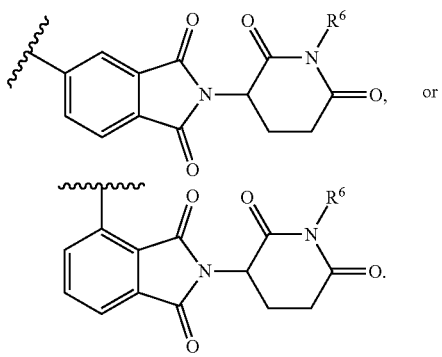

In another embodiment, $R^6$ is H.

In another aspect, the invention provides a compound selected from the exemplified examples or a pharmaceutically acceptable salt thereof.

Unless specified otherwise, these terms have the following meanings. "Alkyl" means a straight or branched alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

ASSAY BUFFER Composition: 25 mM HEPES, 100 mM NaCl, 0.005% Tween 20, 0.05% BSA prepared in sterile water (all reagents from Sigma).

Controls:
  Positive Control: 100% DMSO (1 µL)+His-tagged hGal-3 (20 µL)+B-ASF (20 µL)+Anti-His Terbium Antibody (5 µL)+Strep d2 Antibody (5 µL).
  Negative Control: 100% DMSO (1 µL)+His-tagged hGal-3 (20 µL)+Anti His Terbium Antibody (5 µL)+ Strep d2 Aantibody (5 µL).

Stocks Preparation:

| | Stock Conc. | Intermediate Conc. | Final Assay Conc. | Volume |
|---|---|---|---|---|
| His-tagged hGal-3 | 49.82 µM or can vary batch to batch | 2.525× | 15 nM | 20 µL |
| B-ASF | 25 µM | 2.525× | 15 nM | 20 µL |
| Compounds | 20 mM in 100% DMSO | Various concentration 100% DMSO | Various concentration 2% DMSO | 1 µL |
| Anti-His Tb Ab | 5.75 µM | (10×) 10 nM | 1 nM | 5 µL |
| Strep d2 | 16.67 µM | (10×) 200 nM | 20 nM | 5 µL |
| Total Assay volume | | | | 51 µL |

PROTOCOL: The Gal-3 assays were performed in 384 white Opti plates in three replicates at room temperature with gentle shaking at 250-300 rpmFrom the original stocks, 2.525× working stock concentrations of His-tagged recombinant human Gal-3 (hGal-3) and that of B-ASF were prepared. From the working stock, 20 µL of hGal-3 (15 nM) and 20 µL B-ASF (15 nM) were added to the plates. In Negative Control, only hGal-3 was added. A concentration range of 50× working stocks were prepared for the compounds in 100% DMSO. Aliquots of 1uL of the compounds were added to the wells and pre-incubated with 20 µL hGal-3 per well for 30 minutes Then 20 µL B-ASF were-added and incubated for another 1 hour. To detect the signal, 5 µL (final conc. of 1.0 nM) terbium labelled Anti-His antibody was added and incubated for 30 min followed by adding 5 µL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in μM).

CRBN BRET Target Engagement (hCRBN $IC_{50}$ (μM))

NanoLuc-CRBN fusion construct was transfected in HEK-293 cells using FuGENE HD (Promega) according to the manufacturer's protocol. In brief, Nluc-CRBN was diluted into Transfection Carrier DNA (Promega) 1:10 (mass/mass), to which FuGENE HD was 1:3 (μg DNA:μL FuGENE HD). One part (vol) of DNA:FuGENE HD complexes were combined with 20 parts (vol) of HEK-293 cells suspended at a density of 2×105. Cells were incubated for ~20 hr at 37° C./5% CO2. Following transfection, cells were washed and resuspended at 200,000 cells/mL in OptiMEM without phenol red (Gibco).

For BRET measurements, cells were seeded in a 384-well nonbinding surface plate (Corning) plate for a final count of 10,000 cells/well. Compounds were dissolved at 10 mM in dimethylsulfoxide (DMSO) and evaluated at eleven concentrations using a high concentration of 20-50 M. CRBN Probe was used for equilibrium measurements, employing a final concentration of approximately $EC_{50-80}$. For live-cell measurements, 20 nM of CRBN Probe was added. For the live-cell assay conditions, the plates were incubated for 2 hours at 37° C./5% CO2. NanoBRET NanoGlo Substrate and Extracellular Nanoluc Inhibitor (Promega) were added according to manufacturer's guidelines. For lytic cell measurements, digitonin was added to the cells to a final concentration of 50 μg/mL and 20 nM of CRBN Probe was added. To measure NanoBRET in permeabilized cells, extracellular Nluc inhibitor was omitted during the detection step. For all BRET experiments, the Envision 2015 (Perkin Elmer) equipped with a BRET2 Enh mirror, BRET 647 nM/75 nM Bandwidth and BC703 460 nM/80 nM Bandwidth filters was used for readouts. Each read was integrated for 0.5 s.

To determine compound potency ($IC_{50}$), BRET ratios for each dilution series was first normalized to a % Inhibition value via Equation 1, where "S" represents Sample BRET, "B" represents Background BRET, and "T" represents Total BRET. In this equation, the background control (B) consists of NanoLuc-CRBN expressing cells and no CRBN Probe. The total BRET Ratio (T) consists of NanoLuc-CRBN expressing cells, CRBN Probe, and an amount of DMSO at a concentration equivalent to that added when testing compounds.

$$\% \text{ Inhibition} = 100 \times \left(1 - \frac{S-B}{T-B}\right) \quad \text{(Equation 1)}$$

Following normalization, the percent inhibition values are plotted as a function of compound concentration and fit to Equation 2.

$$Y = \text{Bottom} + \frac{\text{Top} - \text{Bottom}}{1 + \frac{x^{HillSlope}}{IC_{50}^{HillSlope}}} \quad \text{(Equation 2)}$$

ELISA Gal3 Degradation Assay in THP-1 Cells

THP-1 cells (ATCC, Cat #TIB-202), a human monocyte cell line derived from leukemia were plated at 2E6 cells/mL in 200 uL/well of RPMI 1640 (ThermoFisher, Cat #11835) in 96-well plates. Cells were treated with DMSO as a control and various concentrations of compounds for 48 hours. After the treatment, the culture media were collected. The PBS washed cell pellets were lysed in Lysis Buffer (Cell Signaling, Cat #9803) supplemented with 1XProtease Inhibitor Cocktail (Cell Signaling, Cat #5872). Gal3 levels in culture media and cell lysates were quantified by ELISA assays (Human Galectin-3 DuoSet ELISA kit, R&D Systems, Cat #DY1154) according to manufacturer's instructions. The cell culture media were also used for the assessment of cellular toxicity (LDH Assay kit, R&D Systems, DY994). The IC50 (degradation concentration at 50%) values were calculated based on the cellular Gal3 protein levels using DMSO as the control.

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder) comprising administering to a compound of the present invention to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile:water with 0.1% TFA;

Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in the experimental procedures.

Methods of Preparation

Intermediate 1. 2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetic acid mmol) in THF (4 mL) was added over 1 min. The mixture was stirred at 0° C. for 50 min, and then quenched with EtOH (2 mL). The mixture was diluted with ethyl acetate (200 mL), washed with water (2×40 mL) and brine (40 mL), and dried over anhydrous MgSO$_4$. Removal of the solvent under vacuum gave a mixture (0.881 g) of ethyl 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetate and 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid in a ratio of 2:1. To a solution

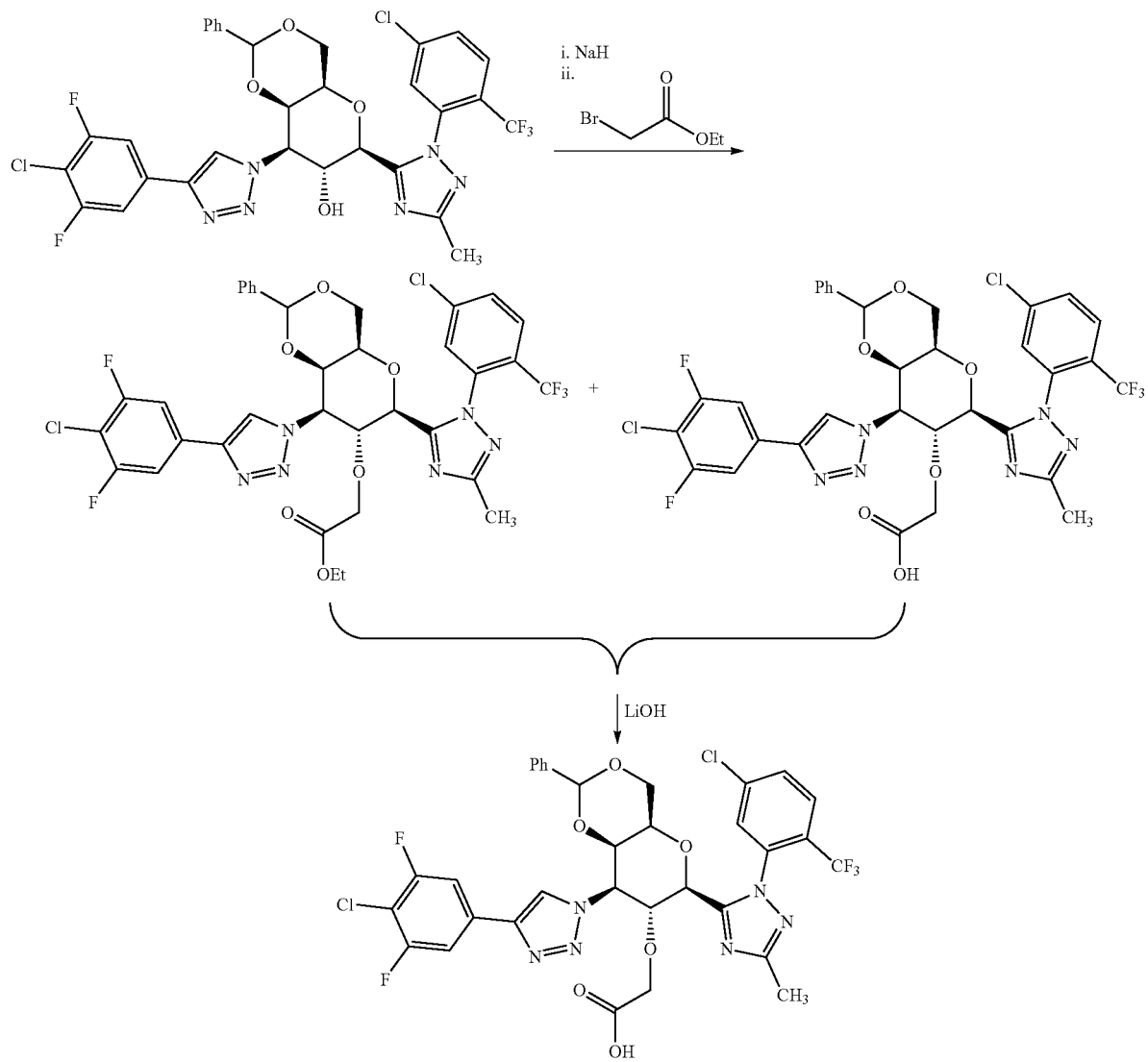

To a solution of (4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (WO 2019067702) (0.80 g, 1.128 mmol) in THF (22 mL) at 0° C. was added sodium hydride (60% oil dispersion) (0.090 g, 2.255 mmol) in one portion. The mixture was stirred at 0° C. for 15 min before ethyl 2-bromoacetate (0.150 mL, 1.353 of this mixture (0.881 g) in THF (35 mL) at rt was added lithium hydroxide (0.106 g, 4.43 mmol) in water (7 mL) over 1 min. The mixture was stirred at rt for 1.5 h and then concentrated under vacuum to a volume of approximately 7 mL. The residue was diluted with water (15 mL) and acidified with 1 N HCl solution to pH 5-6. The insoluble product, 2-(((4aR,6S,7R,8R,8aR)-6-(1-(5-chloro-2-(trifluoromethyl)phenyl)-3-methyl-1H-1,2,4-triazol-5-yl)-8-(4-(4- chloro-3,5-difluorophenyl)-1H-1,2,3-triazol-1-yl)-2-phenylhexahydropyrano[3,2-d][1,3]dioxin-7-yl)oxy)acetic acid (0.807 g, 1.051 mmol, 93% yield), was collected as a white solid by suction filtration and dried at 50° C. under vacuum. LCMS (M+H)$^+$=766.9. $^1$H NMR (500 MHZ, DMSO-d$_6$) δ 12.76-12.41 (m, 1H), 9.28 (s, 1H), 8.19-8.08 (m, 1H), 8.07 (d, J=8.5 Hz, 1H), 7.98 (br d, J=8.3 Hz, 1H), 7.83 (d, J=8.3 Hz, 2H), 7.44-7.32 (m, 5H), 5.55 (s, 1H), 5.48 (dd, J=10.6, 3.4 Hz, 1H), 4.89 (br t, J=9.6 Hz, 1H), 4.65 (d, J=9.1 Hz, 1H), 4.44 (d, J=3.3 Hz, 1H), 4.08 (br d, J=11.6 Hz, 1H), 3.95 (br d, J=12.1 Hz, 2H), 3.83 (s, 1H), 3.64 (br d, J=11.6 Hz, 1H), 2.34 (s, 3H).

Intermediate 2. 3-(5-Amino-1-oxoisoindolin-2-yl) piperidine-2,6-dione

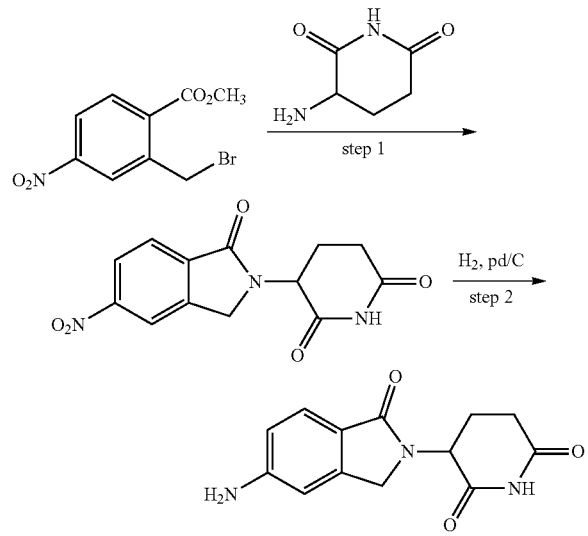

Step 1. 3-(5-Nitro-1-oxoisoindolin-2-yl) piperidine-2,6-dione

A mixture of methyl 2-(bromomethyl)-4-nitrobenzoate (1.00 g, 3.65 mmol), 3-aminopiperidine-2,6-dione, HCl (0.721 g, 4.38 mmol), and triethylamine (0.712 mL, 5.11 mmol) in methanol (15 mL) was stirred at rt for 24 h and then heated at 70° C. for 8 h. The mixture was concentrated under vacuum to dryness. To the residue was added water (50 mL) and the heterogeneous mixture was stirred at rt for 10 min. The insoluble material was collected by suction filtration. The filter cake was suspended in diethyl ether (80 mL) and stirred at rt for 1 h. The insoluble material was collected by suction filtration and dried under vacuum at 50° C. to give the desired product, 3-(5-nitro-1-oxoisoindolin-2-yl) piperidine-2,6-dione (0.634 g, 2.192 mmol, 60.1% yield), as a tan solid. LCMS (M+H)$^+$=290.1.

Step 2. 3-(5-Amino-1-oxoisoindolin-2-yl) piperidine-2,6-dione

A mixture of 3-(5-nitro-1-oxoisoindolin-2-yl) piperidine-2,6-dione (100 mg, 0.346 mmol) and 10% Pd/C (36.8 mg, 0.035 mmol) in methanol (10 mL) and tetrahydrofuran (3 mL) was stirred under H$_2$, provided with a H$_2$ balloon, at rt for 1.5 h. The solid phase was removed by suction filtration, and the filtrate was concentrated under vacuum to dryness. The residue was dried under vacuum at 50° C. to provided the desired product, 3-(5-amino-1-oxoisoindolin-2-yl) piperidine-2,6-dione (90 mg, 0.347 mmol, 100% yield), as a beige solid. LCMS (M+H)$^+$=260.1.

Intermediate 3. 3-(5-Amino-1-oxoisoindolin-2-yl)-1-methylpiperidine-2,6-dione

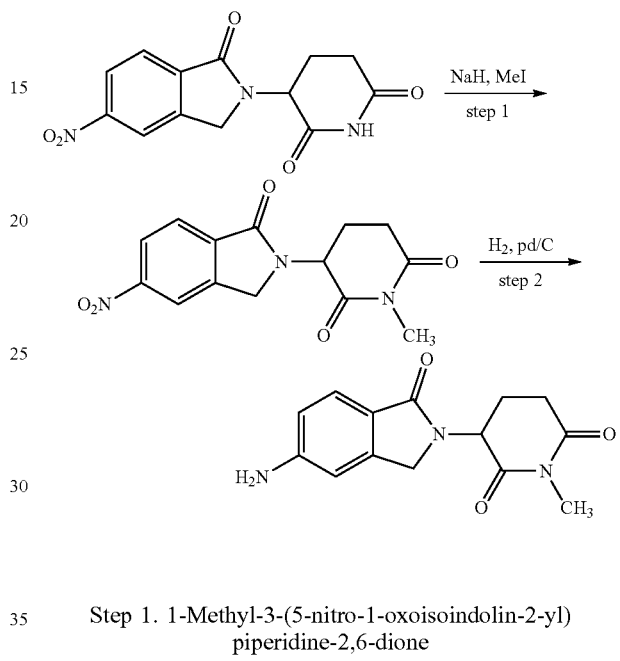

Step 1. 1-Methyl-3-(5-nitro-1-oxoisoindolin-2-yl) piperidine-2,6-dione

To a solution of 3-(5-nitro-1-oxoisoindolin-2-yl) piperidine-2,6-dione (315 mg, 1.089 mmol) in DMF (5 mL) at 0° C. was added sodium hydride (60% dispersion) (87 mg, 2.178 mmol) in one portion. The mixture was stirred at 0° C. for 30 min before iodomethane (0.136 mL, 2.178 mmol) was added. The mixture was stirred at rt for 2 h before the reaction was quenched with ice water (0.5 mL). The resulting mixture was diluted with ethyl acetate (60 mL), washed with water (2×15 mL) and brine (15 mL), and dried over anhydrous MgSO$_4$. The desired product, 1-methyl-3-(5-nitro-1-oxoisoindolin-2-yl) piperidine-2,6-dione (129 mg, 0.425 mmol, 39.1% yield), was isolated as a white solid by ISCO chromatography (24 g silica gel, solid loading, 10-60% ethyl acetate/hexane). LCMS (M+H)$^+$=304.3.

Step 2. 3-(5-Amino-1-oxoisoindolin-2-yl)-1-methylpiperidine-2,6-dione

A mixture of 1-methyl-3-(5-nitro-1-oxoisoindolin-2-yl) piperidine-2,6-dione (129 mg, 0.425 mmol) and 10% Pd/C (45.3 mg, 0.043 mmol) in methanol (10 mL) and tetrahydrofuran (3 mL) was stirred under H$_2$, provided with a H$_2$ balloon, at rt for 1.5 h. The solid phase was removed by suction filtration, and the filtrate was concentrated under vacuum to dryness. The residue was dried at 50° C. under vacuum to provided the desired product, 3-(5-amino-1-oxoisoindolin-2-yl)-1-methylpiperidine-2,6-dione (105 mg, 0.384 mmol, 90% yield), as a beige solid. LCMS (M+H)$^+$=274.3.

Intermediate 4. 3-(6-Amino-1-oxoisoindolin-2-yl)piperidine-2,6-dione

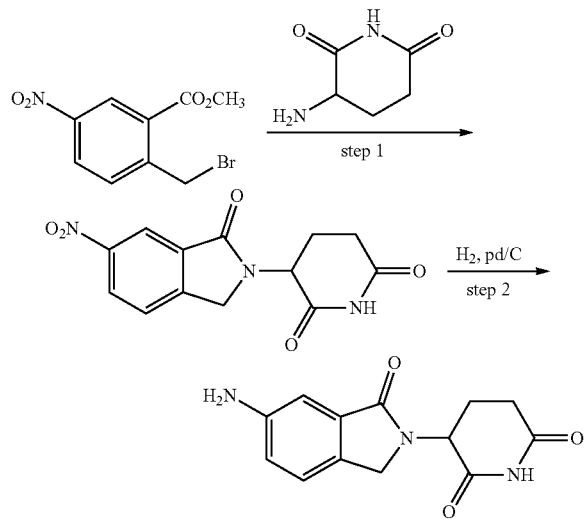

Step 1. 3-(6-Nitro-1-oxoisoindolin-2-yl)piperidine-2,6-dione

A mixture of methyl 2-(bromomethyl)-5-nitrobenzoate (1.00 g, 3.65 mmol), 3-aminopiperidine-2,6-dione, HCl (0.721 g, 4.38 mmol), and triethylamine (0.712 mL, 5.11 mmol) in methanol (15 mL) was stirred at 75° C. for 7.5 h. The mixture was concentrated under vacuum to dryness. To the residue was added water (80 mL) and the heterogeneous mixture was stirred at rt for 10 min. The insoluble material was collected by suction filtration. The filter cake was suspended in diethyl ether (100 mL) and stirred at rt for 1 h. The insoluble material was collected by suction filtration and dried under vacuum at 50° C. to give the desired product, 3-(6-nitro-1-oxoisoindolin-2-yl) piperidine-2,6-dione (0.548 g, 1.895 mmol, 51.9% yield), as a tan solid. LCMS (M+H)$^+$=289.9.

Step 2. 3-(6-Amino-1-oxoisoindolin-2-yl)piperidine-2,6-dione

A mixture of 3-(6-nitro-1-oxoisoindolin-2-yl) piperidine-2,6-dione (548 mg, 1.895 mmol) and 10% Pd/C (202 mg, 0.189 mmol) in methanol (45 mL) and tetrahydrofuran (12.5 mL) was stirred under H$_2$, provided with a H$_2$ balloon, at rt for 1.5 h. The catalyst was removed by suction filtration, and the filtrate was concentrated under vacuum to dryness. The residue was dried at 50° C. under vacuum to provide the desired product, 3-(6-amino-1-oxoisoindolin-2-yl) piperidine-2,6-dione (491 mg, 1.894 mmol, 100% yield), as a beige solid. LCMS (M+H)$^+$=259.9.

Example 1. 2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(2-(2-((2-(2,6-dioxopiperidin-3-yl)-1-oxoisoindolin-5-yl)amino)-2-oxoethoxy)ethyl)acetamide

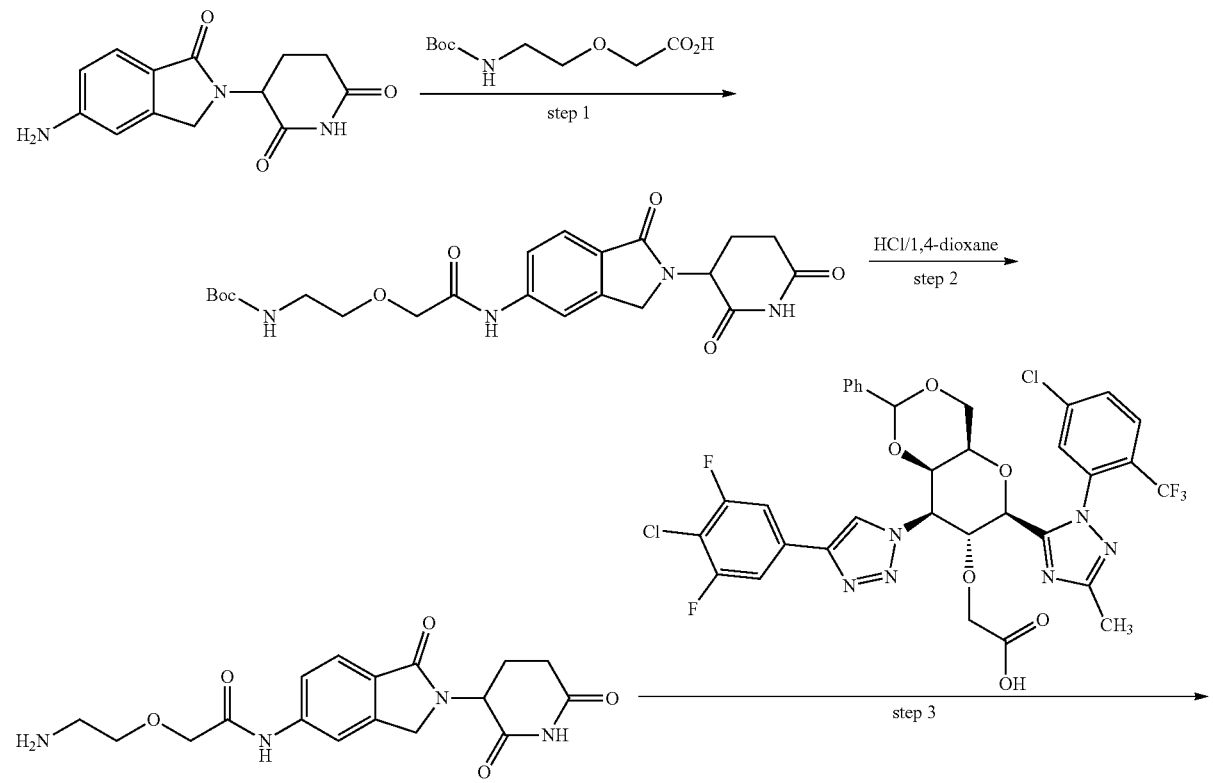

-continued

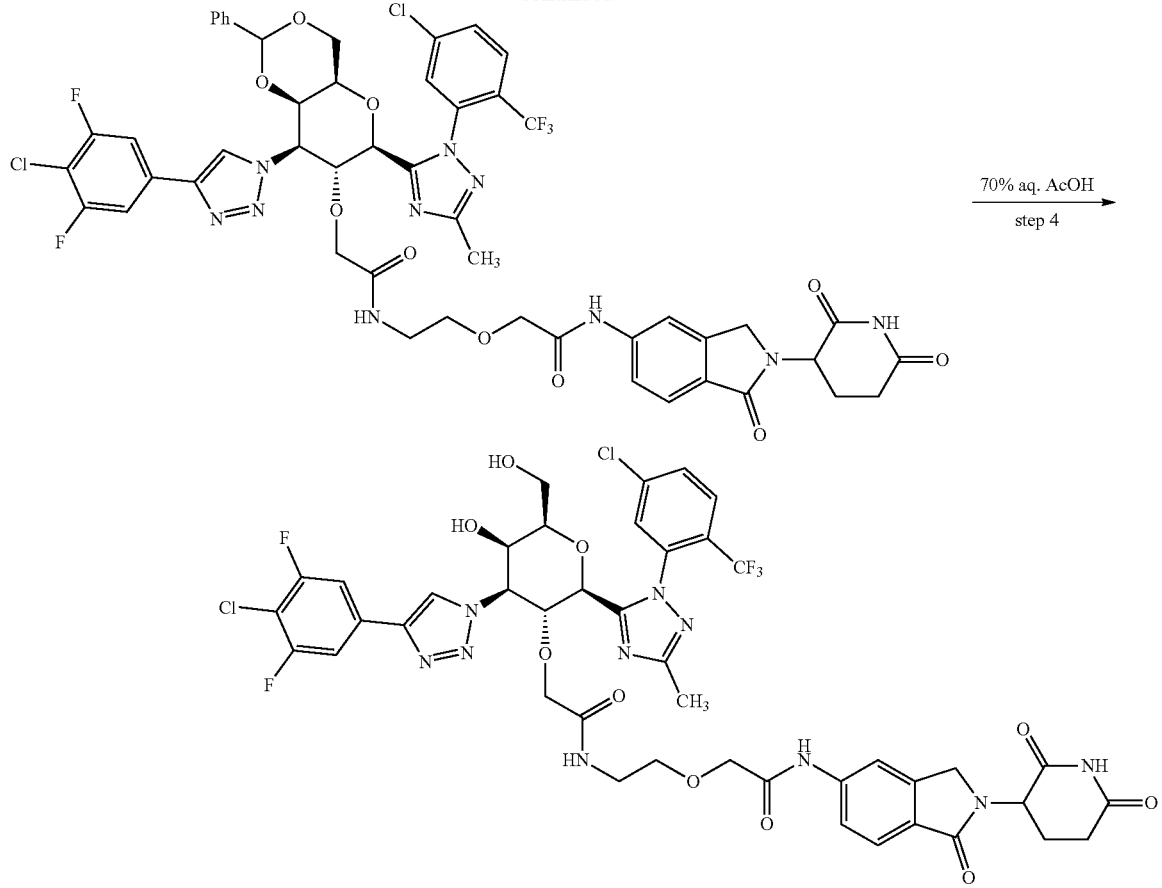

Example 1

Step 1. tert-Butyl (2-(2-((2-(2,6-dioxopiperidin-3-yl)-1-oxoisoindolin-5-yl)amino)-2-oxoethoxy)ethyl) carbamate A mixture of 2-(2-((tert-butoxycarbonyl)amino)ethoxy) acetic acid (1.319 g, 6.02 mmol), 3-(5-amino-1-oxoisoindolin-2-yl) piperidine-2,6-dione (1.20 g, 4.63 mmol), N,N-diisopropylethylamine (2.021 mL, 11.57 mmol), and 1-propanephosphonic anhydride (2.209 g, 6.94 mmol) in DMF (20 mL) was was stirred at 100° C. for 8 h. The volatiles were removed under vacuum. The residue was taken into water and extracted with dichloromethane (2×50 mL). The combined extract was dried over anhydrous $Na_2SO_4$. The desired product, tert-butyl (2-(2-((2-(2,6-dioxopiperidin-3-yl)-1-oxoisoindolin-5-yl)amino)-2-oxoethoxy)ethyl)carbamate (1.289 g, 59%), was isolated as an off-white solid by ISCO chromatography using silica gel column and 0-5% methanol/chloroform as an eluent. LCMS $(M+H)^+=461.3$.

Step 2. 2-(2-Aminoethoxy)-N-(2-(2,6-dioxopiperidin-3-yl)-1-oxoisoindolin-5-yl)acetamide To a solution of tert-butyl (2-(2-((2-(2,6-dioxopiperidin-3-yl)-1-oxoisoindolin-5-yl)amino)-2-oxoethoxy)ethyl)carbamate (55 mg, 0.119 mmol) in dichloromethane (1.5 mL) at rt was added 4 N hydrogen chloride in 1,4-dioxane (1.5 mL, 6.00 mmol) in one portion. The mixture was stirred at rt for 1 h. Removal of the volatiles under vacuum provided the desired product, 2-(2-aminoethoxy)-N-(2-(2,6-dioxopiperidin-3-yl)-1-oxoisoindolin-5-yl)acetamide, HCl (48 mg, 0.121 mmol, 101% yield), as a white solid. LCMS $(M+H)^+=361.3$.

Step 3. 2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(2-(2-((2-(2,6-dioxopiperidin-3-yl)-1-oxoisoindolin-5-yl)amino)-2-oxoethoxy)ethyl) acetamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (68 mg, 0.089 mmol), 2-(2-aminoethoxy)-N-(2-(2,6-dioxopiperidin-3-yl)-1-oxoisoindolin-5-yl)acetamide, HCl (47.5 mg, 0.120 mmol), (benzotriazol-1-yloxy)tris(dimethylamino) phosphonium hexafluorophosphate (BOP) (52.9 mg, 0.120 mmol), and N,N-diisopropylethylamine (0.062 mL, 0.354 mmol) in DMF (2 mL) was stirred at rt for 3 h. The mixture was diluted with ethyl acetate (60 mL), washed with water (15 mL), 5% hydrochloric acid (15 mL), and brine (15 mL). The organic solution was dried over anhydrous $MgSO_4$ and concentrated under vacuum to dryness to provide a crude product, 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(2-(2-((2-(2,6-dioxopiperidin-3-yl)-1-oxoisoindolin-5-yl)amino)-2-oxoethoxy)ethyl)acetamide (105 mg, 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(2-(2-((2-(2,6-dioxopiperidin-3-yl)-1-oxoisoindolin-5-yl)amino)-2-oxoethoxy)ethyl)acetamide (105 mg, 0.095 mmol, 107% yield), as a beige solid. LCMS (M+H)$^+$=1109.6.

Step 4. 2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(2-(2-((2-(2,6-dioxopiperidin-3-yl)-1-oxoisoindolin-5-yl)amino)-2-oxoethoxy)ethyl)acetamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-(2-(2-((2-(2,6-dioxopiperidin-3-yl)-1-oxoisoindolin-5-yl)amino)-2-oxoethoxy)ethyl)acetamide (105 mg, 0.089 mmol) and 70% acetic acid (4 mL) was heated at 70° C. for 10 h. upon cooling to rt, the mixture was diluted with methanol and injected to preparative HPLC (Column: Sunfire C18 OBD 5 u 30×100 mm. Solvent A: 90% H$_2$O-10% methanol-0.1% TFA; Solvent B: 10% methanol-90% H$_2$O 0.1% TFA. Starting % B: 25; Final % B: 100. Gradient Time: 15 Min). The correct fractions were combined, concentrated under vacuum, basified with saturated NaHCO$_3$ solution to pH 8, and extracted with dichloromethane (4×30 mL). The combined extract was dried over anhydrous Na$_2$SO$_4$. Removal of the solvent under vacuum provided the desired product, 2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-(2-(2-((2-(2,6-dioxopiperidin-3-yl)-1-oxoisoindolin-5-yl)amino)-2-oxoethoxy)ethyl)acetamide (51 mg, 0.049 mmol, 55.0% yield), as a white solid. LCMS (M+H)$^+$=1021.8. $^1$H NMR (500 MHZ, METHANOL-d$_4$) δ 8.81 (d, J=1.4 Hz, 1H), 7.99 (dd, J=16.9, 1.0 Hz, 1H), 7.93 (dd, J=11.1, 8.4 Hz, 1H), 7.88-7.80 (m, 2H), 7.72 (dd, J=8.3, 1.7 Hz, 1H), 7.65-7.56 (m, 3H), 5.17 (dd, J=13.3, 5.1 Hz, 1H), 5.14-5.09 (m, 1H), 5.02-4.94 (m, 1H), 4.55-4.44 (m, 3H), 4.11 (dd, J=6.6, 2.8 Hz, 1H), 4.08 (dd, J=2.5, 1.4 Hz, 2H), 3.99 (d, J=15.1 Hz, 1H), 3.71-3.62 (m, 4H), 3.59-3.50 (m, 2H), 3.41-3.35 (m, 1H), 3.30-3.23 (m, 1H), 2.98-2.89 (m, 1H), 2.85-2.78 (m, 1H), 2.53 (qd, J=13.2, 4.7 Hz, 1H), 2.45 (d, J=1.1 Hz, 3H), 2.21 (dtt, J=12.7, 5.2, 2.4 Hz, 1H). hGal-3 IC$_{50}$=0.082 µM; hCRBN IC$_{50}$=0.78 µM.

Example 2. 4-((2-(((2S,3R,4S,5R,6R)-2-(1-(5-Chloro-2-(trifluoromethyl)phenyl)-3-methyl-1H-1,2,4-triazol-5-yl)-4-(4-chloro-3,5-difluorophenyl)-1H-1,2,3-triazol-1-yl)-5-hydroxy-6-(hydroxymethyl)tetrahydro-2H-pyran-3-yl)oxy)acetamido)methyl)-N-(2-(2,6-dioxopiperidin-3-yl)-1-oxoisoindolin-5-yl)benzamide

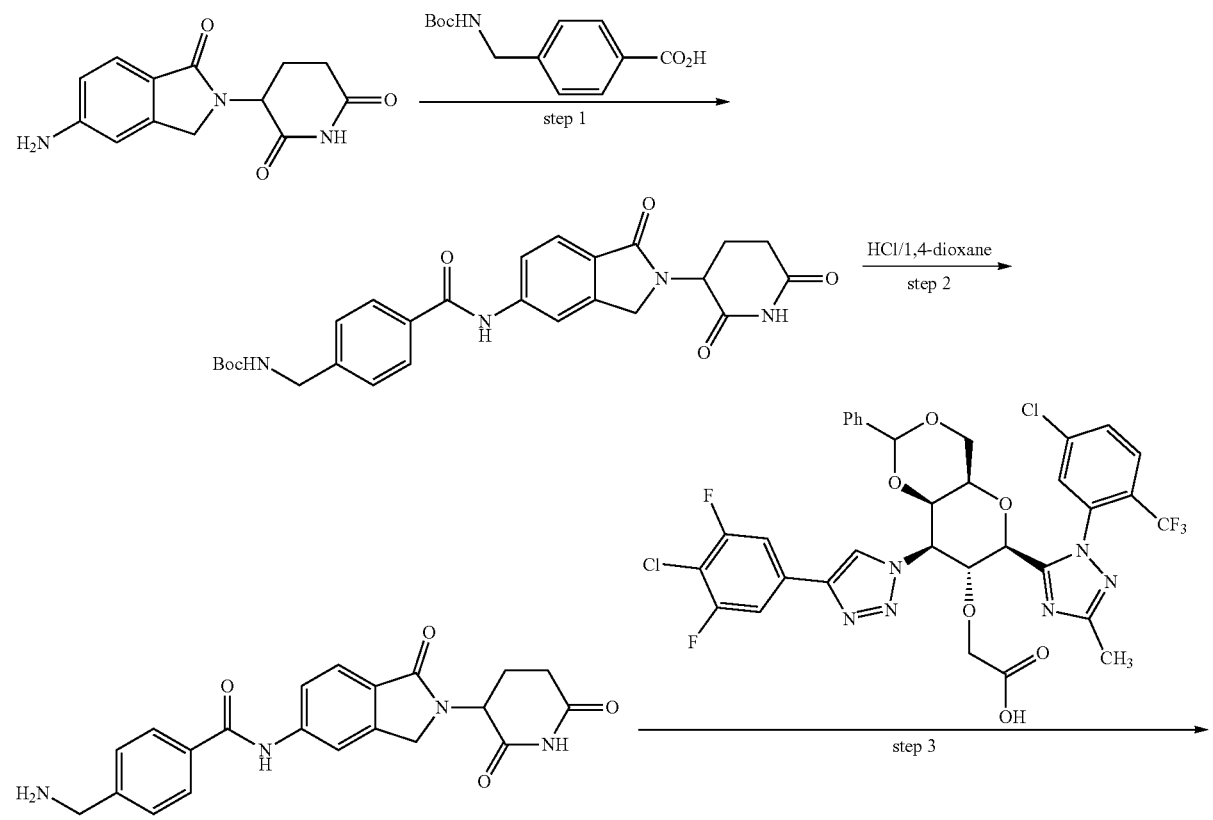

-continued

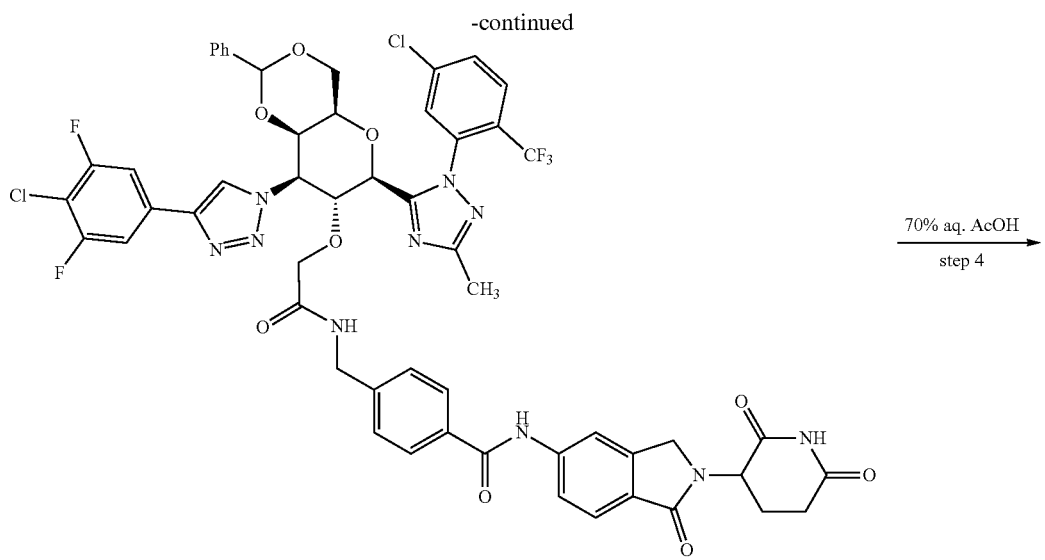

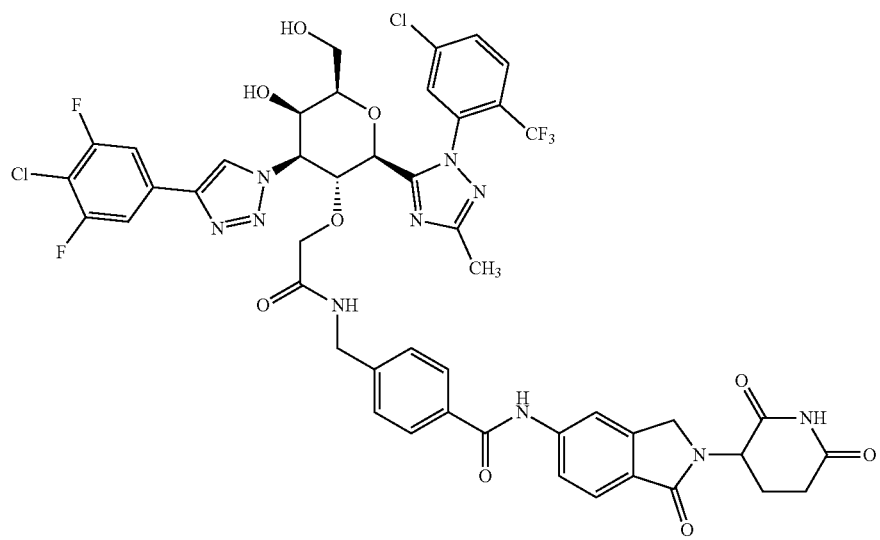

Example 2

Step 1. tert-Butyl (4-((2-(2,6-dioxopiperidin-3-yl)-1-oxoisoindolin-5-yl)carbamoyl)benzyl)carbamate A mixture of 4-(((tert-butoxycarbonyl)amino)methyl) benzoic acid (116 mg, 0.463 mmol), 3-(5-amino-1-oxoisoindolin-2-yl) piperidine-2,6-dione (100 mg, 0.386 mmol), 1-[bis(dimethylamino)methylene]-1H-1,2,3-triazolo[4,5-b] pyridinium 3-oxid hexafluorophosphate, (HATU) (183 mg, 0.482 mmol), and N,N-diisopropylethylamine (0.269 mL, 1.543 mmol) in DMF (4 mL) was stirred at rt for 7 days. The mixture was diluted with ethyl acetate (60 mL), washed with water (2×20 mL) and brine (20 mL), and dried over anhydrous $MgSO_4$. The desired product, tert-butyl (4-((2-(2,6-dioxopiperidin-3-yl)-1-oxoisoindolin-5-yl)carbamoyl)benzyl)carbamate (107 mg, 0.217 mmol, 56.3% yield), was isolated as a beige solid by ISCO chromatography (24 g silica gel, solid loading, 1-6% MeOH/$CH_2Cl_2$). LCMS $(M+H)^+$=493.1. $^1$H NMR (500 MHZ, DMSO-$d_6$) § 10.99 (s, 1H), 10.51 (s, 1H), 8.15 (s, 1H), 7.94 (br d, J=8.3 Hz, 2H), 7.84 (dd, J=8.4, 1.2 Hz, 1H), 7.72 (d, J=8.3 Hz, 1H), 7.50 (br t, J=6.1 Hz, 1H), 7.40 (d, J=8.3 Hz, 2H), 5.11 (dd, J=13.2, 5.0 Hz, 1H), 4.48 (d, J=17.1 Hz, 1H), 4.38-4.29 (m, 1H), 4.22 (br d, J=6.1 Hz, 2H), 2.99-2.86 (m, 1H), 2.66-2.57 (m, 1H), 2.44-2.38 (m, 1H), 2.07-1.97 (m, 1H), 1.41 (s, 9H).

Step 2. 4-(Aminomethyl)-N-(2-(2,6-dioxopiperidin-3-yl)-1-oxoisoindolin-5-yl)benzamide To a solution of tert-butyl (4-((2-(2,6-dioxopiperidin-3-yl)-1-oxoisoindolin-5-yl)carbamoyl)benzyl)carbamate (104 mg, 0.211 mmol) in dichloromethane (5 mL) at rt was added 4 N hydrogen chloride in 1,4-dioxane (5 mL, 20.00 mmol) over 1 min. The mixture was stirred at rt for 1 h, and then concentrated under vacuum to dryness to provide 4-(aminomethyl)-N-(2-(2,6-dioxopiperidin-3-yl)-1-oxoisoindolin-5-yl)benzamide, HCl (101 mg, 0.235 mmol, 112% yield) as a white solid. LCMS $(M+H)^+$=393.1.

Step 3. 4-((2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)methyl)-N-(2-(2,6-dioxopiperidin-3-yl)-1-oxoisoindolin-5-yl)benzamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (75 mg, 0.098 mmol), 4-(aminomethyl)-N-(2-(2,6-dioxopiperidin-3-yl)-1-oxoisoindolin-5-yl)benzamide, HCl (35 mg, 0.082 mmol), BOP (57.8 mg, 0.131 mmol), and N,N-diisopropylethylamine (0.071 mL, 0.408 mmol) in DMF (3 mL) was stirred at rt for 2 h. The mixture was diluted with ethyl acetate (50 mL), washed with water (2×20 mL), 0.5 N HCl solution (20 mL) and brine (20 mL), and dried over anhydrous MgSO$_4$. The desired product, 4-((2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)methyl)-N-(2-(2,6-dioxopiperidin-3-yl)-1-oxoisoindolin-5-yl)benzamide (66 mg, 0.058 mmol, 70.8% yield), was islasolated as a white solid solid by ISCO chromatography (24 g silica gel, solid loading, 0-6% methanol/dichloromethane). LCMS (M+H)$^+$=1141.1.

Step 4. 4-((2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)methyl)-N-(2-(2,6-dioxopiperidin-3-yl)-1-oxoisoindolin-5-yl)benzamide A mixture of 4-((2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)methyl)-N-(2-(2,6-dioxopiperidin-3-yl)-1-oxoisoindolin-5-yl)benzamide (66 mg, 0.058 mmol) in 70% acetic acid (4 mL) was heated at 70° C. for 18 h. The solution was diluted with methanol and injected to preparative HPLC (Column: Phenomenex Luna AXIA 5 u C18 30.0×100. Solvent A: 90% H$_2$O-10% methanol-0.1% TFA; Solvent B: 10% methanol-90% H$_2$O 0.1% TFA. Starting % B: 25; Final % B: 100. Gradient Time: 15 Min). The corrected fractions were combined, concentrated under vacuum, and extracted with dichloromethane (4×40 mL). The combined extract was dried over anhydrous Na$_2$SO$_4$. Removal of the solvent under vacuum provided the desired product, 4-((2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)methyl)-N-(2-(2,6-dioxopiperidin-3-yl)-1-oxoisoindolin-5-yl)benzamide (34 mg, 0.032 mmol, 54.7% yield), as a white solid. LCMS (M+H)$^+$=1053.1. $^1$H NMR (500 MHZ, METHANOL-d$_4$) δ 8.81 (s, 1H), 8.17 (s, 1H), 7.98 (d, J=8.8 Hz, 1H), 7.92-7.86 (m, 2H), 7.80 (d, J=8.0 Hz, 3H), 7.78-7.74 (m, 1H), 7.64 (d, J=8.0 Hz, 2H), 7.21 (d, J=8.3 Hz, 2H), 5.21-5.11 (m, 2H), 5.03 (br t, J=9.5 Hz, 1H), 4.59-4.48 (m, 3H), 4.40-4.33 (m, 1H), 4.29-4.22 (m, 1H), 4.14 (d, J=2.5 Hz, 1H), 4.04 (br d, J=14.9 Hz, 1H), 3.78 (d, J=15.1 Hz, 1H), 3.74-3.69 (m, 1H), 3.69-3.61 (m, 2H), 2.99-2.88 (m, 1H), 2.86-2.77 (m, 1H), 2.54 (qd, J=13.2, 4.5 Hz, 1H), 2.45 (s, 3H), 2.25-2.18 (m, 1H). hGal-3 IC$_{50}$=0.109 UM; hCRBN IC$_{50}$=0.269 μM.

Example 3. 4-(cis-3-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)cyclobutoxy)-N-(2-(2,6-dioxopiperidin-3-yl)-1-oxoisoindolin-5-yl)benzamide

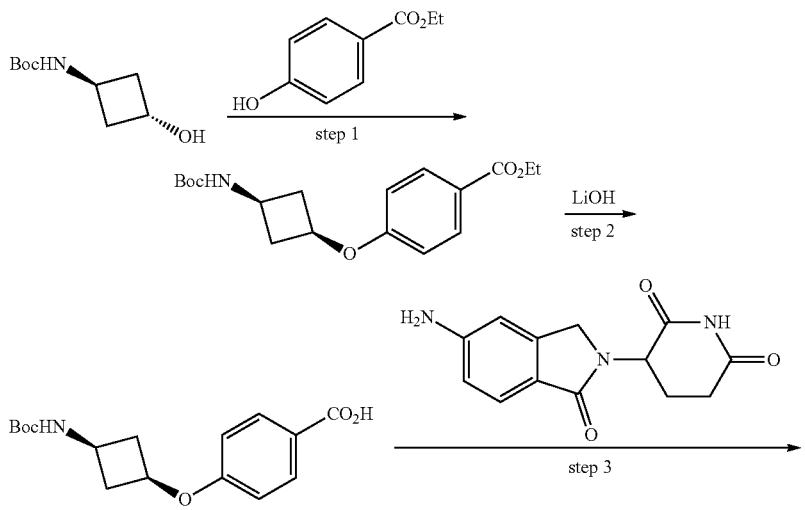

-continued
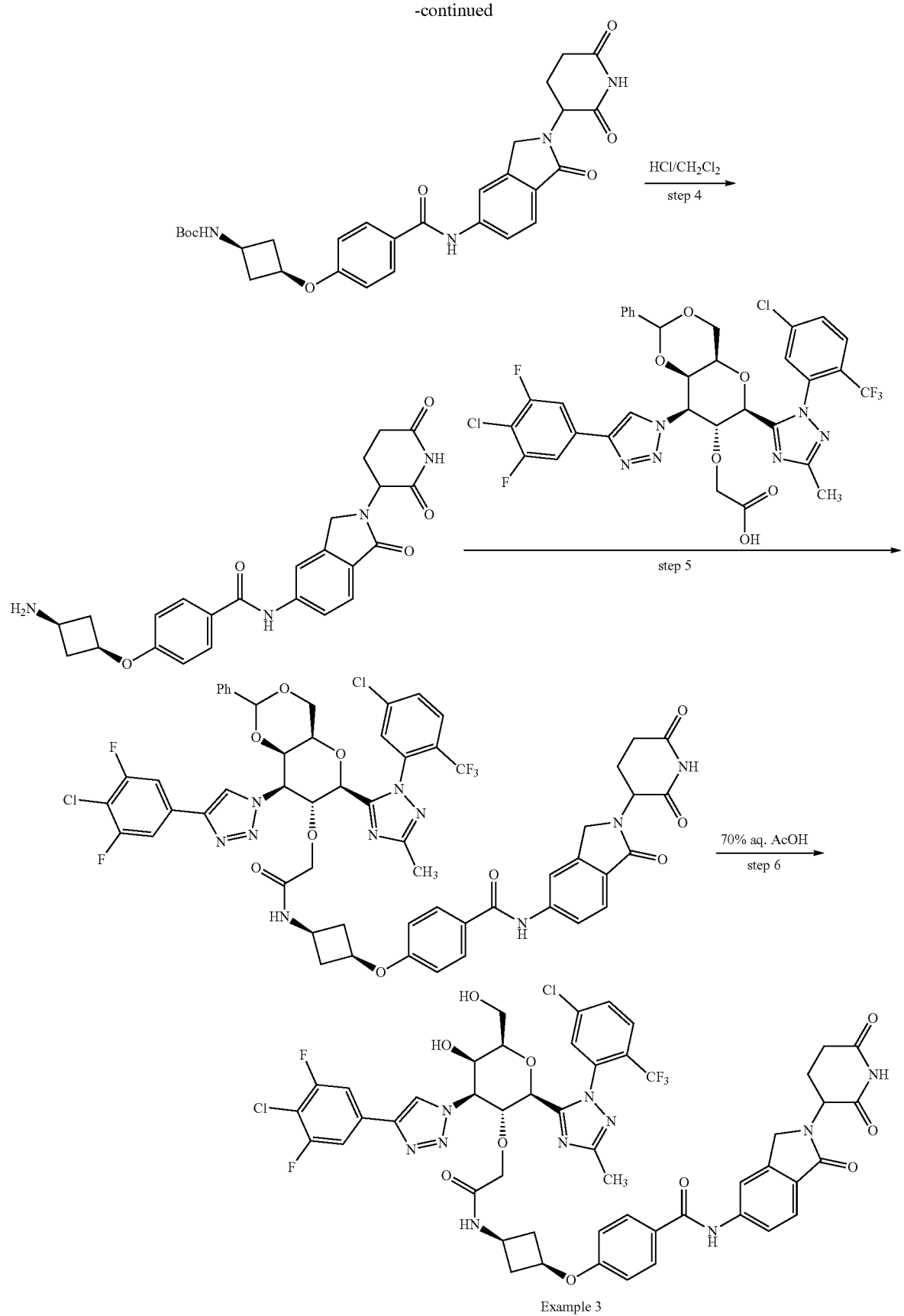
Example 3

Step 1. Ethyl 4-(cis-3-((tert-butoxycarbonyl)amino) cyclobutoxy)benzoate

To a mixture of ethyl 4-hydroxybenzoate (0.300 g, 1.805 mmol), tert-butyl trans-3-hydroxycyclobutyl) carbamate (0.423 g, 2.257 mmol), and triphenylphosphine (0.710 g, 2.71 mmol) in toluene (10 mL) at rt was added diisopropyl azodicarboxylate (DIAD) (0.533 mL, 2.71 mmol) over 1 min. The resulting solution was heated at 105° C. for 16 h. Upon cooling to rt, the reaction solution was diluted with ethyl acetate (50 mL) and silica gel (5 g) was added. The volatiles were removed under vacuum. The residue was subjected to ISCO chromatography (80 g silica gel, 10-35% ethyl acetate/hexane) to provide ethyl 4-(cis-3-((tert-butoxycarbonyl)amino)cyclobutoxy)benzoate (0.595 g, 1.774 mmol, 98% yield) as a white solid. LCMS $(M+H)^+=336.3$. $^1H$ NMR (500 MHZ, DMSO-$d_6$) δ 7.95-7.82 (m, 2H), 7.21 (br d, J=8.0 Hz, 1H), 7.03-6.89 (m, 2H), 4.48 (t, J=7.0 Hz, 1H), 4.28 (q, J=7.2 Hz, 2H), 3.80-3.63 (m, 1H), 2.79 (td, J=9.1, 7.3 Hz, 2H), 2.02-1.98 (m, 2H), 1.39 (s, 9H), 1.31 (t, J=7.0 Hz, 3H).

Step 2. 4-(cis-3-((tert-Butoxycarbonyl)amino)cyclobutoxy)benzoic acid

To a solution of ethyl 4-(cis-3-((tert-butoxycarbonyl) amino)cyclobutoxy)benzoate (300 mg, 0.894 mmol) in tetrahydrofuran (20 mL) and methanol (5 mL) at rt was added lithium hydroxide (129 mg, 5.37 mmol) in water (5 mL) over 1 min. The mixture was stirred at rt for 70 h, and then concentrated under vacuum to a volume of approximately 5 mL. The residue was diluted with water (15 mL) and acidified with 1 N HCl to pH=5-6. The precipitating product, 4-(cis-3-((tert-butoxycarbonyl)amino)cyclobutoxy)benzoic acid (258 mg, 0.839 mmol, 94% yield), was collected as a white solid by suction filtration and dried at 50° C. under vacuum. LCMS $(M+H)^+=308.3$. $^1H$ NMR (500 MHz, DMSO-$d_6$) δ 12.80-12.47 (m, 1H), 7.94-7.81 (m, 2H), 7.21 (br d, J=8.0 Hz, 1H), 6.93 (d, J=8.8 Hz, 2H), 4.47 (quin, J=7.1 Hz, 1H), 3.77-3.65 (m, 1H), 2.86-2.72 (m, 2H), 2.08-1.92 (m, 2H), 1.39 (s, 9H).

Step 3. tert-Butyl(cis-3-(4-((2-(2,6-dioxopiperidin-3-yl)-1-oxoisoindolin-5-yl)carbamoyl)phenoxy)cyclobutyl)carbamate A mixture of 4-(cis-3-((tert-butoxycarbonyl)amino)cyclobutoxy)benzoic acid (122 mg, 0.398 mmol), 3-(5-amino-1-oxoisoindolin-2-yl) piperidine-2,6-dione (86 mg, 0.332 mmol), HATU (151 mg, 0.398 mmol), and N,N-diisopropylethylamine (0.232 mL, 1.327 mmol) was stirred at rt for 4 days. The mixture was diluted with ethyl acetate (60 mL), washed with water (2×20 mL) and saturated NaHCO$_3$ solution (20 mL), and dried over anhydrous MgSO$_4$. The desired product, tert-butyl (cis-3-(4-((2-(2,6-dioxopiperidin-3-yl)-1-oxoisoindolin-5-yl)carbamoyl)phenoxy)cyclobutyl) carbamate (68 mg, 0.124 mmol, 37.4% yield), was isolated as a white solid by ISCO chromatography (40 g silica gel, solid loading, 1-8% MeOH/CH$_2$Cl$_2$). LCMS $(M+H)^+$ =308.3. $^1H$ NMR (500 MHZ, DMSO-$d_6$) § 10.98 (s, 1H), 10.39 (s, 1H), 8.14 (s, 1H), 7.96 (d, J=8.8 Hz, 2H), 7.83 (dd, J=8.4, 1.5 Hz, 1H), 7.70 (d, J=8.5 Hz, 1H), 7.22 (br d, J=8.0 Hz, 1H), 7.00 (d, J=8.8 Hz, 2H), 5.11 (dd, J=13.3, 5.1 Hz, 1H), 4.56-4.43 (m, 2H), 4.38-4.28 (m, 1H), 3.79-3.67 (m, 1H), 3.00-2.87 (m, 1H), 2.86-2.75 (m, 2H), 2.67-2.58 (m, 1H), 2.45-2.36 (m, 1H), 2.06-1.97 (m, 3H), 1.39 (s, 9H).

Step 4. 4-(cis-3-Aminocyclobutoxy)-N-(2-(2,6-dioxopiperidin-3-yl)-1-oxoisoindolin-5-yl)benzamide To a solution of tert-butyl (cis-3-(4-((2-(2,6-dioxopiperidin-3-yl)-1-oxoisoindolin-5-yl)carbamoyl)phenoxy)cyclobutyl)carbamate (68 mg, 0.124 mmol) in dichloromethane (4 mL) at rt was added 4 N hydrogen chloride in 1,4-dioxane (4 mL, 16.00 mmol) over 1 min. The mixture was stirred at rt for 1 h, and then concentrated under vacuum to dryness to provide 4-(cis-3-aminocyclobutoxy)-N-(2-(2, 6-dioxopiperidin-3-yl)-1-oxoisoindolin-5-yl)benzamide hydrochloride (66 mg, 0.136 mmol, 110% yield) as a white solid. LCMS $(M+H)^+=449.1$.

Step 5. 4-(cis-3-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)cyclobutoxy)-N-(2-(2,6-dioxopiperidin-3-yl)-1-oxoisoindolin-5-yl)benzamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (60.8 mg, 0.079 mmol), 4-(cis-3-aminocyclobutoxy)-N-(2-(2,6-dioxopiperidin-3-yl)-1-oxoisoindolin-5-yl)benzamide, HCl (32 mg, 0.066 mmol), BOP (43.8 mg, 0.099 mmol), and N,N-diisopropylethylamine (0.058 mL, 0.330 mmol) in DMF (2 mL) was stirred at rt for 2 h. The mixture was diluted with ethyl acetate (50 mL), washed with water (2×20 mL), 0.5 N HCl solution (20 mL) and brine (20 mL), and dried over anhydrous MgSO$_4$. The desired product, 4-((1S,3s)-3-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy) acetamido)cyclobutoxy)-N-(2-(2,6-dioxopiperidin-3-yl)-1-oxoisoindolin-5-yl)benzamide (47 mg, 0.039 mmol, 59.5% yield), was isolated as a white solid by ISCO chromatography (12 g silica gel, solid loading, 0-6% methanol/dichloromethane). LCMS $(M+H)^+=1197.6$.

Step 6. 4-(cis-3-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl) tetrahydro-2H-pyran-3-yl)oxy)acetamido) cyclobutoxy)-N-(2-(2,6-dioxopiperidin-3-yl)-1-oxoisoindolin-5-yl)benzamide A mixture of 4-(cis-3-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)cyclobutoxy)-N-(2-(2,6-dioxopiperidin-3-yl)-1-oxoisoindolin-5-yl)benzamide (47 mg, 0.039 mmol) in 70% acetic acid (1.5 mL) was heated at 75° C. for 15 h. The solution was diluted with methanol and injected to preparative HPLC (Column: Phenomenex Luna AXIA 5 u C18 21.2×100. Solvent A: 90% H$_2$O-10% methanol-0.1% TFA; Solvent B: 10% methanol-90% H$_2$O 0.1% TFA. Starting % B: 25; Final % B: 100. Gradient Time: 15 Min). The corrected fractions were combined, concentrated under vacuum, and extracted with dichloromethane (4×30 mL). The combined extract was dried over anhydrous Na$_2$SO$_4$.

Removal of the solvent under vacuum provided the desired product, 4-(cis-3-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy) acetamido)cyclobutoxy)-N-(2-(2,6-dioxopiperidin-3-yl)-1-oxoisoindolin-5-yl)benzamide (28 mg, 0.025 mmol, 63.0% yield), as a white solid. LCMS (M+H)$^+$=1109.4. $^1$H NMR (500 MHZ, METHANOL-d$_4$) δ 8.82 (s, 1H), 8.16 (s, 1H), 7.99 (d, J=8.8 Hz, 1H), 7.97-7.93 (m, 2H), 7.91-7.88 (m, 2H), 7.82-7.79 (m, 1H), 7.77-7.74 (m, 1H), 7.70-7.66 (m, 2H), 6.96-6.92 (m, 2H), 5.20-5.13 (m, 2H), 4.99 (br t, J=9.6 Hz, 1H), 4.58-4.46 (m, 4H), 4.14 (d, J=2.8 Hz, 1H), 3.95-3.85 (m, 2H), 3.74-3.63 (m, 4H), 2.99-2.88 (m, 1H), 2.87-2.73 (m, 3H), 2.53 (qd, J=13.3, 4.5 Hz, 1H), 2.47 (s, 3H), 2.24-2.17 (m, 1H), 2.01 (dt, J=10.9, 8.6 Hz, 1H), 1.94-1.86 (m, 1H). hGal-3 IC$_{50}$=0.070 μM; hCRBN IC$_{50}$=0.126 μM.

Example 4. 5-(cis-3-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido) cyclobutoxy)-N-(2-(2,6-dioxopiperidin-3-yl)-1-oxoisoindolin-5-yl)picolinamide

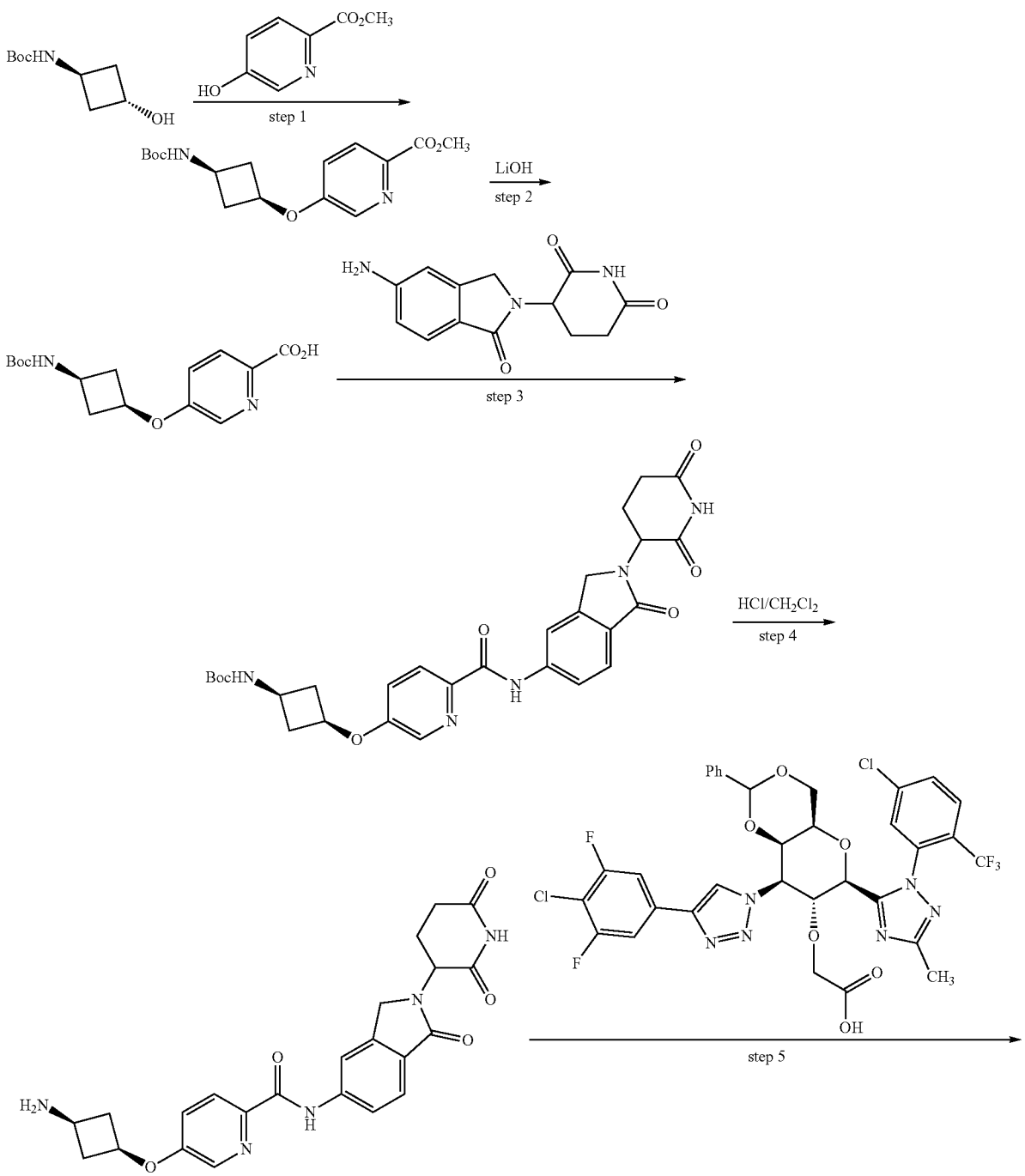

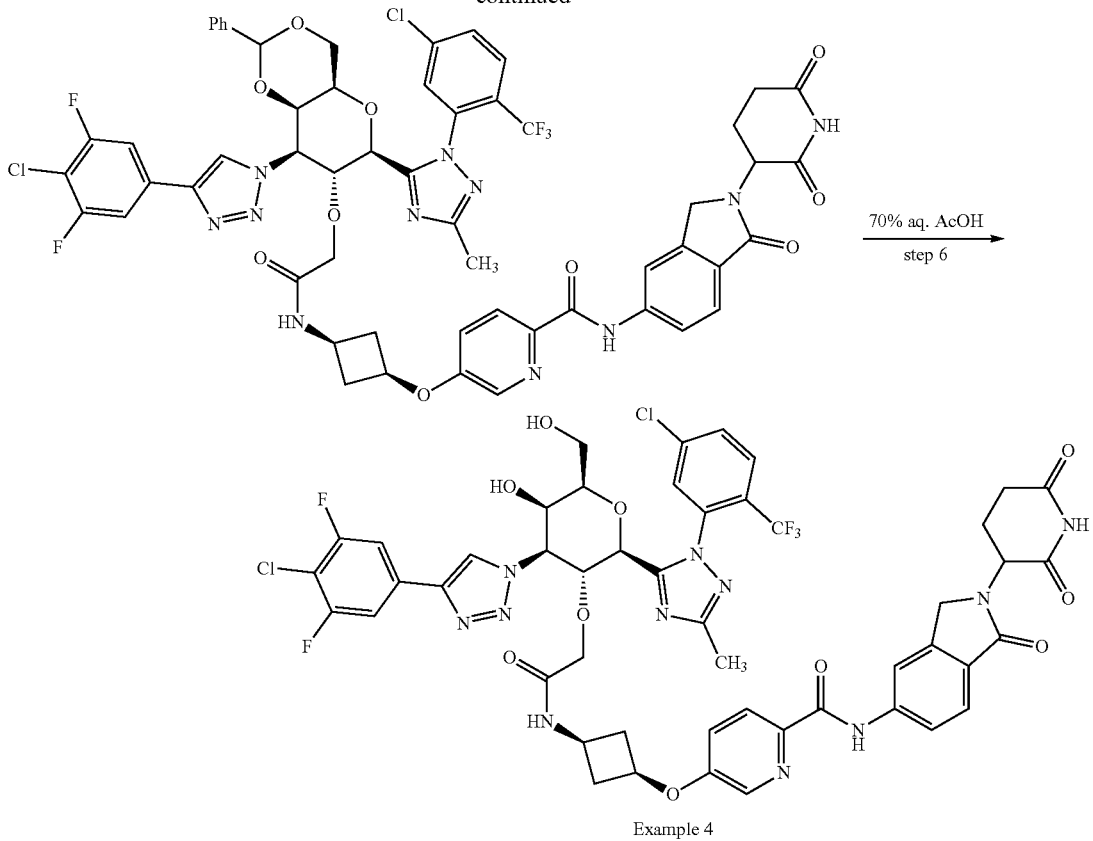

Example 4

Step 1. Methyl 5-(cis-3-((tert-butoxycarbonyl)amino)cyclobutoxy)picolinate

To a mixture of methyl 5-hydroxypicolinate (0.488 g, 3.19 mmol), tert-butyl trans-3-hydroxycyclobutyl) carbamate (0.716 g, 3.82 mmol), and triphenylphosphine (1.254 g, 4.78 mmol) in toluene (18 mL) at rt was added diisopropyl azodicarboxylate (DIAD) (0.941 mL, 4.78 mmol) over 1 min. The resulting solution was heated at 105° C. for 15 h. Upon cooling to rt, the reaction solution was diluted with ethyl acetate (60 mL) and silica gel (5 g) was added. The volatiles were removed under vacuum. The residue was subjected to ISCO chromatography (80 g silica gel, 20-65% ethyl acetate/hexane) to provide methyl 5-(cis-3-((tert-butoxycarbonyl)amino)cyclobutoxy)picolinate (0.820 g, 2.54 mmol, 80% yield) as a white solid. LCMS (M+H)$^+$=323.0. $^1$H NMR (500 MHZ, DMSO-d$_6$) δ 8.32 (d, J=2.8 Hz, 1H), 8.01 (d, J=8.8 Hz, 1H), 7.41 (dd, J=8.8, 2.8 Hz, 1H), 7.23 (br d, J=8.0 Hz, 1H), 4.57 (br t, J=7.0 Hz, 1H), 3.84 (s, 3H), 3.78-3.64 (m, 1H), 2.90-2.74 (m, 2H), 2.10-1.94 (m, 2H), 1.38 (s, 9H).

Step 2. 5-(cis-3-((tert-Butoxycarbonyl)amino)cyclobutoxy)picolinic acid

To a solution of methyl 5-(cis-3-((tert-butoxycarbonyl)amino)cyclobutoxy) picolinate (812 mg, 2.52 mmol) in tetrahydrofuran (50 mL) and methanol (12 mL) at rt was added lithium hydroxide (362 mg, 15.11 mmol) in water (12 mL) over 1 min. The mixture was heated at 50° C. for 2.5 h, and then concentrated under vacuum to a volume of approximately 5 mL. The residue was acidified with 1 N HCl to pH=5-6, and the precipitating product, 5-(cis-3-((tert-butoxycarbonyl)amino)cyclobutoxy)picolinic acid (650 mg, 2.108 mmol, 84% yield), was collected as a white solid by suction filtration and dried under vacuum at 50° C. LCMS (M+H)$^+$=309.0.

Step 3. tert-Butyl (cis-3-((6-((2-(2,6-dioxopiperidin-3-yl)-1-oxoisoindolin-5-yl)carbamoyl)pyridin-3-yl)oxy)cyclobutyl)carbamate A mixture of 5-(cis-3-((tert-butoxycarbonyl)amino)cyclobutoxy)picolinic acid (114 mg, 0.370 mmol), 3-(5-amino-1-oxoisoindolin-2-yl) piperidine-2,6-dione (80 mg, 0.309 mmol), HATU (147 mg, 0.386 mmol), and N,N-diisopropylethylamine (0.216 mL, 1.234 mmol) was stirred at rt for 48 h. The mixture was diluted with ethyl acetate (60 mL), washed with water (2×15 mL) and brine (15 mL), and dried over anhydrous MgSO$_4$. The desired product, tert-butyl (cis-3-((6-((2-(2,6-dioxopiperidin-3-yl)-1-oxoisoindolin-5-yl)carbamoyl)pyridin-3-yl)oxy)cyclobutyl)carbamate (56 mg, 0.102 mmol, 33.0% yield), was isolated as a white solid by ISCO chromatography (40 g silica gel, solid loading, 0-8% methanol/dichloromethane). LCMS (M+H)$^+$=550.2. $^1$H NMR (500 MHz, DMSO-d$_6$) § 10.98 (s, 1H), 10.79 (s, 1H), 8.35 (d, J=2.8 Hz, 1H), 8.26 (s, 1H), 8.13 (d, J=8.8 Hz, 1H), 7.98 (dd, J=8.4, 1.2 Hz, 1H), 7.71 (d, J=8.3 Hz, 1H), 7.53 (dd, J=8.8, 2.8 Hz, 1H), 7.25 (br d, J=8.0 Hz, 1H), 5.11 (dd, J=13.2, 5.2 Hz, 1H), 4.62 (br t, J=6.9 Hz, 1H), 4.48 (d, J=17.3 Hz, 1H), 4.39-4.27 (m, 1H), 3.81-3.69 (m, 1H), 3.01-2.89 (m, 1H), 2.85 (br d, J=6.9 Hz, 2H), 2.67-2.58 (m, 1H), 2.47-2.37 (m, 1H), 2.11-1.98 (m, 3H), 1.39 (s, 9H).

Step 4. 5-(cis-3-Aminocyclobutoxy)-N-(2-(2,6-dioxopiperidin-3-yl)-1-oxoisoindolin-5-yl)picolinamide To a solution of tert-butyl ((1s,3s)-3-((6-((2-(2,6-dioxopiperidin-3-yl)-1-oxoisoindolin-5-yl)carbamoyl)pyridin-3-yl)

oxy)cyclobutyl)carbamate (55 mg, 0.100 mmol) in dichloromethane (3 mL) at rt was added 4 N hydrogen chloride in 1,4-dioxane (3 mL, 12.00 mmol) over 1 min. The mixture was stirred at rt for 4 h, and then concentrated under vacuum to dryness to provide 5-(cis-3-aminocyclobutoxy)-N-(2-(2, 6-dioxopiperidin-3-yl)-1-oxoisoindolin-5-yl)picolinamide, 2 HCl (57 mg, 0.109 mmol, 109% yield) as a white solid solid. LCMS (M+H)$^+$=450.1.

Step 5. 5-((cis-3-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido)cyclobutoxy)-N-(2-(2,6-dioxopiperidin-3-yl)-1-oxoisoindolin-5-yl) picolinamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (88 mg, 0.114 mmol), 5-(cis-3-aminocyclobutoxy)-N-(2-(2,6-dioxopiperidin-3-yl)-1-oxoisoindolin-5-yl)picolinamide, 2 HCl (57 mg, 0.099 mmol), BOP (70.3 mg, 0.159 mmol), and N,N-diisopropylethylamine (0.104 mL, 0.596 mmol) in DMF (3 mL) was stirred at rt for 2 h. The mixture was diluted with ethyl acetate (50 mL), washed with water (2×20 mL), 0.5 N HCl solution (20 mL) and brine (20 mL), and dried over anhydrous MgSO$_4$. Removal of the solvent provided the desired product, 5-((cis)-3-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano [3,2-d][1,3]dioxin-7-yl)oxy)acetamido)cyclobutoxy)-N-(2-(2,6-dioxopiperidin-3-yl)-1-oxoisoindolin-5-yl) picolinamide (109 mg, 0.091 mmol, 92% yield), as a beige solid.

Step 6. 5-(cis-3-(2-(((2S,3R,4S,5R,6R)-2-(1-(5-Chloro-2-(trifluoromethyl)phenyl)-3-methyl-1H-1,2, 4-triazol-5-yl)-4-(4-(4-chloro-3,5-difluorophenyl)-1H-1,2,3-triazol-1-yl)-5-hydroxy-6-(hydroxymethyl) tetrahydro-2H-pyran-3-yl)oxy)acetamido) cyclobutoxy)-N-(2-(2,6-dioxopiperidin-3-yl)-1-oxoisoindolin-5-yl)picolinamide A mixture of 5-(cis-3-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetamido) cyclobutoxy)-N-(2-(2,6-dioxopiperidin-3-yl)-1-oxoisoindolin-5-yl)picolinamide (109 mg, 0.091 mmol) in 70% acetic acid (6 mL) was heated at 70° C. for 18 h. The solution was diluted with methanol and injected to preparative HPLC (Column: Phenomenex Luna AXIA 5 u C18 21.2×100. Solvent A: 90% H$_2$O-10% methanol-0.1% TFA; Solvent B: 10% methanol-90% H$_2$O 0.1% TFA. Starting % B: 28; Final % B: 100. Gradient Time: 15 Min). The corrected fractions were combined, concentrated under vacuum, and extracted with dichloromethane (4×40 mL). The combined extract was dried over anhydrous Na2SO$_4$. Removal of the solvent under vacuum provided the desired product, 5-(cis-3-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy) acetamido)cyclobutoxy)-N-(2-(2,6-dioxopiperidin-3-yl)-1-oxoisoindolin-5-yl)picolinamide (49 mg, 0.042 mmol, 46.1% yield), as a white solid. LCMS (M+H)$^+$=1110.0. $^1$H NMR (500 MHZ, METHANOL-d$_4$) δ 8.82 (s, 1H), 8.28 (d, J=2.8 Hz, 1H), 8.24 (s, 1H), 8.18 (d, J=8.8 Hz, 1H), 7.99 (d, J=8.8 Hz, 1H), 7.92-7.80 (m, 4H), 7.69-7.64 (m, 2H), 7.40 (dd, J=8.5, 2.8 Hz, 1H), 5.21-5.13 (m, 2H), 5.00 (br t, J=9.8 Hz, 1H), 4.61-4.48 (m, 4H), 4.14 (d, J=2.8 Hz, 1H), 3.95-3.87 (m, 2H), 3.74-3.63 (m, 4H), 2.99-2.89 (m, 1H), 2.89-2.77 (m, 3H), 2.60-2.50 (m, 1H), 2.47 (s, 3H), 2.25-2.18 (m, 1H), 2.10-2.01 (m, 1H), 1.96-1.87 (m, 1H). hGal-3 IC$_{50}$=0.081 μM; HCRBNIC$_{50}$=0.174 μM.

Example 5 and 6. 5-(cis-3-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy) acetamido)cyclobutoxy)-N-(2-((S)-2,6-dioxopiperidin-3-yl)-1-oxoisoindolin-5-yl) picolinamide and 5-(cis-3-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy) acetamido)cyclobutoxy)-N-(2-((R)-2,6-dioxopiperidin-3-yl)-1-oxoisoindolin-5-yl) picolinamide

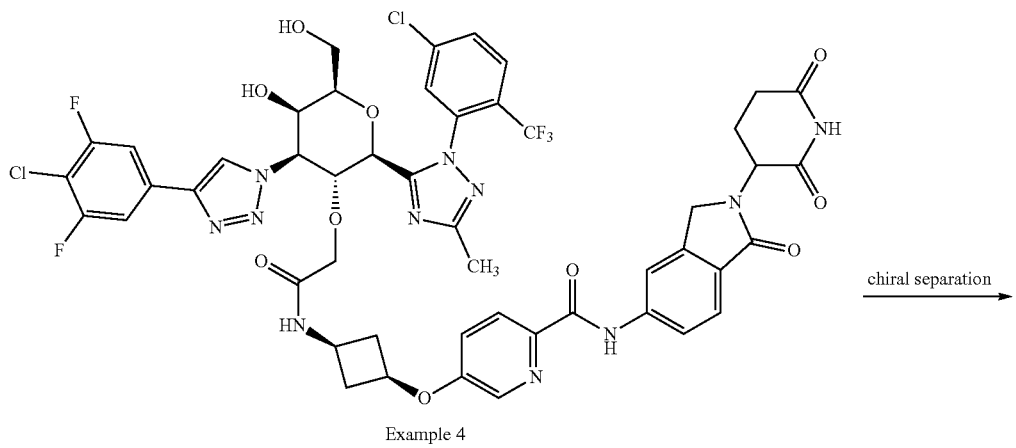

Example 4 chiral separation →

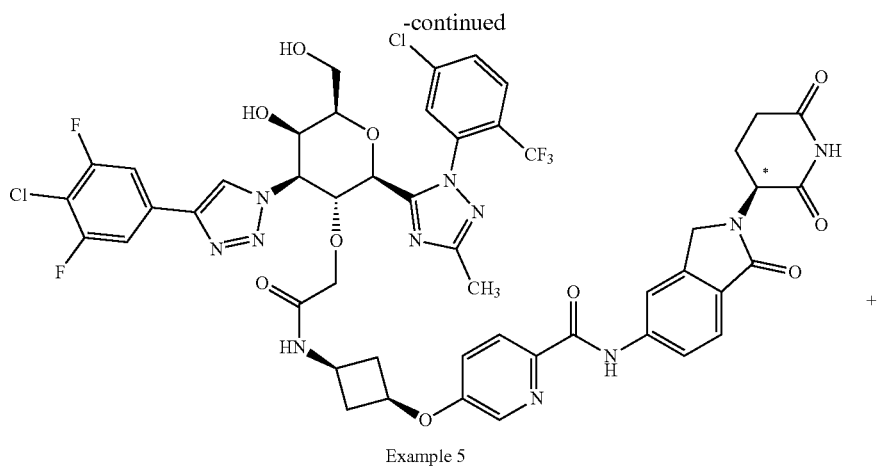

Example 5

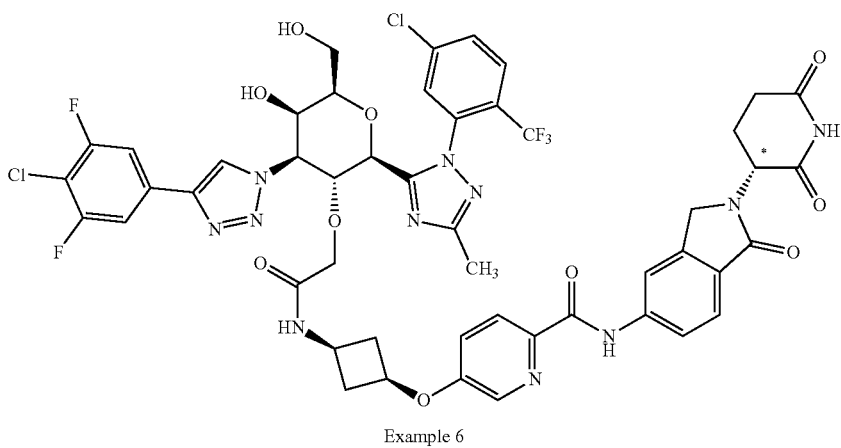

Example 6 absolute stereochemistry at * not determined 5-(cis-3-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetamido)cyclobutoxy)-N-(2-(2,6-dioxopiperidin-3-yl)-1-oxoisoindolin-5-yl)picolinamide (Example 3) (44 mg) was separated under the chiral SFC conditions described below to afford Example 4 (20 mg, 0.018 mmol, 45.0% yield) and Example 5 (18.5 mg, 0.016 mmol, 41.6% yield). Both products are white solid.

Instrument: Thar 350
Colum: Chiral IC (3×25 cm, 5 micron)
Column Temp. 40° C.
Flow rate: 130/min
Mobile Phase: $CO_2$/[MeOH/$CH_3$CN=50:50]=35/65
Back Pressure 100 bar
Injection Volume: 2.0 mL (Conc.=4 mg/mL)
Detector Wavelength: 220 nm Example 5

LCMS (M+H)$^+$=1110.1. $^1$H NMR (500 MHZ, METHANOL-$d_4$) δ 8.82 (s, 1H), 8.28 (br s, 1H), 8.24 (s, 1H), 8.18 (br d, J=8.0 Hz, 1H), 7.99 (d, J=9.1 Hz, 1H), 7.93-7.79 (m, 4H), 7.66 (d, J=8.0 Hz, 2H), 7.40 (dd, J=8.8, 2.5 Hz, 1H), 5.21-5.13 (m, 2H), 5.00 (br t, J=9.6 Hz, 1H), 4.61-4.47 (m, 4H), 4.14 (d, J=2.8 Hz, 1H), 3.97-3.85 (m, 2H), 3.72-3.65 (m, 4H), 2.99-2.89 (m, 1H), 2.88-2.76 (m, 3H), 2.60-2.50 (m, 1H), 2.47 (s, 3H), 2.21 (dtd, J=12.7, 5.2, 2.2 Hz, 1H), 2.10-2.00 (m, 1H), 1.97-1.87 (m, 1H). hGal-3 IC$_{50}$=0.084 μM; hCRBN IC$_{50}$=0.039 μM.

Example 6

LCMS (M+H)$^+$=1110.1. $^1$H NMR (500 MHZ, METHANOL-$d_4$) δ 8.82 (s, 1H), 8.28 (d, J=2.5 Hz, 1H), 8.24 (s, 1H), 8.18 (d, J=8.8 Hz, 1H), 7.99 (d, J=9.1 Hz, 1H), 7.92-7.80 (m, 4H), 7.66 (d, J=8.0 Hz, 2H), 7.40 (dd, J=8.8, 2.8 Hz, 1H), 5.21-5.13 (m, 2H), 5.00 (br t, J=9.8 Hz, 1H), 4.60-4.48 (m, 4H), 4.14 (d, J=2.8 Hz, 1H), 3.95-3.87 (m, 2H), 3.74-3.64 (m, 4H), 2.99-2.89 (m, 1H), 2.89-2.77 (m, 3H), 2.59-2.49 (m, 1H), 2.47 (s, 3H), 2.25-2.18 (m, 1H), 2.09-2.01 (m, 1H), 1.97-1.88 (m, 1H). hGal-3 IC$_{50}$=0.074 μM; hCRBN IC$_{50}$>50 μM.

Example 7. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-1-oxoisoindolin-5-yl)benzamide
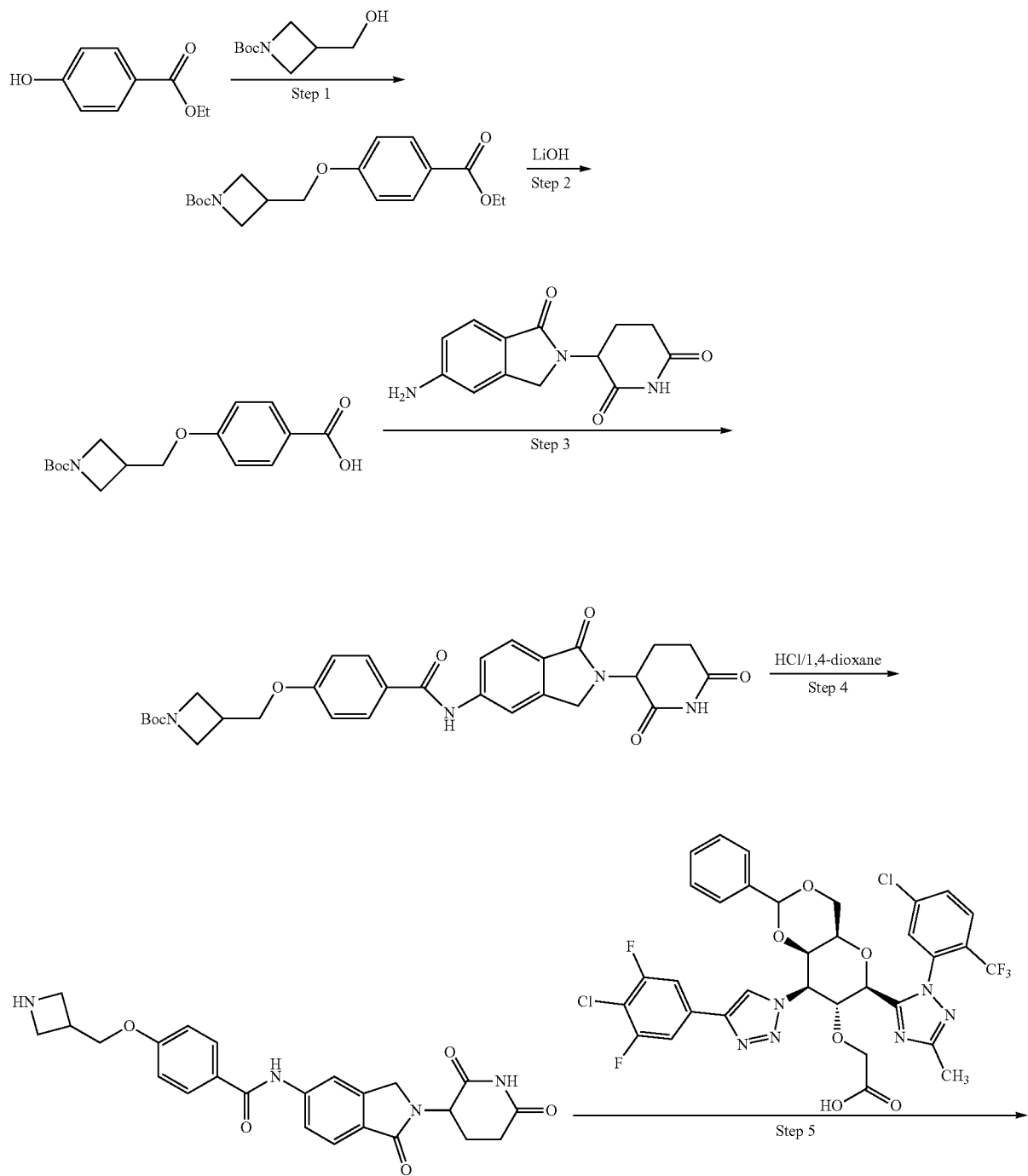

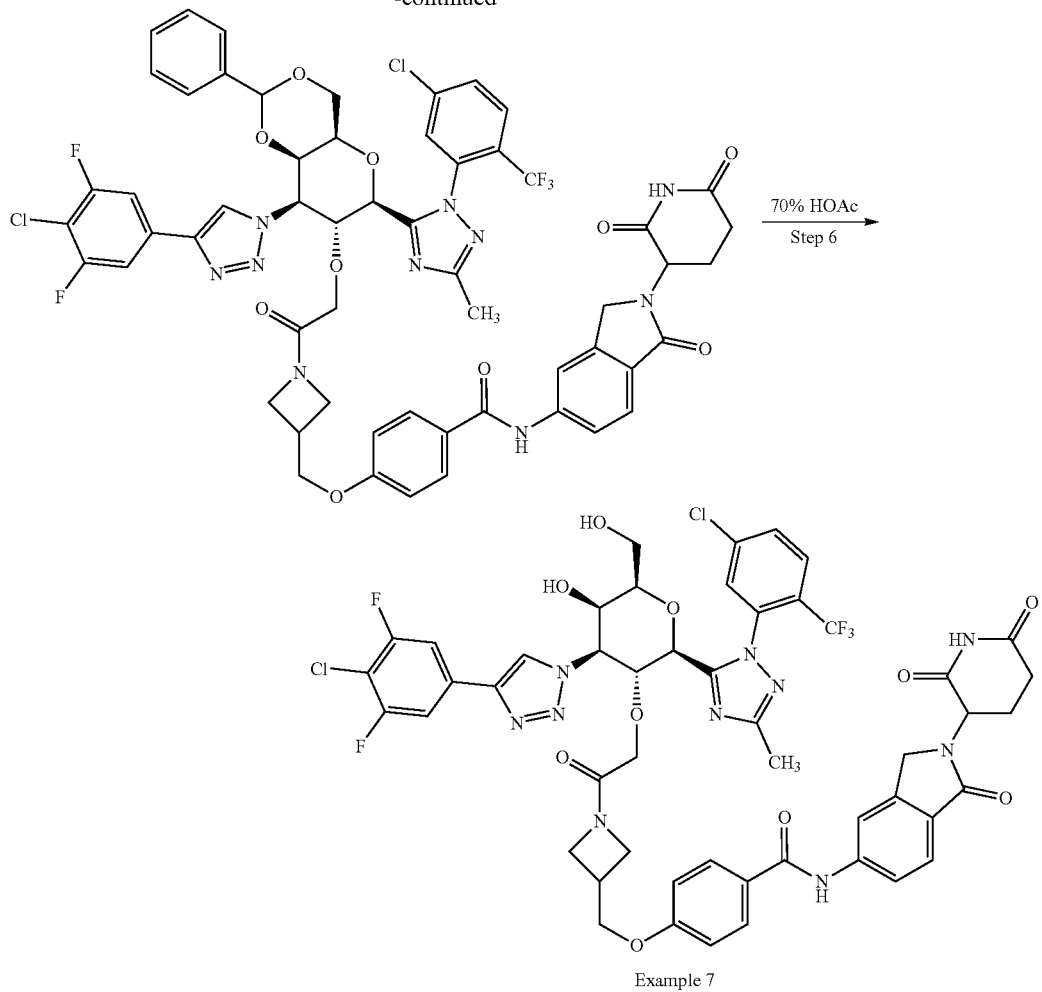

Example 7

Step 1. tert-Butyl 3-((4-(ethoxycarbonyl) phenoxy) methyl) azetidine-1-carboxylate To a mixture of ethyl 4-hydroxybenzoate (0.35 g, 2.106 mmol), tert-butyl cis-3-hydroxycyclobutyl) carbamate (0.493 g, 2.63 mmol), and triphenylphosphine (0.829 g, 3.16 mmol) in toluene (12 mL) at rt was added diisopropyl azodicarboxylate (DIAD) (0.622 mL, 3.16 mmol) over 1 min. The resulting solution was heated at 105° C. for 16 h. Upon cooling to rt, the reaction solution was diluted with ethyl acetate (50 mL) and silica gel (5 g) was added. The volatiles were removed under vacuum. The residue was subjected to ISCO chromatography (80 g silica gel, 0-35% ethyl acetate/hexane) to give ethyl 4-(trans-3-((tert-butoxycarbonyl)amino)cyclobutoxy)benzoate (704 mg, 2.099 mmol, 100% yield) as viscous oil. LCMS (M+H)$^+$=336.0. $^1$H NMR (400 MHZ, chloroform-d) δ 8.19-7.78 (m, 2H), 7.06-6.62 (m, 2H), 4.35 (q, J=7.1 Hz, 2H), 4.14 (d, J=6.6 Hz, 2H), 4.10 (t, J=8.5 Hz, 2H), 3.80 (dd, J=8.8, 5.2 Hz, 2H), 2.98 (ttt, J=8.3, 6.6, 5.2 Hz, 1H), 1.45 (s, 9H), 1.38 (t, J=7.1 Hz, 3H).

Step 2. 4-((1-(tert-Butoxycarbonyl) azetidin-3-yl) methoxy)benzoic acid

To a solution of tert-butyl 3-((4-(ethoxycarbonyl) phenoxy)methyl) azetidine-1-carboxylate (300 mg, 0.894 mmol) in tetrahydrofuran (10 mL) and methanol (2.5 mL) at rt was added lithium hydroxide (129 mg, 5.37 mmol) in water (2.5 mL) over 1 min. The mixture was stirred at rt for 60 h, and then concentrated under vacuum to a volume of approximately 5 mL. The residue was diluted with water (15 mL) and acidified with 1 N HCl to pH=5-6. The precipitating product, 4-((1-(tert-butoxycarbonyl) azetidin-3-yl) methoxy)benzoic acid (218 mg, 0.709 mmol, 79% yield), was collected as a white solid by suction filtration and dried at 50° C. under vacuum. $^1$H NMR (400 MHZ, Methanol-d$_4$) δ 8.10-7.88 (m, 2H), 7.08-6.94 (m, 2H), 4.21 (d, J=6.1 Hz, 2H), 4.10 (t, J=8.5 Hz, 2H), 3.83 (dd, J=8.7, 5.3 Hz, 2H), 3.06 (tdd, J=8.4, 7.0, 4.2 Hz, 1H), 1.47 (s, 9H).

Step 3. tert-Butyl 3-((4-((2-(2,6-dioxopiperidin-3-yl)-1-oxoisoindolin-5-yl)carbamoyl)phenoxy) methyl)azetidine-1-carboxylate A mixture of 4-((1-(tert-butoxycarbonyl) azetidin-3-yl) methoxy)benzoic acid (122 mg, 0.397 mmol), 3-(5-amino-1-oxoisoindolin-2-yl) piperidine-2,6-dione (intermediate 2) (86 mg, 0.332 mmol), HATU (151 mg, 0.398 mmol), and N,N-diisopropylethylamine (0.232 mL, 1.327 mmol) was stirred at rt for 7 days. The mixture was diluted with ethyl acetate (60 mL), washed with water (20 mL), saturated NaHCO$_3$ solution (20 mL), and dried over anhydrous MgSO₄. The desired product, tert-butyl 3-((4-((2-(2,6-dioxopiperidin-3-yl)-1-oxoisoindolin-5-yl)carbamoyl)phenoxy)methyl)azetidine-1-carboxylate (102 mg, 0.186 mmol, 56.1% yield) was isolated as a white solid by ISCO chromatography (40 g silica gel, solid loading, 0-10% MeOH/CH₂Cl₂). LCMS (M+H)⁺=548.8. ¹H NMR (400 MHZ, DMSO-d₆) δ 10.98 (s, 1H), 10.40 (s, 1H), 8.15 (d, J=1.7 Hz, 1H), 8.05-7.94 (m, 2H), 7.84 (dd, J=8.4, 1.8 Hz, 1H), 7.71 (d, J=8.3 Hz, 1H), 7.11 (d, J=8.9 Hz, 2H), 5.11 (dd, J=13.2, 5.1 Hz, 1H), 4.47 (d, J=17.3 Hz, 1H), 4.33 (d, J=17.3 Hz, 1H), 4.23 (d, J=6.4 Hz, 2H), 4.07-3.92 (s, 2H), 3.78-3.63 (m, 2H), 3.07-2.84 (m, 2H), 2.66-2.57 (m, 1H), 2.44-2.36 (m, 1H), 2.13-1.92 (m, 1H), 1.40 (s, 9H).

Step 4. 4-(Azetidin-3-ylmethoxy)-N-(2-(2,6-dioxopiperidin-3-yl)-1-oxoisoindolin-5-yl)benzamide To a solution of tert-butyl 3-((4-((2-(2,6-dioxopiperidin-3-yl)-1-oxoisoindolin-5-yl)carbamoyl)phenoxy)methyl)azetidine-1-carboxylate (102 mg, 0.186 mmol) in CH₂Cl₂ (5 mL) at rt was added 4 M hydrogen chloride in 1,4-dioxane (5 mL, 20.00 mmol) over 1 min. The mixture was stirred at rt for 1 h, and then concentrated under vacuum to dryness to provide 4-(azetidin-3-ylmethoxy)-N-(2-(2,6-dioxopiperidin-3-yl)-1-oxoisoindolin-5-yl)benzamide, HCl (129 mg, 0.186 mmol, 100% yield) as a white solid (ring opening product was also observed). LCMS (M+H)⁺=448.9.

Step 5. 4-((1-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-1-oxoisoindolin-5-yl)benzamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (25 mg, 0.033 mmol), 4-(azetidin-3-ylmethoxy)-N-(2-(2,6-dioxopiperidin-3-yl)-1-oxoisoindolin-5-yl)benzamide, HCl (20 mg, 0.029 mmol), BOP (20.43 mg, 0.046 mmol), and N,N-diisopropylethylamine (0.025 mL, 0.144 mmol) in DMF (1 mL) was stirred at rt for 2 h. The crude material was purified via preparative LC with the following conditions: Column: Phenomenex Luna Axia C18, 21.2×100 mm, 5-µm particles; Mobile Phase A: 5:95 acetonitrile:water with 0.1% TFA; Mobile Phase B: 95:5 acetonitrile:water with 0.1% TFA; Gradient: 30-100% B over 10 minutes, then a 2-minute hold at 100% B; Flow: 20 mL/min. Fractions containing the desired product were combined and dried via centrifugal evaporation to give provided the desired product, 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-1-oxoisoindolin-5-yl)benzamide (15 mg, 0.013 mmol, 43.4% yield), as a white solid. LCMS (M+H)⁺=1197.2.

Step 6. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-1-oxoisoindolin-5-yl)benzamide A mixture of 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-1-oxoisoindolin-5-yl)benzamide (25 mg, 0.021 mmol) in 70% acetic acid (3 mL) was heated at 75° C. for 17 h. The solution was diluted with methanol (4 mL), divided into 2 portions, and injected to prep. HPLC. The corrected fractions were combined, concentrated under vacuum, to give a product. This product was diluted with saturated aq. NaHCO₃ and extracted with dichloromethane (2×50 mL). The combined extract was dried over anhydrous Na₂SO₄. Removal of the solvent under vacuum provided the desired product, 4-((1-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-1-oxoisoindolin-5-yl)benzamide (21.3 mg, 0.019 mmol, 90% yield), as a white solid. LCMS (M+H)⁺=1109.1. ¹H NMR (400 MHZ, DMSO-d₆) δ 10.98 (s, 1H), 10.39 (d, J=3.4 Hz, 1H), 9.14 (d, J=4.4 Hz, 1H), 8.15 (s, 1H), 8.11-7.61 (m, 8H), 6.99 (t, J=8.9 Hz, 3H), 5.48 (d, J=6.0 Hz, 1H), 5.20 (d, J=10.7 Hz, 1H), 5.11 (dd, J=13.1, 5.1 Hz, 1H), 4.88-4.62 (m, 2H), 4.54-4.43 (m, 2H), 4.34 (d, J=17.4 Hz, 1H), 4.13-3.98 (m, 2H), 3.99-3.57 (m, 6H), 3.51-3.35 (m, 2H), 3.05-2.75 (m, 2H), 2.65-2.57 (m, 1H), 2.46-2.28 (m, 4H), 2.11-1.87 (m, 1H). hGal-3 IC₅₀=0.056µM; hCRBN IC₅₀=0.601 µM.

Example 8. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)oxy)-N-(2-(2,6-dioxopiperidin-3-yl)-1-oxoisoindolin-5-yl)benzamide

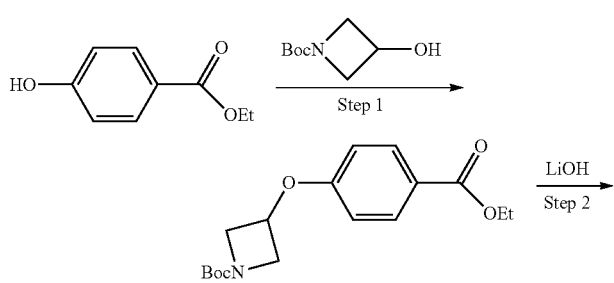

-continued
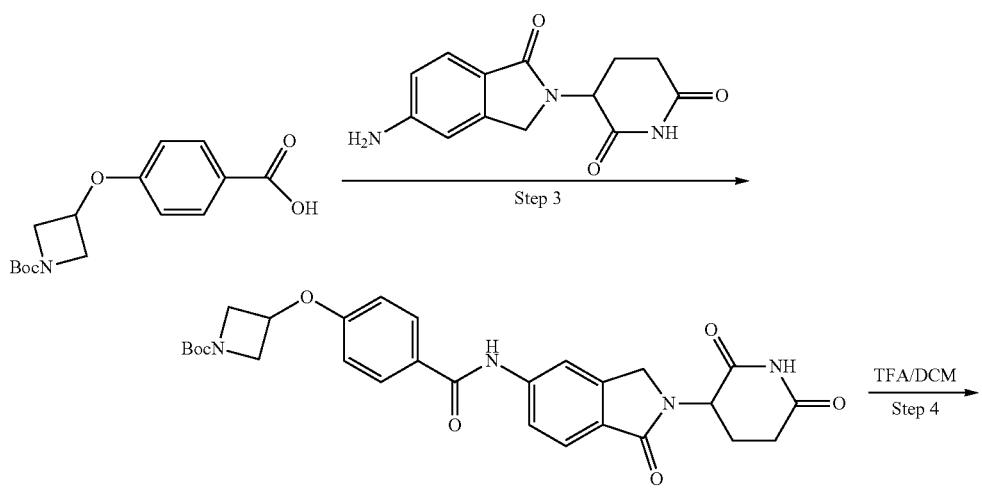
Step 3
TFA/DCM
Step 4
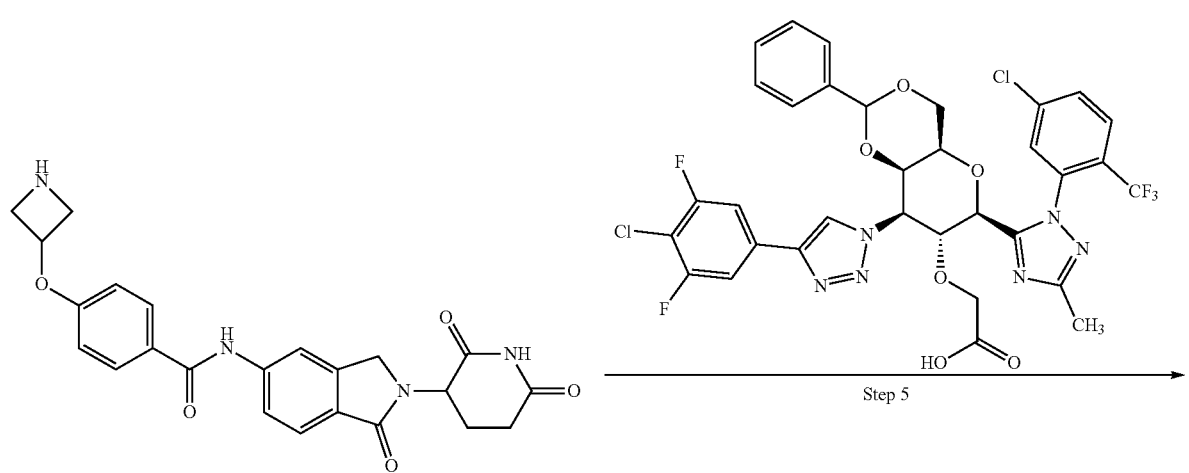
Step 5
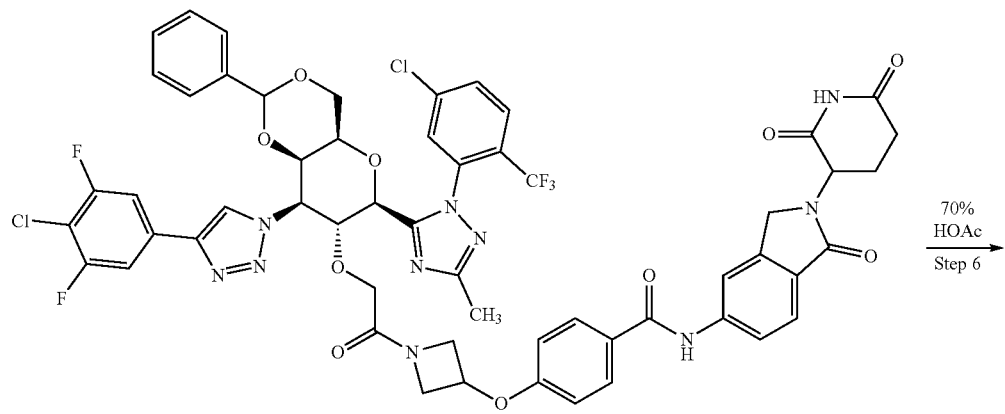
70% HOAc
Step 6

-continued

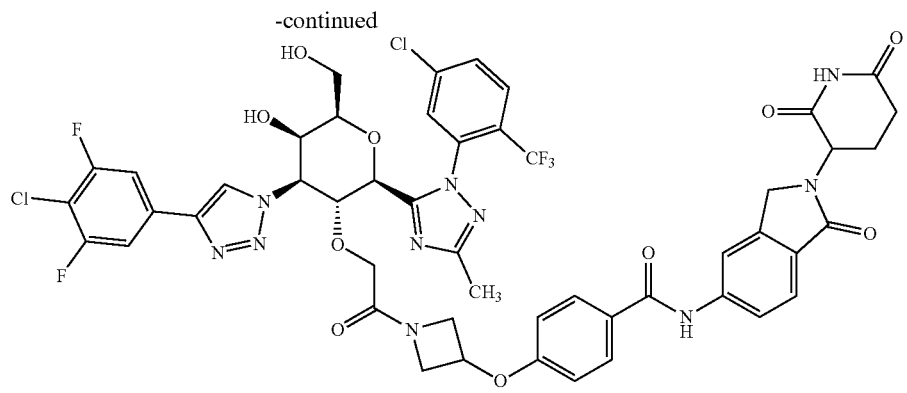

Example 8

Step 1. tert-Butyl 3-(4-(ethoxycarbonyl) phenoxy) azetidine-1-carboxylate

To a mixture of ethyl 4-hydroxybenzoate (0.35 g, 2.106 mmol), tert-butyl 3-hydroxyazetidine-1-carboxylate (0.456 g, 2.63 mmol), and triphenylphosphine (0.829 g, 3.16 mmol) in Toluene (12 mL) at rt was added diisopropyl azodicarboxylate (DIAD) (0.622 mL, 3.16 mmol) over 1 min. The resulting solution was heated at 105° C. for 16 h. Upon cooling to rt, the reaction solution was diluted with ethyl acetate (50 mL) and silica gel (5 g) was added. The volatiles were removed under vacuum. The residue was subjected to ISCO chromatography (80 g silica gel, 0-35% ethyl acetate/hexane) to provide tert-butyl 3-(4-(ethoxycarbonyl) phenoxy) azetidine-1-carboxylate (637 mg, 1.982 mmol, 94% yield) as viscous oil. $^1$H NMR (400 MHZ, chloroform-d) δ 8.15-7.74 (m, 2H), 6.95-6.58 (m, 2H), 4.93 (tt, J=6.4, 4.1 Hz, 1H), 4.40-4.28 (m, 4H), 4.01 (ddd, J=9.7, 4.1, 1.1 Hz, 2H), 1.45 (s, 9H), 1.38 (t, J=7.1 Hz, 3H).

Step 2. 4-((1-(tert-Butoxycarbonyl) azetidin-3-yl) oxy)benzoic acid

To a solution of tert-butyl 3-(4-(ethoxycarbonyl) phenoxy) azetidine-1-carboxylate (637 mg, 1.982 mmol) in tetrahydrofuran (20 mL) and methanol (5 mL) at rt was added lithium hydroxide (285 mg, 11.9 mmol) in water (5 mL) over 1 min. The mixture was stirred at 50° C. for 16 h, and then concentrated under vacuum to a volume of approximately 5 mL. The residue was diluted with water (15 mL) and acidified with 1 N HCl to pH=5-6. The precipitating product, 4-((1-(tert-butoxycarbonyl) azetidin-3-yl)oxy)benzoic acid (516 mg, 1.759 mmol, 89% yield), was collected as a white solid by suction filtration and dried at 50° C. under vacuum. The product was used for next step without further purification.

Step 3. tert-Butyl 3-(4-((2-(2,6-dioxopiperidin-3-yl)-1-oxoisoindolin-5-yl)carbamoyl)phenoxy)azetidine-1-carboxylate A mixture of 4-((1-(tert-butoxycarbonyl) azetidin-3-yl) oxy)benzoic acid (122 mg, 0.416 mmol), 3-(5-amino-1-oxoisoindolin-2-yl) piperidine-2,6-dione (86 mg, 0.332 mmol), HATU (151 mg, 0.398 mmol), and N,N-diisopropylethylamine (0.232 mL, 1.327 mmol) in DMF (3 mL) was stirred at rt for 7 days. The mixture was diluted with ethyl acetate (60 mL), washed with water (2×20 mL) saturated NaHCO$_3$ solution (20 mL), and dried over anhydrous MgSO$_4$. The desired product, tert-butyl 3-(4-((2-(2,6-dioxopiperidin-3-yl)-1-oxoisoindolin-5-yl)carbamoyl)phenoxy)azetidine-1-carboxylate (110 mg, 0.206 mmol, 62.0% yield), was isolated as a white solid by ISCO chromatography (40 g silica gel, solid loading, 0-10% MeOH/CH$_2$Cl$_2$). LCMS (M+H)$^+$=534.8.

Step 4. 4-(Azetidin-3-yloxy)-N-(2-(2,6-dioxopiperidin-3-yl)-1-oxoisoindolin-5-yl)benzamide A mixture of tert-butyl 3-(4-((2-(2,6-dioxopiperidin-3-yl)-1-oxoisoindolin-5-yl)carbamoyl)phenoxy)azetidine-1-carboxylate (110 mg, 0.206 mmol) in CH$_2$Cl$_2$ (2 mL) and TFA (2 mL) was stirred at RT for 2 h. Solvent was evaporated to give 4-(azetidin-3-yloxy)-N-(2-(2,6-dioxopiperidin-3-yl)-1-oxoisoindolin-5-yl)benzamide, TFA (113 mg, 0.206 mmol, 100% yield) as viscous oil. The product was used for the next step without further purification.

Step 5. 4-((1-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)oxy)-N-(2-(2,6-dioxopiperidin-3-yl)-1-oxoisoindolin-5-yl) benzamide A mixture of 4-(azetidin-3-yloxy)-N-(2-(2,6-dioxopiperidin-3-yl)-1-oxoisoindolin-5-yl)benzamide, TFA (34 mg, 0.062 mmol), 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (48 mg, 0.063 mmol), BOP (43.9 mg, 0.099 mmol) and N,N-diisopropylethylamine (0.054 mL, 0.310 mmol) in DMF (1.5 mL) was stirred at rt for 2 h. The crude material was purified via preparative HPLC with the following conditions:

Column: Phenomenex Luna Axia C18, 30×100 mm, 5-μm particles; Mobile Phase A: 5:95 acetonitrile:water with 0.1% TFA; Mobile Phase B: 95:5 acetonitrile:water with 0.1% TFA; Gradient: 25-100% B over 10 minutes, then a 2-minute hold at 100% B; Flow: 20 mL/min. Fractions containing the desired product were combined and dried via centrifugal evaporation to provide the desired product, 4-((1-(2-(((4aR, 6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)oxy)-N-(2-(2,6-dioxopiperidin-3-yl)-1-oxoisoindolin-5-yl)benzamide (58 mg, 0.049 mmol, 79% yield), as a white solid. LCMS (M+H)$^+$=1183.2.

Step 6. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)oxy)-N-(2-(2,6-dioxopiperidin-3-yl)-1-oxoisoindolin-5-yl)benzamide A mixture of 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)oxy)-N-(2-(2,6-dioxopiperidin-3-yl)-1-oxoisoindolin-5-yl)benzamide (58 mg, 0.049 mmol) in 70% acetic acid (3 mL) was heated at 70° C. for 17 h. The solution was diluted with methanol (3 mL), divided into 2 portions, and injected to preparative HPLC. The corrected fractions were combined, concentrated under vacuum to give a product. The product was dissolved in 100 ml DCM and washed with saturated NaHCO$_3$ solution (5 ml). The organic layer was separated, dried over MgSO$_4$ and concentrated to give desired product, 4-((1-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)oxy)-N-(2-(2,6-dioxopiperidin-3-yl)-1-oxoisoindolin-5-yl)benzamide (26 mg, 0.023 mmol, 46.0% yield), as a white solid. LCMS (M+H)$^+$=1095.0. $^1$H NMR (400 MHZ, DMSO-d$_6$) δ 10.98 (s, 1H), 10.42 (d, J=2.3 Hz, 1H), 9.14 (d, J=15.3 Hz, 1H), 8.15 (s, 1H), 8.06 (dd, J=8.8, 6.5 Hz, 1H), 8.02-7.93 (m, 3H), 7.93-7.79 (m, 3H), 7.71 (d, J=8.3 Hz, 1H), 6.92-6.77 (m, 2H), 5.47 (t, J=6.3 Hz, 1H), 5.21 (d, J=10.7 Hz, 1H), 5.11 (dd, J=13.2, 5.1 Hz, 1H), 5.02-4.91 (m, 1H), 4.86-4.73 (m, 1H), 4.73-4.64 (m, 1H), 4.55-4.42 (m, 2H), 4.34 (d, J=17.4 Hz, 1H), 4.24-3.99 (m, 2H), 3.97-3.55 (m, 6H), 3.50-3.39 (m, 2H), 2.92-2.83 (m, 1H), 2.76-2.57 (m, 1H), 2.44-2.30 (m, 4H), 2.17-1.89 (m, 1H). hGal-3 IC$_{50}$=0.048 μM; hCRBN IC$_{50}$ μM=1.42 μM.

Example 9. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(1-methyl-2,6-dioxopiperidin-3-yl)-1-oxoisoindolin-5-yl)benzamide

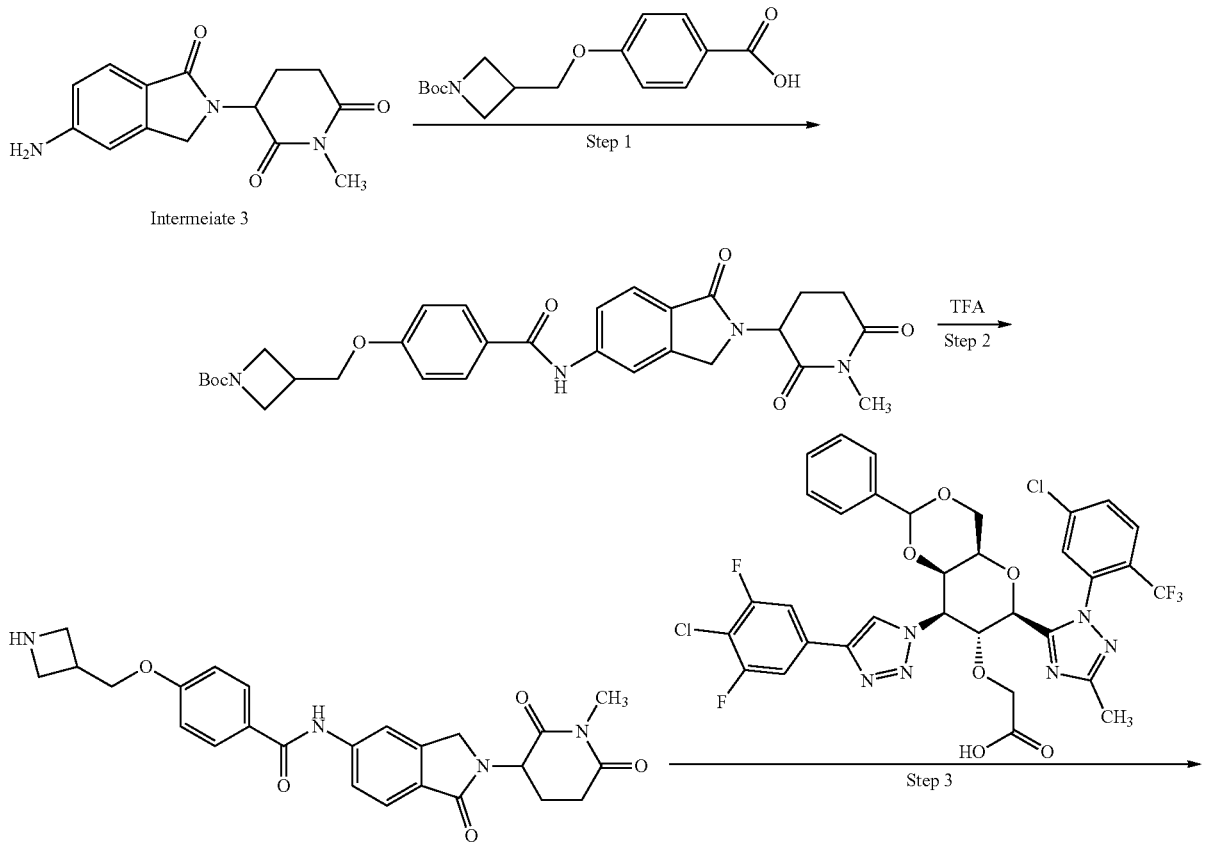

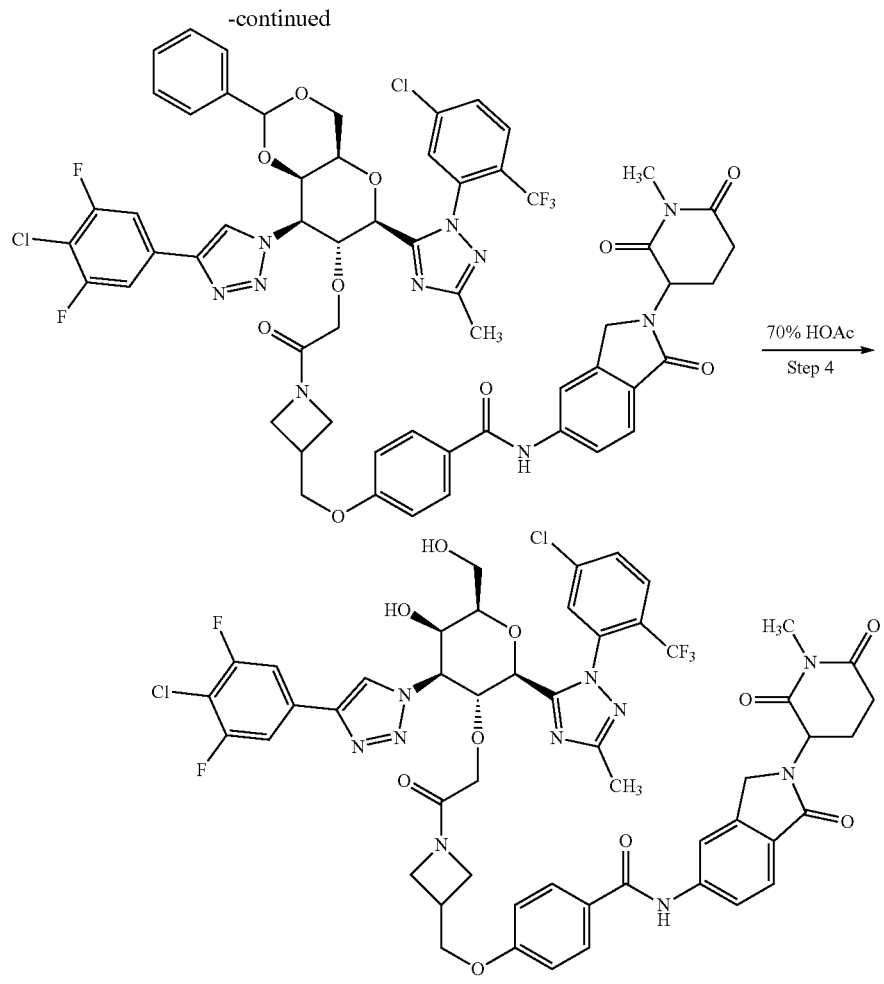

Example 9

Step 1. tert-Butyl 3-(4-((2-(2,6-dioxopiperidin-3-yl)-1-oxoisoindolin-5-yl)carbamoyl)phenoxy)azetidine-1-carboxylate A mixture of 4-((1-(tert-butoxycarbonyl) azetidin-3-yl)methoxy)benzoic acid (98 mg, 0.319 mmol), 3-(5-amino-1-oxoisoindolin-2-yl)-1-methylpiperidine-2,6-dione (105 mg, 0.384 mmol, intermediate 3), HATU (145 mg, 0.383 mmol), and N,N-diisopropylethylamine (0.223 mL, 1.275 mmol) in DMF (3 mL) was stirred at rt for 5 days. The crude material was purified via preparative HPLC with the following conditions: Column: Sunfire C18, 30×100 mm, OBD 5-µm particles; Mobile Phase A: 5:95 acetonitrile:water with 0.1% TFA; Mobile Phase B: 95:5 acetonitrile:water with 0.1% TFA; Gradient: 5-100% B over 10 minutes, then a 2-minute hold at 100% B; Flow: 40 mL/min. The fractions containing the desired product were combined and dried via centrifugal evaporation to provide the desired product, tert-butyl 3-((4-((2-(1-methyl-2,6-dioxopiperidin-3-yl)-1-oxoisoindolin-5-yl)carbamoyl)phenoxy)methyl)azetidine-1-carboxylate (44 mg, 0.078 mmol, 24.53% yield). LCMS (M+H)$^+$=562.8. $^1$H NMR (400 MHz, DMSO-d$_6$) § 10.40 (s, 1H), 8.15 (d, J=2.0 Hz, 1H), 8.05-7.93 (m, 2H), 7.85 (dd, J=8.3, 1.8 Hz, 1H), 7.71 (d, J=8.3 Hz, 1H), 7.11 (d, J=8.9 Hz, 2H), 5.18 (dd, J=13.4, 5.1 Hz, 1H), 4.47 (d, J=17.4 Hz, 1H), 4.32 (d, J=17.2 Hz, 1H), 4.23 (d, J=6.5 Hz, 2H), 4.05-3.92 (m, 2H), 3.79-3.61 (m, 2H), 3.47 (bs, 1H), 3.10-2.92 (m, 4H), 2.88-2.70 (m, 1H), 2.47-2.29 (m, 1H), 2.06-1.96 (m, 1H), 1.40 (s, 9H).

Step 2. 4-(Azetidin-3-ylmethoxy)-N-(2-(1-methyl-2, 6-dioxopiperidin-3-yl)-1-oxoisoindolin-5-yl)benzamide A mixture of tert-butyl 3-(4-((2-(2,6-dioxopiperidin-3-yl)-1-oxoisoindolin-5-yl)carbamoyl)phenoxy)azetidine-1-carboxylate (44 mg, 0.078 mmol) in CH$_2$Cl$_2$ (2 mL) and TFA (2 mL) was stirred at RT for 2 h. Solvent was evaporated to give 4-(azetidin-3-ylmethoxy)-N-(2-(1-methyl-2,6-dioxopiperidin-3-yl)-1-oxoisoindolin-5-yl)benzamide, TFA (45 mg, 0.078 mmol) as viscous oil. LCMS (M+H)$^+$=462.9. The product was used for next step without further purification.

Step 3. 4-((1-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(1-methyl-2,6-dioxopiperidin-3-yl)-1-oxoisoindolin-5-yl)benzamide A mixture of 4-(azetidin-3-ylmethoxy)-N-(2-(1-methyl-2,6-dioxopiperidin-3-yl)-1-oxoisoindolin-5-yl)benzamide, TFA (36 mg, 0.062 mmol), 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (48 mg, 0.063 mmol), BOP (44.3 mg, 0.100 mmol) and N,N-diisopropylethylamine (0.055 mL, 0.313 mmol) in DMF (1.5 mL) was stirred at rt for 2 h. The crude material was purified via preparative HPLC with the following conditions: Column: Phenomenex Luna Axia C18, 30×100 mm, 5-μm particles; Mobile Phase A: 5:95 acetonitrile:water with 0.1% TFA; Mobile Phase B: 95:5 acetonitrile:water with 0.1% TFA; Gradient: 35-100% B over 10 minutes, then a 2-minute hold at 100% B; Flow: 40 mL/min. The fractions containing the desired product were combined and dried via centrifugal evaporation to provide the desired product, 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(1-methyl-2,6-dioxopiperidin-3-yl)-1-oxoisoindolin-5-yl)benzamide (65 mg, 0.054 mmol, 86% yield) as white solid. LCMS (M+H)$^+$=1211.1.

Step 4. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(1-methyl-2,6-dioxopiperidin-3-yl)-1-oxoisoindolin-5-yl)benzamide A mixture of 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(1-methyl-2,6-dioxopiperidin-3-yl)-1-oxoisoindolin-5-yl)benzamide (65 mg, 0.054 mmol) in 70% acetic acid (4 mL) was heated at 70° C. for 17 h. The solvent was evaporated. The crude product was purified via preparative HPLC with the following conditions: Column: XBridge C18, 200 mm×19 mm, 5-μm articles; Mobile Phase A: 5:95 acetonitrile:water with 10-mM ammonium acetate; Mobile Phase B: 95:5 acetonitrile:water with 10-mM ammonium acetate; Gradient: a 0-minute hold at 27% B, 27-67% B over 22 minutes, then a 0-minute hold at 100% B; Flow Rate: 20 mL/min; Column Temperature: 25 C. Fractions containing the desired product were combined and dried via centrifugal evaporation to provide the desired product, 4-((1-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(1-methyl-2,6-dioxopiperidin-3-yl)-1-oxoisoindolin-5-yl)benzamide (33.6 mg, 0.030 mmol, 55.1% yield) as white solid. LCMS (M+H)$^+$=1123.0. $^1$H NMR (500 MHz, DMSO-$d_6$) δ 10.40 (d, J=5.0 Hz, 1H), 9.13 (d, J=5.9 Hz, 1H), 8.16 (s, 1H), 8.05 (dd, J=15.2, 8.6 Hz, 1H), 8.02-7.90 (m, 4H), 7.89-7.79 (m, 3H), 7.73 (d, J=8.3 Hz, 1H), 6.99 (dd, J=12.8, 8.7 Hz, 2H), 5.49 (d, J=5.8 Hz, 1H), 5.26-5.11 (m, 2H), 4.89-4.67 (m, 2H), 4.57-4.42 (m, 2H), 4.34 (d, J=17.2 Hz, 1H), 4.14-3.96 (m, 2H), 3.97-3.57 (m, 7H), 3.51-3.37 (m, 2H), 3.02 (s, 3H), 3.05-2.93 (m, 1H), 2.95-2.71 (m, 2H), 2.46-2.33 (m, 1H), 2.36 (s, 3H), 2.14-1.96 (m, 1H). hGal-3 IC$_{50}$=0.085 μM; hCRBN IC$_{50}$=8.95 μM.

Example 10. 5-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)ethoxy)-N-(2-(2,6-dioxopiperidin-3-yl)-1-oxoisoindolin-5-yl)picolinamide

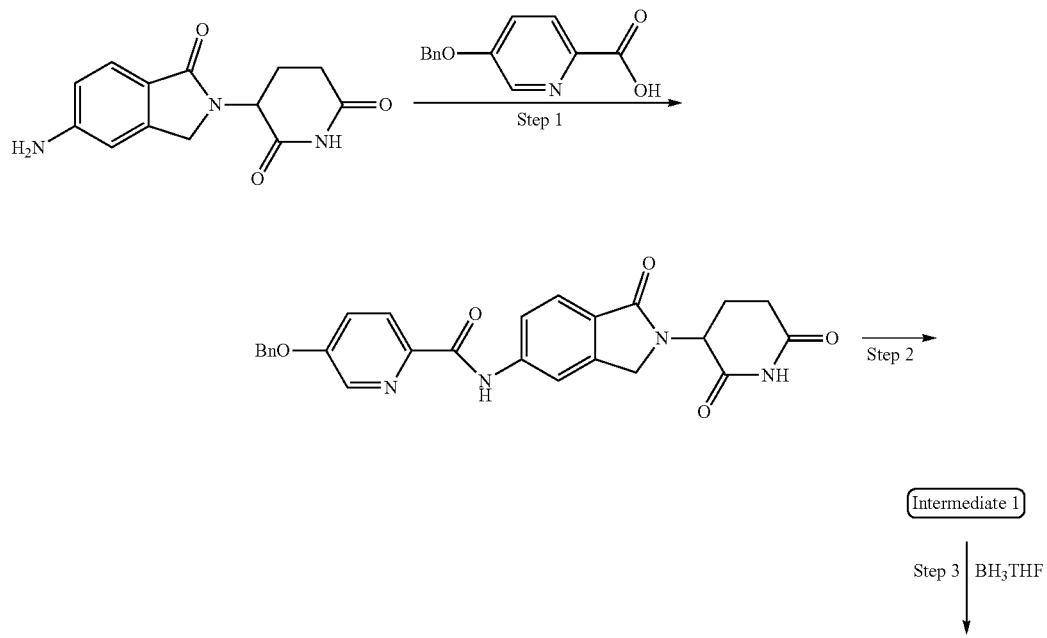

-continued
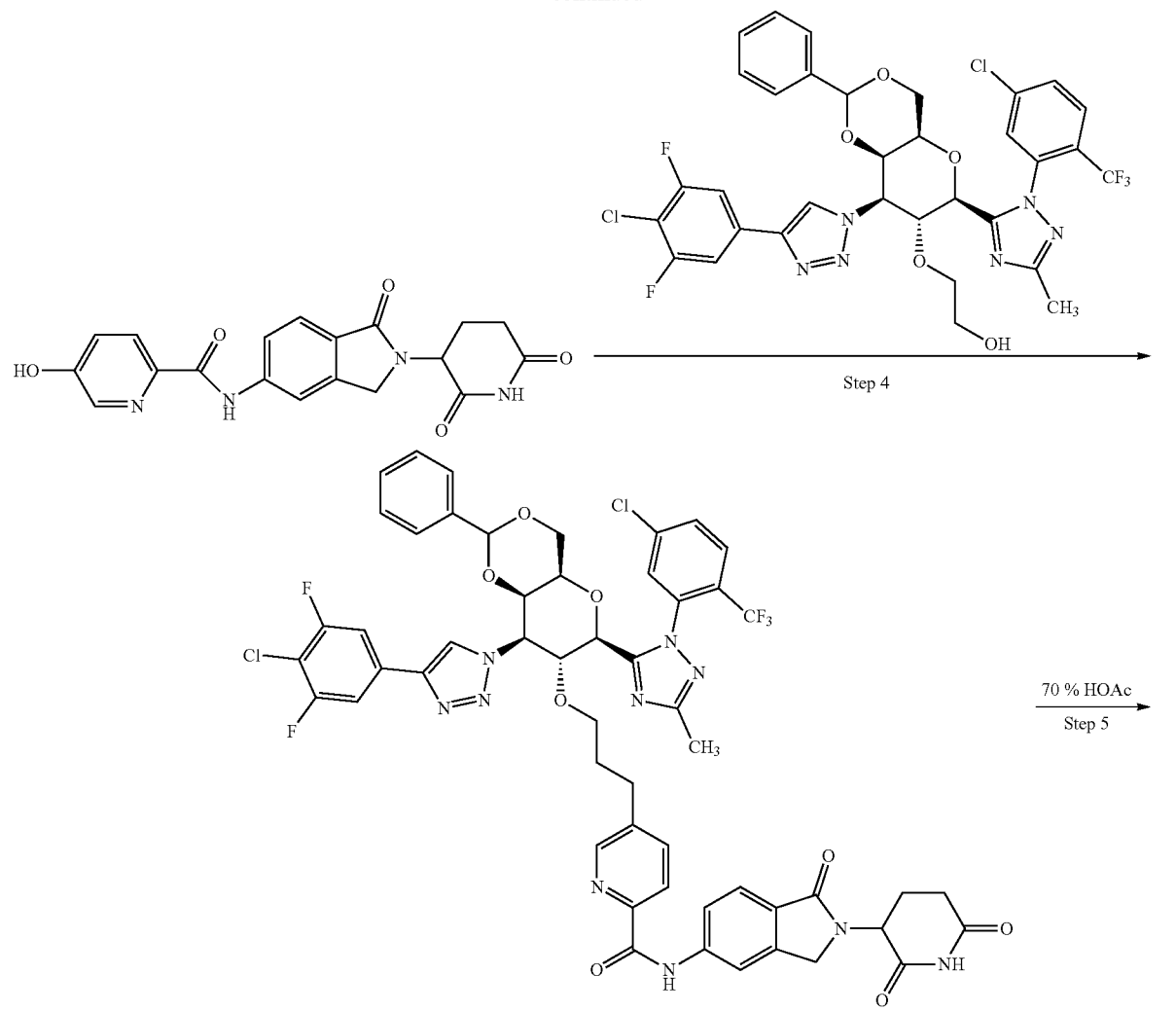
Step 4
70 % HOAc
Step 5
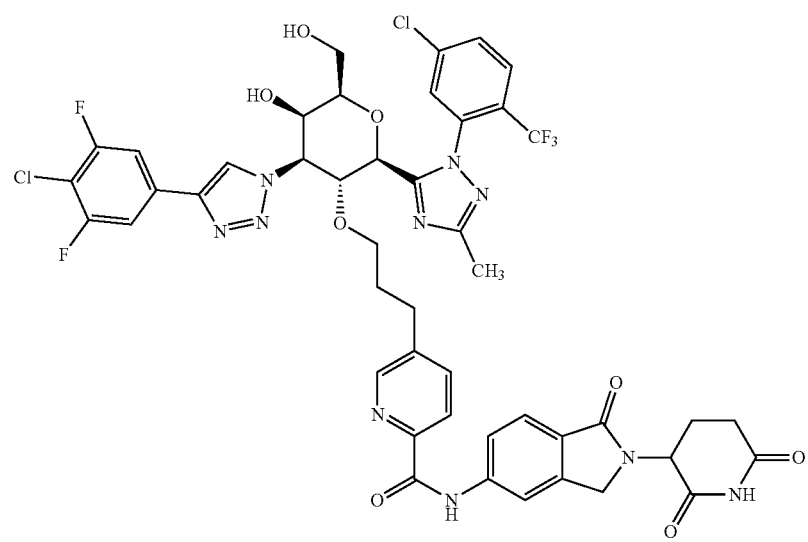
Example 10

Step 1. 5-(Benzyloxy)-N-(2-(2,6-dioxopiperidin-3-yl)-1-oxoisoindolin-5-yl)picolinamide A mixture of 5-(benzyloxy) picolinic acid (85 mg, 0.371 mmol), 3-(5-amino-1-oxoisoindolin-2-yl) piperidine-2,6-dione (95 mg, 0.366 mmol), HATU (169 mg, 0.445 mmol), and N,N-diisopropylethylamine (0.259 mL, 1.483 mmol) in DMF (2 mL) was stirred at rt over a weekend. Water (3 mL) was added. The insoluble product, 5-(benzyloxy)-N-(2-(2,6-dioxopiperidin-3-yl)-1-oxoisoindolin-5-yl)picolinamide (127 mg, 0.270 mmol, 72.8% yield) was collected as beige solid via filtration and dried under vacuum. LCMS (M+H)$^+$=470.8.

Step 2. N-(2-(2,6-Dioxopiperidin-3-yl)-1-oxoisoindolin-5-yl)-5-hydroxypicolinamide A mixture of 5-(benzyloxy)-N-(2-(2,6-dioxopiperidin-3-yl)-1-oxoisoindolin-5-yl)picolinamide (127 mg, 0.270 mmol) and 10% Pd/C (28.7 mg, 0.027 mmol) in methanol (18 mL) and tetrahydrofuran (5 mL) was stirred under H$_2$, provided with a H$_2$ balloon, at rt for 6 h. After the H$_2$ balloon was removed, the reaction mixture was purged with N$_2$ and heated to reflux. The catalyst was removed by filtration when the mixture was hot. The filtrate was concentrated under vacuum to dryness. The residue was dried at 50° C. under vacuum to provide the desired product, N-(2-(2,6-dioxopiperidin-3-yl)-1-oxoisoindolin-5-yl)-5-hydroxypicolinamide (70 mg, 0.018 mmol, 70% yield), as a light yellow solid. LCMS (M+H)$^+$=380.8.

Step 3. 2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy) ethan-1-ol To a solution of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy) acetic acid (intermediated 1) (100 mg, 0.130 mmol, in THF (0.8 mL) at rt was added borane tetrahydrofuran complex (1 M in THF, 0.860 mL, 0.860 mmol). The reaction was stirred at rt for 4 h. MeOH was added dropwise to quench the reaction until bubbling ceased. The reaction was stirred for 60 min and then concentrated under vacuum. The residue was diluted with EtOAc, washed with brine, dried over MgSO$_4$, and concentrated. The crude was purified by a silica gel flash column and eluted by 0-90% EtOAc-Hexane to afford 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy) ethan-1-ol (97 mg, 0.129 mmol, 99% yield) as foam solid.

Step 4. 5-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)ethoxy)-N-(2-(2,6-dioxopiperidin-3-yl)-1-oxoisoindolin-5-yl)picolinamide To a mixture of N-(2-(2,6-dioxopiperidin-3-yl)-1-oxoisoindolin-5-yl)-5-hydroxypicolinamide (38.9 mg, 0.102 mmol), 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy) ethan-1-ol (77.00 mg, 0.102 mmol) and triphenylphosphine (40.2 mg, 0.153 mmol) in THF (6 mL) at rt was added DIAD (0.030 mL, 0.153 mmol) over 1 min. The resulting solution was stirred at rt for 2.5 h. The reaction mixture was heated at 70° C. for 0.5 h. The volatiles were removed under vacuum. The residue was subjected to Preparative HPLC purification with the following condition: Column: Phenomenex Luna Axia C18, 30×100 mm, 5-µm particles; Mobile Phase A: 5:95 acetonitrile:water with 0.1% TFA; Mobile Phase B: 95:5 acetonitrile:water with 0.1% TFA; Gradient: 45-100% B over 10 minutes, then a 2-minute hold at 100% B; Flow: 40 mL/min. Fractions containing the desired product were combined and dried via centrifugal evaporation to provide the desired product, 5-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)ethoxy)-N-(2-(2,6-dioxopiperidin-3-yl)-1-oxoisoindolin-5-yl)picolinamide (16.5 mg, 0.015 mmol, 14.5% yield), as white solid. LCMS (M+H)$^+$=1115.0.

Step 5. 5-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)ethoxy)-N-(2-(2,6-dioxopiperidin-3-yl)-1-oxoisoindolin-5-yl)picolinamide A mixture of 5-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)ethoxy)-N-(2-(2,6-dioxopiperidin-3-yl)-1-oxoisoindolin-5-yl)picolinamide (18 mg, 0.016 mmol) in 70% acetic acid (3 mL) was heated at 70° C. for 17 h. The solution was diluted with methanol and subjected to prep. HPLC purification with the following condition: Column: Phenomenex Luna Axia C18, 21.2×100 mm, 5-µm particles; Mobile Phase A: 5:95 acetonitrile:water with 0.1% TFA; Mobile Phase B: 95:5 acetonitrile:water with 0.1% TFA; Gradient: 15-100% B over 16 minutes, then a 2-minute hold at 100% B; Flow: 20 mL/min. Fractions containing the desired product were combined and dried via centrifugal evaporation to provide the desired product. This product was diluted with saturated aq. NaHCO$_3$ (5 mL) and extracted with dichloromethane (2×30 mL). The combined extract was dried over anhydrous Na$_2$SO$_4$. Removal of the solvent under vacuum provided the desired product, 5-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)ethoxy)-N-(2-(2,6-dioxopiperidin-3-yl)-1-oxoisoindolin-5-yl)picolinamide (12.0 mg, 0.011 mmol, 71% yield), as white solid. LCMS (M+H)$^+$=1127.0. $^1$H NMR (400 MHZ, DMSO-d$_6$) δ 10.98 (s, 1H), 10.63 (s, 1H), 9.14 (s, 1H), 8.24 (d, J=1.8 Hz, 1H), 8.07 (d, J=8.7 Hz, 1H), 8.02-7.89 (m, 4H), 7.83-7.64 (m, 4H), 7.25 (dd, J=8.9, 2.9 Hz, 1H), 5.52 (d, J=5.9 Hz, 1H), 5.16 (dd, J=10.7, 2.9 Hz, 1H), 5.11 (dd, J=13.3, 5.1 Hz, 1H), 4.83 (t, J=9.8 Hz, 1H), 4.71 (t, J=5.8 Hz, 1H), 4.56-4.39 (m, 2H), 4.33 (d, J=17.3 Hz, 1H), 3.95-3.88 (m, 2H), 3.82-3.73 (m, 1H), 3.71 (t, J=6.3 Hz, 1H), 3.67-3.57 (m, 1H), 3.54-3.39 (m, 3H), 3.03-2.84 (m, 1H), 2.65-2.57 (m, 1H), 2.44-2.38 (m, 1H), 2.36 (s, 3H), 2.11-1.84 (m, 1H). hGal-3 IC$_{50}$=0.074 µM; hCRBN IC$_{50}$=0.214 µM.

Example 11. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-3-oxoisoindolin-5-yl)benzamide
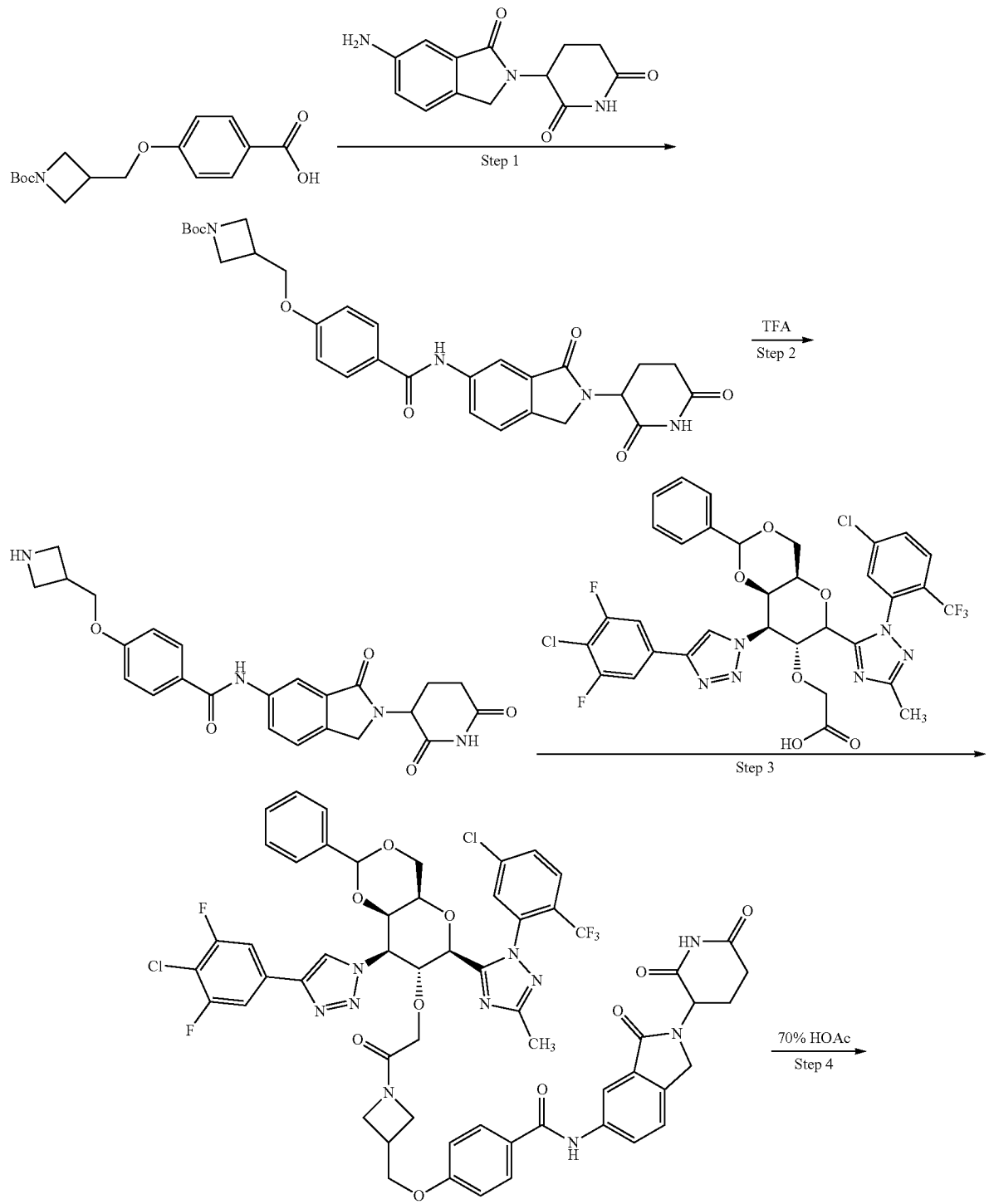

-continued

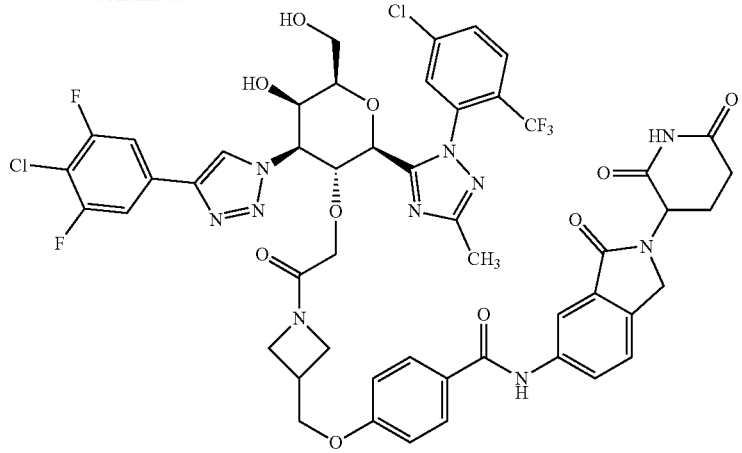

Example 11

Step 1. tert-Butyl 3-((4-((2-(2,6-dioxopiperidin-3-yl)-3-oxoisoindolin-5-yl)carbamoyl)phenoxy)methyl)azetidine-1-carboxylate A mixture of 4-((1-(tert-butoxycarbonyl) azetidin-3-yl)methoxy)benzoic acid (65.0 mg, 0.211 mmol), 3-(6-amino-1-oxoisoindolin-2-yl) piperidine-2,6-dione (50 mg, 0.193 mmol, Intermediate 4), HATU (88 mg, 0.231 mmol), and N,N-diisopropylethylamine (0.135 mL, 0.77 mmol) in DMF (2 mL) was stirred at rt for 16 h. The crude material was purified via preparative HPLC with the following conditions: Column: Phenomenex Luna Axia C18, 30×100 mm, 5-µm particles; Mobile Phase A: 5:95 acetonitrile:water with 0.1% TFA; Mobile Phase B: 95:5 acetonitrile:water with 0.1% TFA; Gradient: 15-100% B over 10 minutes, then a 2-minute hold at 100% B; Flow: 40 mL/min. Fractions containing the desired product were combined and dried via centrifugal evaporation to give provided the desired product, tert-butyl 3-((4-((2-(2,6-dioxopiperidin-3-yl)-3-oxoisoindolin-5-yl)carbamoyl)phenoxy)methyl)azetidine-1-carboxylate (77 mg, 0.140 mmol, 72.8% yield), as a white solid. LCMS (M+H)+=548.8.

Step 2. 4-(Azetidin-3-ylmethoxy)-N-(2-(2,6-dioxopiperidin-3-yl)-3-oxoisoindolin-5-yl)benzamide To a solution of tert-butyl 3-((4-((2-(2,6-dioxopiperidin-3-yl)-3-oxoisoindolin-5-yl)carbamoyl)phenoxy)methyl)azetidine-1-carboxylate (42 mg, 0.077 mmol) in $CH_2Cl_2$ (2 mL) and TFA (2 mL) was stirred at RT rt for 2 h. Solvent was evaporated to give 4-(azetidin-3-ylmethoxy)-N-(2-(2,6-dioxopiperidin-3-yl)-3-oxoisoindolin-5-yl)benzamide, TFA (43 mg, 0.077 mmol, 100% yield) as viscous oil. LCMS (M+H)+=449.8.

Step 3. 4-((1-(2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-3-oxoisoindolin-5-yl)benzamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (48 mg, 0.063 mmol), 4-(azetidin-3-ylmethoxy)-N-(2-(2,6-dioxopiperidin-3-yl)-3-oxoisoindolin-5-yl)benzamide, TFA (43.1 mg, 0.077 mmol), BOP (44.3 mg, 0.100 mmol), and N,N-diisopropylethylamine (0.055 mL, 0.313 mmol) in DMF (1.5 mL) was stirred at rt for 2 h. The crude material was purified via preparative HPLC with the following conditions: Column: Phenomenex Luna Axia C18, 30×100 mm, 5-µm particles; Mobile Phase A: 5:95 acetonitrile:water with 0.1% TFA; Mobile Phase B: 95:5 acetonitrile:water with 0.1% TFA; Gradient: 30-100% B over 10 minutes, then a 2-minute hold at 100% B; Flow: 40 mL/min. Fractions containing the desired product were combined and dried via centrifugal evaporation to give the desired product, 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-3-oxoisoindolin-5-yl)benzamide (61 mg, 0.051 mmol, 81% yield), as a white solid. LCMS (M+H)+=1199.2.

Step 4. 4-((1-(2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-3-oxoisoindolin-5-yl)benzamide A mixture of 4-((1-(2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetyl)azetidin-3-yl)methoxy)-N-(2-(2,6-dioxopiperidin-3-yl)-3-oxoisoindolin-5-yl)benzamide (61 mg, 0.051 mmol) in 70% acetic acid (3 mL) was heated at 70° C. for 17 h. The solvent was evaporated. The crude product was dissolved in DMF and purified via preparative HPLC with the following conditions: Column: XBridge C18, 200 mm×19 mm, 5-µm articles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-58% B over 28 minutes, then a 0-minute hold at 100% B; Flow Rate: 20 mL/min; Column Temperature: 25 C. Fractions containing the desired product were combined and dried via centrifugal evaporation to provide the desired product, 4-((1-(2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)acetyl)azetidin-3-yl)methoxy)-N-(2-(2,6-dioxopiperidin-3-yl)-3-oxoisoindolin-5-yl)benzamide (22.6 mg, 0.020 mmol, 57% yield), as white solid. LCMS (M+H)$^+$=1109.3. $^1$H NMR (500 MHZ, DMSO-d$_6$) δ 11.00 (s, 1H), 10.33 (d, J=6.3 Hz, 1H), 9.09 (d, J=6.5 Hz, 1H), 8.23 (s, 1H), 8.05 (dd, J=15.5, 8.6 Hz, 1H), 8.01-7.89 (m, 5H), 7.83 (dd, J=21.7, 8.9 Hz, 2H), 7.60 (d, J=8.4 Hz, 1H), 6.97 (dd, J=15.9, 8.4 Hz, 2H), 5.51 (d, J=5.9 Hz, 1H), 5.19 (d, J=10.7 Hz, 1H), 5.10 (dd, J=13.0, 5.1 Hz, 1H), 4.83-4.72 (m, 2H), 4.54-4.38 (m, 2H), 4.33 (d, J=17.1 Hz, 1H), 4.14-3.95 (m, 2H), 3.94-3.50 (m, 8H), 2.97-2.80 (m, 2H), 2.67-2.59 (m, 1H), 2.44-2.39 (m, 1H), 2.38 (d, J=2.7 Hz, 3H), 2.13-1.96 (m, 1H). hGal-3 IC$_{50}$=0.040 μM; hCRBN IC$_{50}$=1.27 μM.

Examples 12 to 35 in Table 1 below were synthesized using the procedures described for the above Examples.

TABLE 1

| EX # | Structure | LCMS/ ¹H NMR (500 MHz, methanol-d₄, unless otherwise indicated) | hGal-3 / hCRBN IC$_{50}$ (μM) |
| --- | --- | --- | --- |
| 12 | 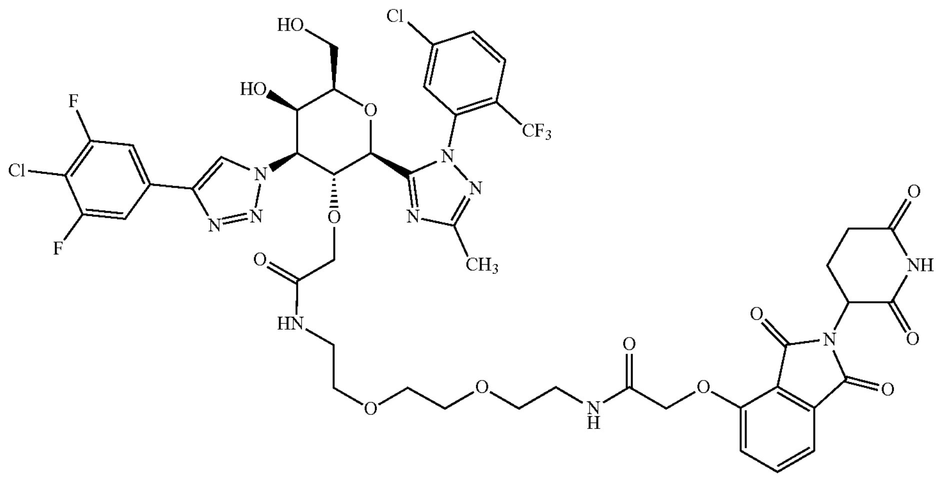 | (M + H)⁺ = 1123.6; ¹H NMR (400 MHz, methanol-d₄) δ 8.67 (d, J = 1.3 Hz, 1H), 7.85 (d, J = 8.4 Hz, 1H), 7.79-7.73 (m, 2H), 7.72-7.65 (m, 1H), 7.58-7.53 (m, 2H), 7.41 (d, J = 6.8 Hz, 1H), 7.30 (dd, J = 8.5, 0.8 Hz, 1H), 5.05-4.98 (m, 2H), 4.88-4.80 (m, 1H), 4.64 (d, J = 1.3 Hz, 2H), 4.40 (d, J = 9.2 Hz, 1H), 4.04-3.99 (m, 1H), 3.81 (dd, J = 15.0, 2.9 Hz, 1H), 3.64-3.59 (m, 1H), 3.58-3.51 (m, 3H), 3.50-3.44 (m, 4H), 3.43-3.40 (m, 2H), 3.39-3.34 (m, 2H), 3.27-3.23 (m, 2H), 3.08-2.99 (m, 2H), 2.83-2.71 (m, 1H), 2.69-2.58 (m, 2H), 2.34 (s, 3H), 2.07-2.00 (m, 1H). | 0.020/0.52 |
| 13 | 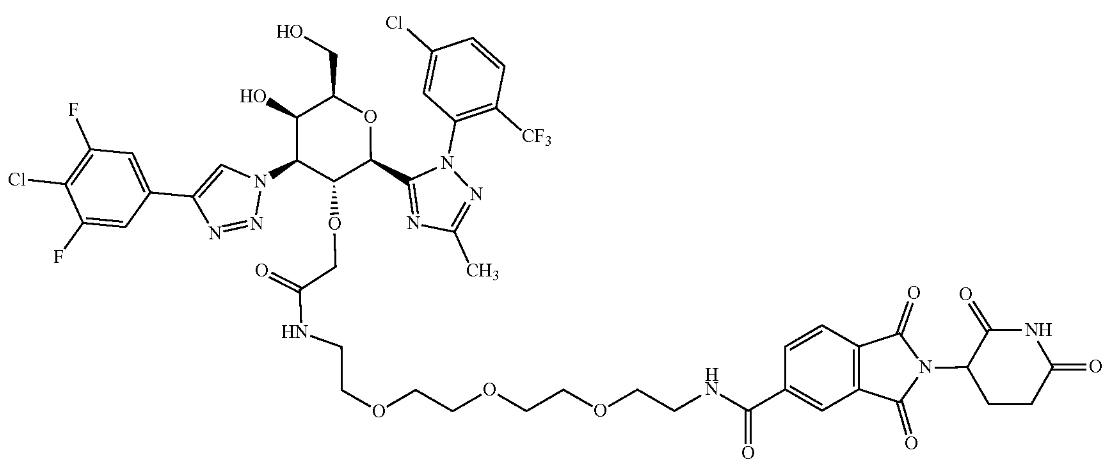 | (M + H)⁺ = 1137.4 | 0.0066/0.81 |

TABLE 1-continued

| EX # | Structure | LCMS/ ¹H NMR (500 MHz, methanol-$d_4$, unless otherwise indicated) | hGal-3 / hCRBN IC$_{50}$ (μM) |
|---|---|---|---|
| 14 | 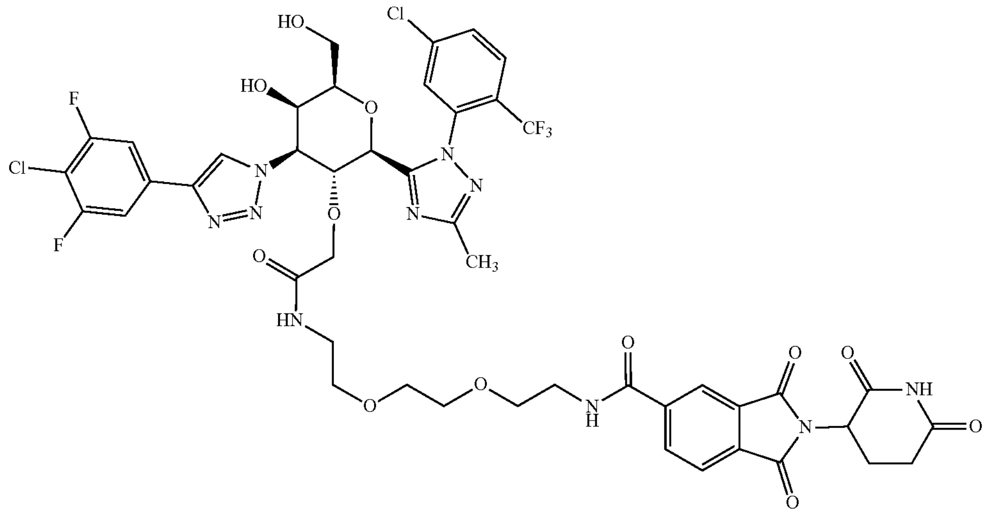 | (M + H)⁺ = 1093.4; δ 8.82-8.79 (m, 1H), 8.29-8.25 (m, 2H), 8.00-7.93 (m, 2H), 7.91-7.83 (m, 2H), 7.69-7.64 (m, 2H), 5.20 (ddd, J = 12.6, 5.4, 2.1 Hz, 1H), 5.14 (dd, J = 10.7, 2.5 Hz, 1H), 5.01-4.94 (m, 1H), 4.54 (dd, J = 9.4, 3.6 Hz, 1H), 4.14 (d, J = 2.8 Hz, 1H), 3.93 (d, J = 14.9 Hz, 1H), 3.79-3.73 (m, 1H), 3.71-3.55 (m, 11H), 3.42-3.37 (m, 2H), 3.21-3.13 (m, 2H), 2.96-2.86 (m, 1H), 2.83-2.73 (m, 2H), 2.47-2.44 (m, 3H), 2.22-2.15 (m, 1H). | 0.025/1.50 |
| 15 | 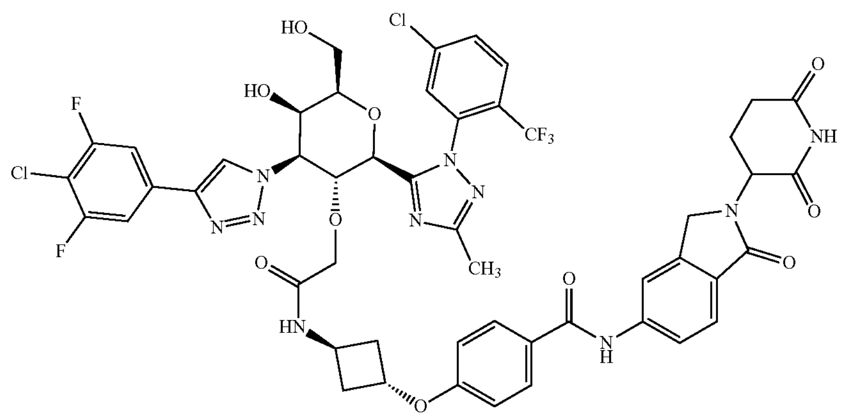 | (M + H)⁺ = 1111.7; δ 8.85 (s, 1H), 8.16 (d, J = 0.8 Hz, 1H), 8.00 (d, J = 8.8 Hz, 1H), 7.97-7.89 (m, 4H), 7.82-7.78 (m, 1H), 7.78-7.73 (m, 1H), 7.70 (d, J = 8.0 Hz, 2H), 6.92-6.86 (m, 2H), 5.21-5.14 (m, 2H), 5.00 (br t, J = 9.8 Hz, 1H), 4.83 (ddd, J = 8.7, 4.3, 1.9 Hz, 1H), 4.59-4.47 (m, 3H), 4.25-4.18 (m, 1H), 4.16 (d, J = 2.8 Hz, 1H), 3.92 (d, J = 15.1 Hz, 1H), 3.77-3.65 (m, 4H), 2.99-2.89 (m, 1H), 2.86-2.77 (m, 1H), 2.59-2.50 (m, 1H), 2.48 (s, 3H), 2.46-2.29 (m, 4H), 2.21 (dtd, J = 12.8, 5.2, 2.3 Hz, 1H). | 0.42/0.38 |

TABLE 1-continued

| EX # | Structure | LCMS/ ¹H NMR (500 MHz, methanol-d₄, unless otherwise indicated) | hGal-3 / hCRBN IC₅₀ (μM) |
|---|---|---|---|
| 16 | 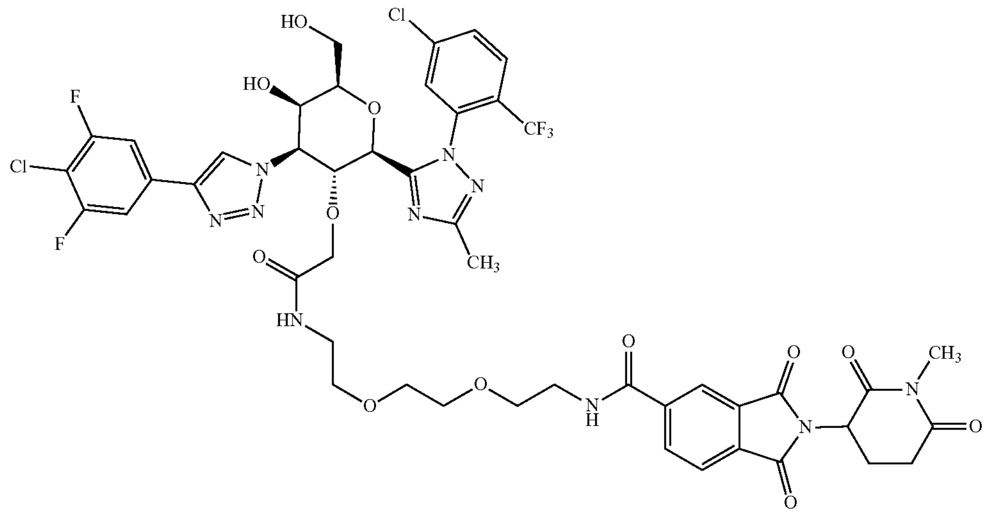 | (M + H)⁺ = 1107.4; δ 8.81 (d, J = 1.7 Hz, 1H), 8.30-8.24 (m, 2H), 8.01-7.93 (m, 2H), 7.91-7.83 (m, 2H), 7.71-7.64 (m, 2H), 5.23 (ddd, J = 13.0, 5.4, 3.0 Hz, 1H), 5.18-5.12 (m, 1H), 5.01-4.93 (m, 1H), 4.54 (br d, J = 9.1 Hz, 1H), 4.15-4.11 (m, 1H), 3.93 (br d, J = 14.9 Hz, 1H), 3.79-3.73 (m, 1H), 3.71-3.53 (m, 12H), 3.41-3.37 (m, 2H), 3.21-3.14 (m, 2H), 3.18 (s, 3H), 2.96-2.91 (m, 1H), 2.79-2.70 (m, 1H), 2.46-2.44 (m, 3H), 2.21-2.12 (m, 1H). | 0.069/>50 |
| 17 | 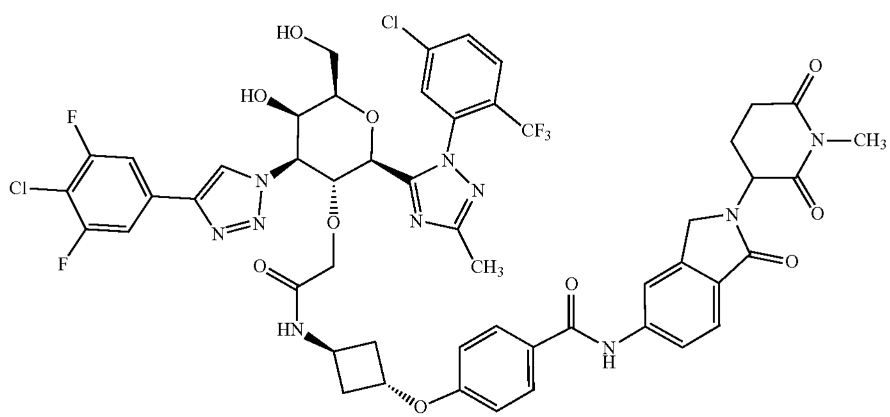 | (M + H)⁺ = 1123.7; δ 8.85 (s, 1H), 8.17 (s, 1H), 8.00 (d, J = 8.8 Hz, 1H), 7.94 (d, J = 8.5 Hz, 2H), 7.92-7.88 (m, 2H), 7.83-7.79 (m, 1H), 7.78-7.73 (m, 1H), 7.72-7.67 (m, 2H), 6.89 (d, J = 8.8 Hz, 2H), 5.22-5.15 (m, 2H), 5.00 (br t, J = 9.8 Hz, 1H), 4.84-4.81 (m, 1H), 4.59-4.45 (m, 3H), 4.25-4.11 (m, 2H), 3.92 (d, J = 15.1 Hz, 1H), 3.76-3.65 (m, 4H), 3.17 (s, 3H), 3.00-2.90 (m, 2H), 2.54-2.29 (m, 5H), 2.48 (s, 3H), 2.24-2.15 (m, 1H). | 0.14/>50 |

TABLE 1-continued

| EX # | Structure | LCMS/ ¹H NMR (500 MHz, methanol-d₄, unless otherwise indicated) | hGal-3 / hCRBN IC$_{50}$ (μM) |
|---|---|---|---|
| 18 | 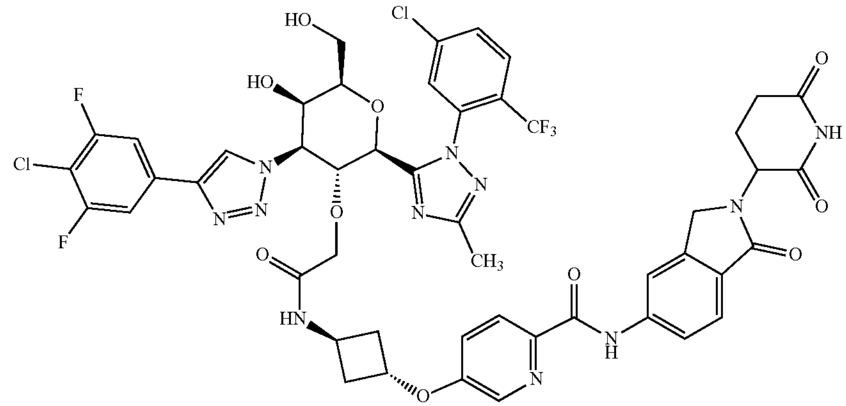 | (M + H)⁺ = 1110.9; δ 8.86 (s, 1H), 8.27-8.22 (m, 2H), 8.17 (d, J = 8.5 Hz, 1H), 8.01 (d, J = 8.8 Hz, 1H), 7.93-7.89 (m, 2H), 7.88-7.80 (m, 2H), 7.70 (d, J = 7.7 Hz, 2H), 7.34 (dd, J = 8.5, 2.8 Hz, 1H), 5.21-5.15 (m, 2H), 5.00 (br t, J = 9.8 Hz, 1H), 4.93-4.89 (m, 1H), 4.60-4.49 (m, 3H), 4.25-4.18 (m, 1H), 4.16 (d, J = 2.5 Hz, 1H), 3.93 (br d, J = 15.1 Hz, 1H), 3.78-3.65 (m, 4H), 2.99-2.88 (m, 1H), 2.86-2.78 (m, 1H), 2.59-2.51 (m, 1H), 2.49-2.42 (m, 2H), 2.48 (s, 3H), 2.39-2.32 (m, 2H), 2.25-2.17 (m, 1H). | 0.22/0.11 |
| 19 | 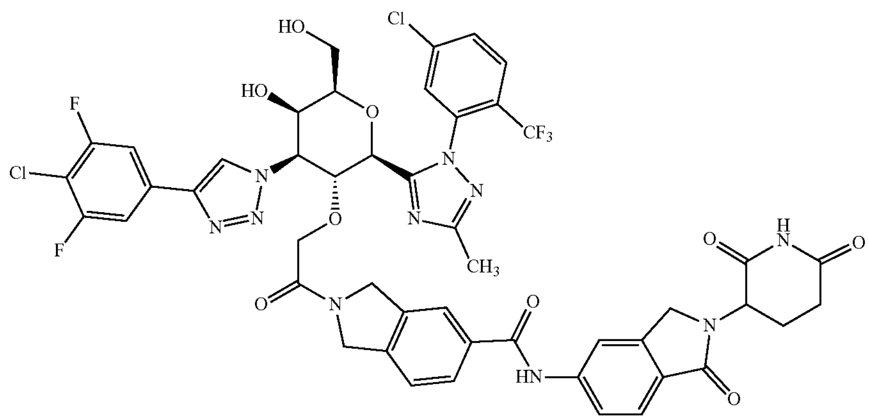 | (M + H)⁺ = 1065.0; δ 8.77 (d, J = 4.4 Hz, 1H), 8.22-8.16 (m, 1H), 8.02-7.96 (m, 2H), 7.94-7.87 (m, 2H), 7.85-7.75 (m, 3H), 7.61-7.54 (m, 2H), 7.35 (br d, J = 8.0 Hz, 1H), 5.22-5.11 (m, 2H), 5.07 (br d, J = 7.4 Hz, 1H), 4.60-4.49 (m, 6H), 4.17-4.04 (m, 3H), 3.78-3.72 (m, 1H), 3.71-3.64 (m, 2H), 3.00-2.89 (m, 1H), 2.86-2.79 (m, 1H), 2.60-2.49 (m, 1H), 2.43 (s, 3H), 2.25-2.18 (m, 1H). | 0.051/0.017 |

TABLE 1-continued
| EX # | Structure | LCMS/ ¹H NMR (500 MHz, methanol-d₄, unless otherwise indicated) | hGal-3 / hCRBN IC$_{50}$ (μM) |
|---|---|---|---|
| 20 | 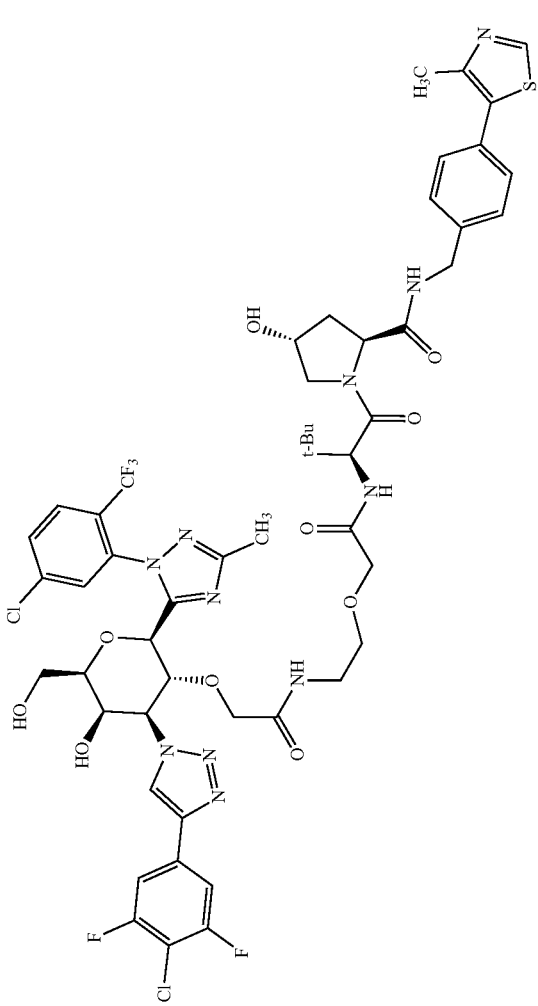 | (M + H)⁺ = 1192.1; δ 8.87 (s, 1H), 8.82 (s, 1H), 7.98 (d, J = 8.5 Hz, 1H), 7.91-7.84 (m, 2H), 7.64 (d, J = 8.0 Hz, 2H), 7.42 (s, 4H), 5.18 (dd, J = 10.7, 2.8 Hz, 1H), 5.13-5.03 (m, 1H), 4.73 (s, 1H), 4.65 (t, J = 8.4 Hz, 1H), 4.56-4.50 (m, 2H), 4.47 (s, 2H), 4.14 (d, J = 2.5 Hz, 1H), 4.01-3.81 (m, 5H), 3.77-3.68 (m, 2H), 3.65-3.57 (m, 2H), 3.46 (ddd, J = 9.5, 5.8, 4.0 Hz, 1H), 3.39-3.32 (m, 2H), 3.21-3.14 (m, 1H), 2.47 (s, 3H), 2.46 (s, 3H), 2.31-2.23 (m, 1H), 2.19-2.10 (m, 1H), 1.03 (s, 9H). | 0.050/ND |

TABLE 1-continued
| EX # | Structure | LCMS/ $^1$H NMR (500 MHz, methanol-$d_4$, unless otherwise indicated) | hGal-3 / hCRBN IC$_{50}$ (µM) |
|---|---|---|---|
| 21 | 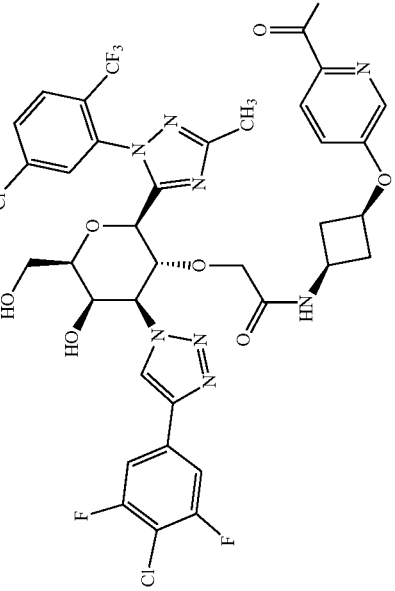 | (M + H)$^+$ = 1110.0; δ 8.82 (s, 1H), 8.27 (d, J = 2.8 Hz, 1H), 8.16 (d, J = 8.8 Hz, 1H), 8.00 (t, J = 8.9 Hz, 2H), 7.92-7.88 (m, 2H), 7.72 (d, J = 7.4 Hz, 1H), 7.66 (d, J = 8.0 Hz, 2H), 7.64-7.59 (m, 1H), 7.39 (dd, J = 8.8, 2.8 Hz, 1H), 5.21 (dd, J = 13.3, 5.1 Hz, 1H), 5.16 (dd, J = 10.7, 2.8 Hz, 1H), 4.99 (br t, J = 9.9 Hz, 1H), 4.70-4.60 (m, 2H), 4.59-4.53 (m, 1H), 4.50 (d, J = 9.1 Hz, 1H), 4.14 (d, J = 3.0 Hz, 1H), 3.95-3.85 (m, 2H), 3.74-3.63 (m, 4H), 2.99-2.89 (m, 1H), 2.89-2.77 (m, 3H), 2.54 (qd, J = 13.3, 4.8 Hz, 1H), 2.47 (s, 3H), 2.22 (dtd, J = 12.8, 5.2, 2.2 Hz, 1H), 2.05 (dt, J = 10.7, 8.4 Hz, 1H), 1.91 (dt, J = 11.1, 8.3 Hz, 1H). | 0.070/0.93 |

TABLE 1-continued

| EX # | Structure | LCMS/ ¹H NMR (500 MHz, methanol-d₄, unless otherwise indicated) | hGal-3/ hCRBN IC$_{50}$ (μM) |
|---|---|---|---|
| 22 | 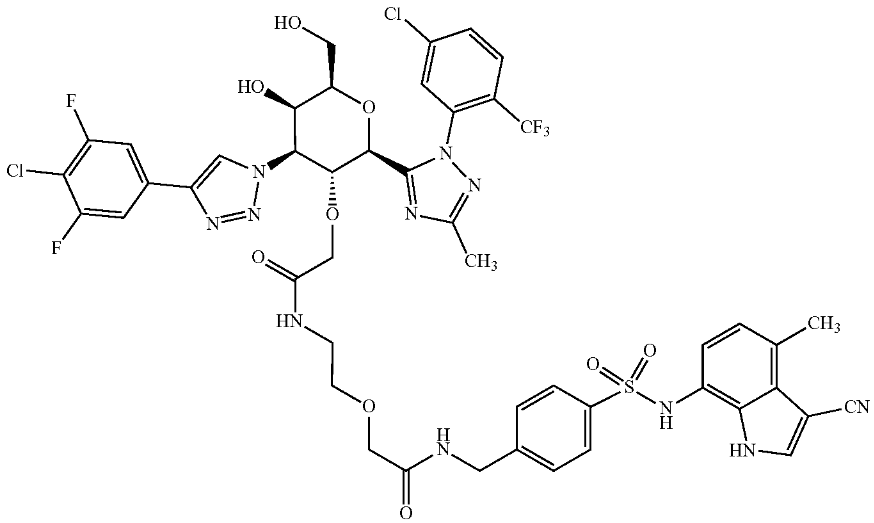 | (M + H)⁺ = 1101.7; δ 8.78 (s, 1H), 7.98-7.90 (m, 2H), 7.89-7.83 (m, 2H), 7.62 (dd, J = 11.7, 8.1 Hz, 4H), 7.38 (d, J = 8.3 Hz, 2H), 6.71 (d, J = 7.7 Hz, 1H), 6.48 (d, J = 7.7 Hz, 1H), 5.04 (dd, J = 10.7, 2.8 Hz, 1H), 4.92 (br t, J = 9.6 Hz, 1H), 4.49-4.44 (m, 3H), 4.09 (d, J = 2.8 Hz, 1H), 4.04-3.94 (m, 2H), 3.90 (br d, J = 15.1 Hz, 1H), 3.68-3.62 (m, 4H), 3.45 (t, J = 5.2 Hz, 2H), 3.26-3.21 (m, 2H), 2.63 (s, 3H), 2.44 (s, 3H). | 0.294/ND |
| 23 | 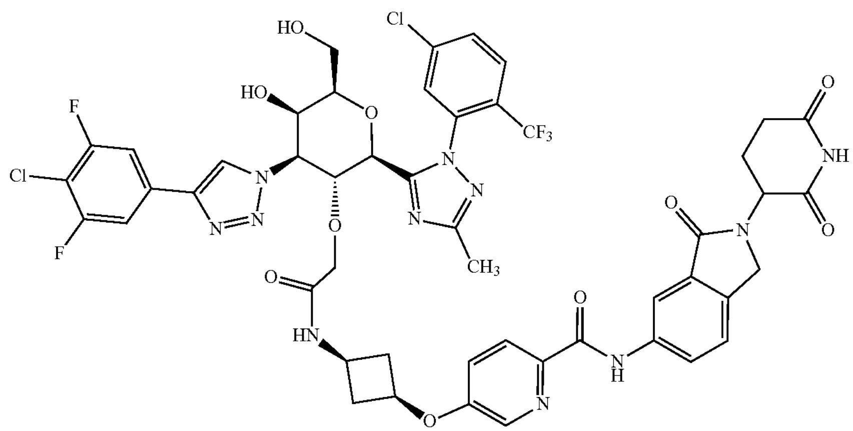 | (M + H)⁺ = 1110.3; ¹H NMR (400 MHz, methanol-d₄) δ 8.81 (s, 1H), 8.34 (d, J = 2.0 Hz, 1H), 8.28 (d, J = 2.6 Hz, 1H), 8.17 (d, J = 8.6 Hz, 1H), 8.03 (dd, J = 8.1, 2.0 Hz, 1H), 8.01-7.96 (m, 1H), 7.92-7.87 (m, 2H), 7.69-7.64 (m, 2H), 7.61 (d, J = 8.4 Hz, 1H), 7.39 (dd, J = 8.8, 2.9 Hz, 1H), 5.23-5.12 (m, 2H), 5.04-4.95 (m, 1H), 4.59-4.45 (m, 4H), 4.14 (d, J = 2.9 Hz, 1H), 3.95-3.86 (m, 2H), 3.75-3.63 (m, 4H), 3.00-2.76 (m, 4H), 2.60-2.48 (m, 1H), 2.47 (s, 3H), 2.22 (dtd, J = 12.7, 5.3, 2.3 Hz, 1H), 2.10-2.00 (m, 1H), 1.97-1.87 (m, 1H). | 0.042/0.070 |

TABLE 1-continued

| EX # | Structure | LCMS/ $^1$H NMR (500 MHz, methanol-$d_4$, unless otherwise indicated) | hGal-3/ hCRBN IC$_{50}$ (μM) |
|---|---|---|---|
| 24 | 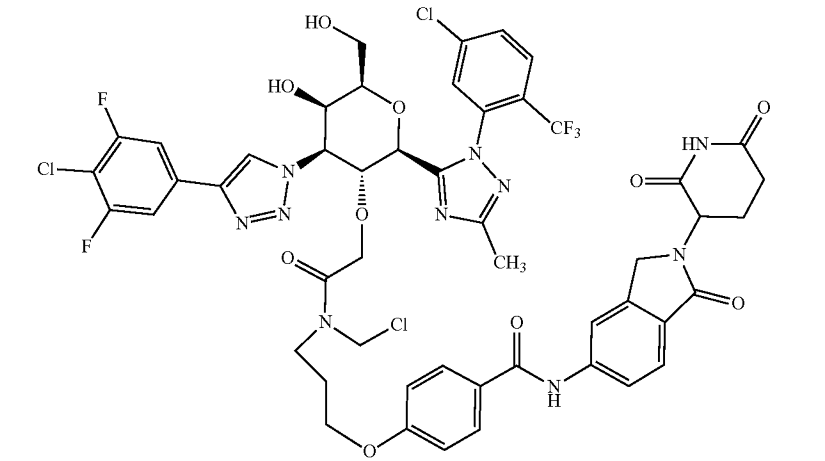 [SMILES: Cc1nc([C@@H]2O[C@H](CO)[C@H](O)[C@H](n3cc(-c4cc(F)c(Cl)c(F)c4)nn3)[C@H]2OCC(=O)N(CCl)CCCOc2ccc(C(=O)Nc3ccc4c(c3)CN(C3CCC(=O)NC3=O)C4=O)cc2)n(-c2cc(Cl)ccc2C(F)(F)F)n1] | (M + H)$^+$ = 1147.1; $^1$H NMR (400 MHz, DMSO-$d_6$) δ 10.98 (s, 1H), 10.37 (d, J = 2.1 Hz, 1H), 9.13 (d, J = 1.2 Hz, 1H), 8.15 (d, J = 1.7 Hz, 1H), 8.04 (dd, J = 9.3, 2.0 Hz, 1H), 8.01-7.91 (m, 3H), 7.90-7.79 (m, 3H), 7.71 (d, J = 8.4 Hz, 1H), 7.26-7.07 (m, 1H), 6.98 (dd, J = 8.9, 6.7 Hz, 2H), 5.76 (s, 2H), 5.55 (d, J = 5.7 Hz, 1H), 5.19-5.14 (m, 1H), 5.11 (dd, J = 13.1, 5.1 Hz, 1H), 4.87 (t, J = 9.9 Hz, 1H), 4.78-4.67 (m, 1H), 4.54-4.41 (m, 2H), 4.34 (d, J = 17.3 Hz, 1H), 4.00-3.93 (m, 1H), 3.93-3.77 (m, 3H), 3.74-3.53 (m, 3H), 3.49-3.36 (m, 2H), 3.16-2.99 (m, 2H), 3.00-2.86 (m, 1H), 2.65-2.56 (m, 1H), 2.44-2.38 (m, 1H), 2.36 (d, J = 1.9 Hz, 3H), 2.21-2.11 (m, 1H), 2.09-1.91 (m, 1H). | 0.212/2.16 |
| 25 | 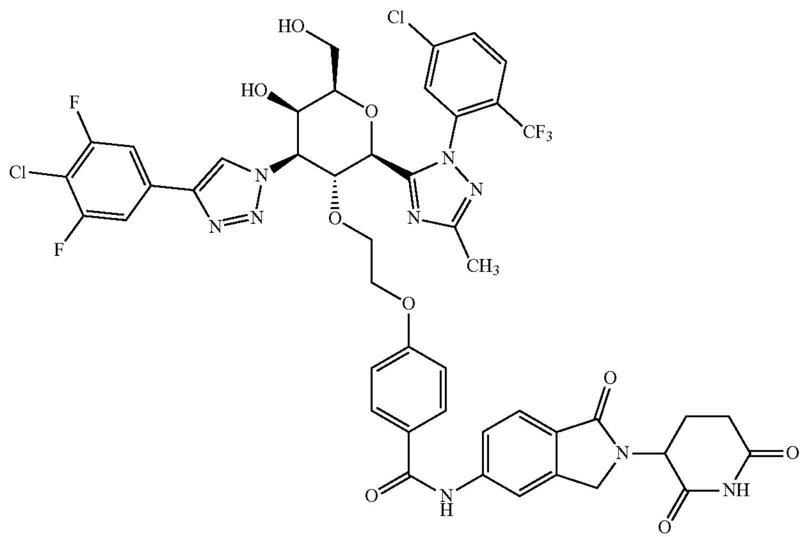 [SMILES: Cc1nc([C@@H]2O[C@H](CO)[C@H](O)[C@H](n3cc(-c4cc(F)c(Cl)c(F)c4)nn3)[C@H]2OCCOc2ccc(C(=O)Nc3ccc4c(c3)CN(C3CCC(=O)NC3=O)C4=O)cc2)n(-c2cc(Cl)ccc2C(F)(F)F)n1] | (M + H)$^+$ = 1026.0; $^1$H NMR (400 MHz, methanol-$d_4$) δ 8.79 (s, 1H), 8.21-8.10 (m, 1H), 7.99 (d, J = 8.5 Hz, 1H), 7.91-7.83 (m, 2H), 7.83-7.77 (m, 3H), 7.76-7.72 (m, 1H), 7.58 (d, J = 8.7 Hz, 2H), 6.78 (d, J = 8.5 Hz, 2H), 5.16 (dd, J = 13.3, 5.2 Hz, 2H), 5.04 (dd, J = 10.5, 2.8 Hz, 1H), 4.95-4.78 (m, 1H), 4.55 (d, J = 17.2 Hz, 1H), 4.49 (d, J = 17.1 Hz, 1H), 4.43 (d, J = 9.1 Hz, 1H), 4.24 (dd, J = 5.7, 2.0 Hz, 1H), 4.12 (d, J = 2.6 Hz, 1H), 3.91-3.65 (m, 6H), 3.66-3.52 (m, 1H), 3.49-3.36 (m 1H), 2.53 (qd, J = 13.3, 4.8 Hz, 1H), 2.44 (s, 3H), 2.20 (dtd, J = 12.8, 5.2, 2.5 Hz, 1H). | 0.139/2.69 |

TABLE 1-continued

| EX # | Structure | LCMS/ ¹H NMR (500 MHz, methanol-d₄, unless otherwise indicated) | hGal-3/ hCRBN IC$_{50}$ (μM) |
|---|---|---|---|
| 26 | 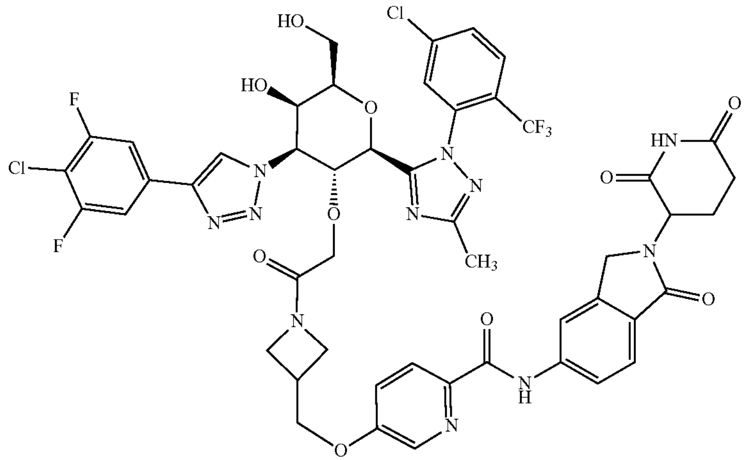 [SMILES: Cc1nc([C@@H]2O[C@H](CO)[C@H](O)[C@H](n3cc(-c4cc(F)c(Cl)c(F)c4)nn3)[C@H]2OCC(=O)N2CC(COc3ccc(C(=O)Nc4ccc5c(c4)CN(C4CCC(=O)NC4=O)C5=O)nc3)C2)n(-c2cc(Cl)ccc2C(F)(F)F)n1] | (M + H)⁺ = 1110.0; ¹H NMR (500 MHz, DMSO-d₆) δ 10.99 (s, 1H), 10.78 (d, J = 13.3 Hz, 1H), 9.14 (d, J = 8.4 Hz, 1H), 8.31 (dd, J = 14.5, 2.7 Hz, 1H), 8.27 (s, 1H), 8.14 (t, J = 8.1 Hz, 1H), 8.06 (dd, J = 14.9, 8.6 Hz, 1H), 8.03-7.93 (m, 2H), 7.92-7.65 (m, 3H), 7.54 (dd, J = 14.0, 10.7 Hz, 1H), 5.47 (dd, J = 6.0, 3.6 Hz, 1H), 5.21 (d, J = 10.7 Hz, 1H), 5.12 (dd, J = 13.3, 5.1 Hz, 1H), 4.85-4.74 (m, 1H), 4.74-4.64 (m, 1H), 4.54-4.43 (m, 2H), 4.35 (d, J = 17.2 Hz, 1H), 4.24-4.04 (m, 2H), 3.95-3.85 (m, 2H), 3.85-3.66 (m, 4H), 3.66-3.39 (m, 4H), 3.01-2.80 (m, 2H), 2.67-2.57 (m, 1H), 2.45-2.40 (m, 1H), 2.43 (s, 3H), 2.07-1.96 (m, 1H). | 0.085/0.251 |
| 27 | 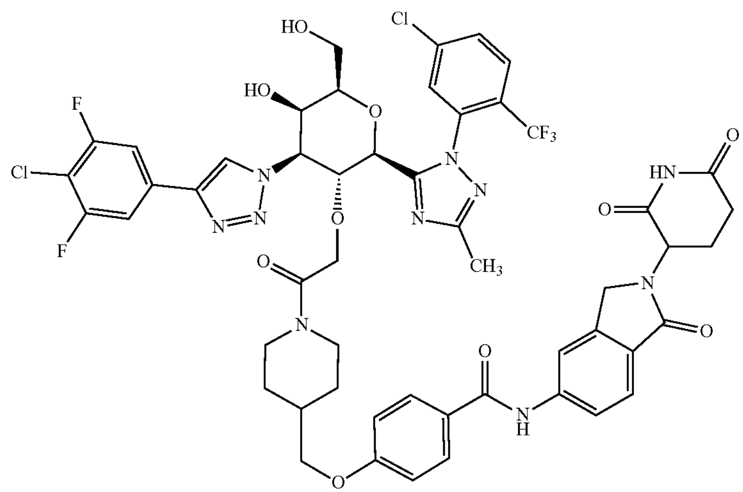 [SMILES: Cc1nc([C@@H]2O[C@H](CO)[C@H](O)[C@H](n3cc(-c4cc(F)c(Cl)c(F)c4)nn3)[C@H]2OCC(=O)N2CCC(COc3ccc(C(=O)Nc4ccc5c(c4)CN(C4CCC(=O)NC4=O)C5=O)cc3)CC2)n(-c2cc(Cl)ccc2C(F)(F)F)n1] | (M + H)⁺ = 1137.1; ¹H NMR (500 MHz, DMSO-d₆) δ 11.00 (s, 1H), 10.40 (s, 1H), 9.14 (d, J = 4.2 Hz, 1H), 8.15 (s, 1H), 8.06 (d, J = 8.6 Hz, 1H), 8.04-7.93 (m, 4H), 7.88 (d, J = 8.9 Hz, 2H), 7.84 (d, J = 8.8 Hz, 1H), 7.71 (d, J = 8.3 Hz, 1H), 7.06-6.96 (m, 2H), 5.50 (s, 1H), 5.28-5.19 (m, 1H), 5.11 (dd, J = 13.2, 5.1 Hz, 1H), 4.85-4.75 (m, 1H), 4.75-4.68 (m, 1H), 4.58-4.41 (m, 2H), 4.34 (d, J = 17.3 Hz, 1H), 4.20-4.10 (m, 1H), 4.01-3.84 (m, 3H), 3.84-3.66 (m, 3H), 3.62-3.51 (m, 1H), 3.14-2.96 (m, 1H), 2.98-2.84 (m, 1H), 2.74-2.58 (m, 3H), 2.41 (s, 3H), 2.46-2.39 (m, 2H), 2.07-1.99 (m, 1H), 1.95-1.81 (m, 1H), 1.70-1.57 (m, 1H), 1.56-1.43 (m, 1H), 1.02-0.76 (m, 2H). | 0.312/0.374 |

TABLE 1-continued
| EX # | Structure | LCMS/ $^1$H NMR (500 MHz, methanol-$d_4$, unless otherwise indicated) | hGal-3/ hCRBN IC$_{50}$ (μM) |
|---|---|---|---|
| 28 | 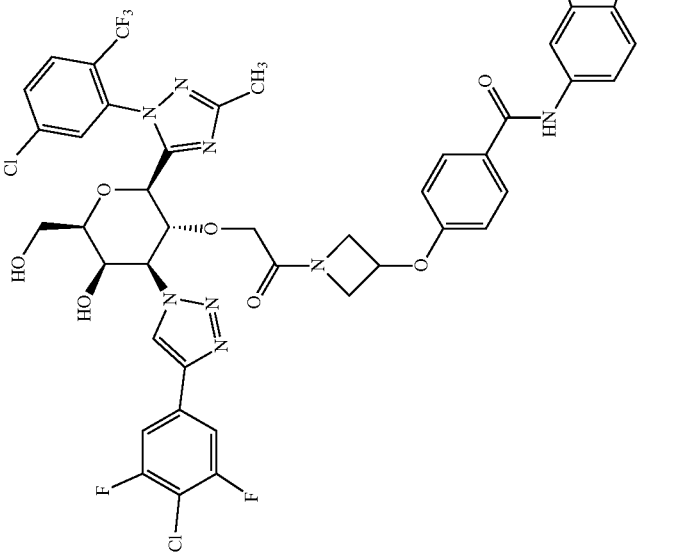 | (M + H)$^+$ = 1109.1; $^1$H NMR (500 MHz, DMSO-$d_6$) δ 10.55-10.38 (m, 1H), 9.14 (d, J = 20.2 Hz, 1H), 8.15 (s, 1H), 8.06 (t, J = 8.6 Hz, 1H), 8.01-7.94 (m, 4H), 7.93-7.79 (m, 3H), 7.73 (d, J = 8.3 Hz, 1H), 6.86 (d, J = 8.5 Hz, 2H), 5.50 (t, J = 7.5 Hz, 1H), 5.25-5.14 (m, 2H), 4.97 (bs, 1H), 4.86-4.76 (m, 1H), 4.75-4.66 (m, 1H), 4.54-4.43 (m, 2H), 4.34 (d, J = 17.2 Hz, 1H), 4.25-4.03 (m, 2H), 4.10-4.00 (m, 1H), 3.97-3.65 (m, 5H), 3.67-3.52 (m, 2H), 3.52-3.31 (m, 2H), 3.02 (s, 3H), 2.86-2.72 (m, 1H), 2.47-2.43 (m, 1H), 2.42 (d, J = 4.2 Hz, 3H), 2.18-1.90 (m, 1H). | 0.098/10.4 |

TABLE 1-continued
| EX # | Structure | LCMS/ $^1$H NMR (500 MHz, methanol-$d_4$, unless otherwise indicated) | hGal-3 / hCRBN IC$_{50}$ (μM) |
|---|---|---|---|
| 29 | 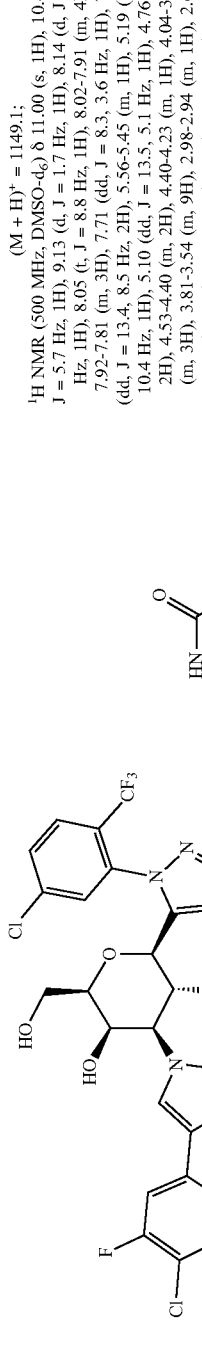 | (M + H)$^+$ = 1149.1; $^1$H NMR (500 MHz, DMSO-$d_6$) δ 11.00 (s, 1H), 10.41 (d, J = 5.7 Hz, 1H), 9.13 (d, J = 1.7 Hz, 1H), 8.14 (d, J = 5.7 Hz, 1H), 8.05 (t, J = 8.8 Hz, 1H), 8.02-7.91 (m, 4H), 7.92-7.81 (m, 3H), 7.71 (dd, J = 8.3, 3.6 Hz, 1H), 7.05 (dd, J = 13.4, 8.5 Hz, 2H), 5.56-5.45 (m, 1H), 5.19 (d, J = 10.4 Hz, 1H), 5.10 (dd, J = 13.5, 5.1 Hz, 1H), 4.76 (bs, 2H), 4.53-4.40 (m, 2H), 4.40-4.23 (m, 1H), 4.04-3.86 (m, 3H), 3.81-3.54 (m, 9H), 2.98-2.94 (m, 1H), 2.66-2.56 (m, 1H), 2.44-2.33 (m, 5H), 2.23-2.15 (m, 1H), 2.13-1.97 (m, 2H), 1.96-1.87 (m, 1H), 1.86-1.79 (m, 1H). | 0.160/0.350 |

TABLE 1-continued
| EX # | Structure | LCMS/ ¹H NMR (500 MHz, methanol-d₄, unless otherwise indicated) | hGal-3 / hCRBN IC$_{50}$ (µM) |
|---|---|---|---|
| 30 | 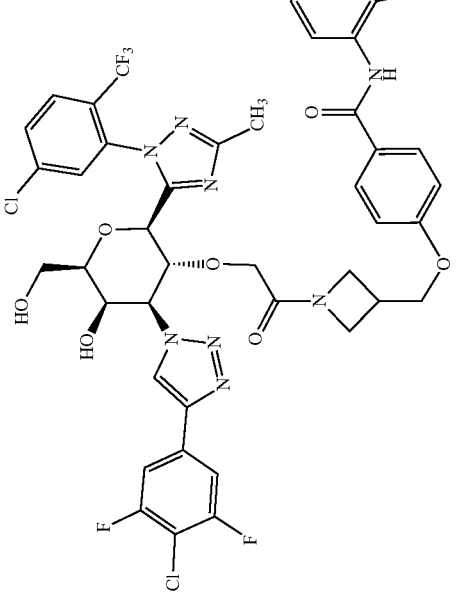 | (M + H)⁺ = 1109.4; ¹H NMR (500 MHz, DMSO-d₆) δ 11.00 (s, 1H), 10.24 (s, 1H), 9.09 (d, J = 6.3 Hz, 1H), 8.05 (dd, J = 14.8, 8.7 Hz, 1H), 8.01-7.91 (m, 4H), 7.91-7.76 (m, 2H), 7.71 (d, J = 7.7 Hz, 1H), 7.63 (d, J = 7.3 Hz, 1H), 7.57 (t, J = 7.6 Hz, 1H), 6.97 (dd, J = 14.5, 8.5 Hz, 2H), 5.57-5.43 (m, 1H), 5.23-5.16 (m, 1H), 5.14 (d, J = 17.6 Hz, 1H), 4.86-4.70 (m, 2H), 4.55-4.42 (m, 3H), 4.10-3.97 (m, 2H), 3.97-3.83 (m, 2H), 3.83-3.61 (m, 6H), 3.43-3.20 (m, 2H), 2.98-2.75 (m, 2H), 2.65-2.58 (m, 1H), 2.47-2.38 (m, 1H), 2.38 (d, J = 2.8 Hz, 3H), 2.03 (s, 1H). | 0.086/10.6 |

TABLE 1-continued
| EX # | Structure | LCMS/ $^1$H NMR (500 MHz, methanol-$d_4$, unless otherwise indicated) | hGal-3/ hCRBN IC$_{50}$ (µM) |
|---|---|---|---|
| 31 | 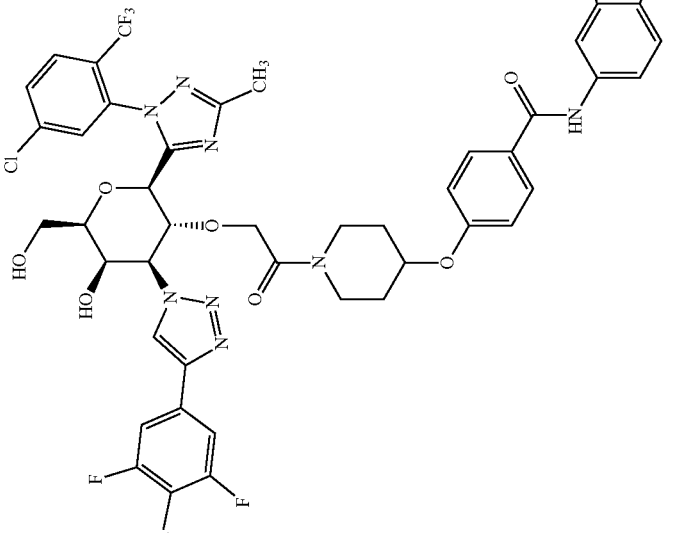 | (M + H)$^+$ = 1122.9; $^1$H NMR (500 MHz, DMSO-$d_6$) δ 11.00 (s, 1H), 10.41 (s, 1H), 9.14 (s, 1H), 8.16 (s, 1H), 8.07 (d, J = 8.6 Hz, 1H), 8.06-7.93 (m, 4H), 7.92-7.83 (m, 3H), 7.73 (d, J = 8.3 Hz, 1H), 7.05 (d, J = 8.5 Hz, 2H), 5.49 (d, J = 5.9 Hz, 1H), 5.24 (d, J = 10.8 Hz, 1H), 5.12 (dd, J = 13.3, 5.2 Hz, 1H), 4.92-4.78 (m 1H), 4.75-4.69 (m, 1H), 4.68-4.59 (m, 1H), 4.54-4.44 (m, 2H), 4.35 (d, J = 17.2 Hz, 1H), 4.05-3.92 (m, 3H), 3.78-3.63 (m, 2H), 3.59-3.43 (m, 2H), 3.17-2.76 (m, 4H), 2.67-2.59 (m, 1H), 2.46-2.41 (m, 1H), 2.40 (s, 3H), 2.19-1.98 (m, 1H), 1.85-1.72 (m, 1H), 1.71-1.61 (m, 1H), 1.35 (m, 2H). | 0.139/0.447 |

TABLE 1-continued
| EX # | Structure | LCMS/ $^1$H NMR (500 MHz, methanol-$d_4$, unless otherwise indicated) | hGal-3 / hCRBN IC$_{50}$ (µM) |
|---|---|---|---|
| 32 | 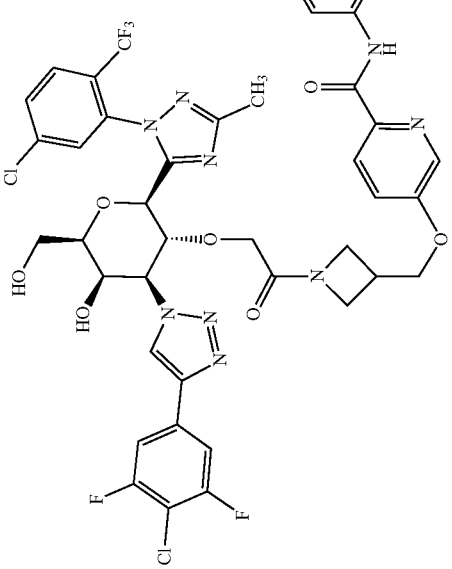 | (M + H)$^+$ = 1110.3; $^1$H NMR (500 MHz, DMSO-$d_6$) δ 11.00 (s, 1H), 10.55 (d, J = 9.8 Hz, 1H), 9.11 (d, J = 8.3 Hz, 1H), 8.34-8.26 (m, 1H), 8.17-8.02 (m, 3H), 8.02-7.94 (m, 1H), 7.90 (dd, J = 13.0, 6.4 Hz, 1H), 7.84 (d, J = 8.8 Hz, 1H), 7.77 (d, J = 8.8 Hz, 1H), 7.69-7.55 (m, 2H), 7.51 (dd, J = 17.5, 8.6 Hz, 1H), 5.49 (t, J = 5.1 Hz, 1H), 5.29-5.08 (m, 2H), 4.86-4.70 (m, 2H), 4.66-4.32 (m, 3H), 4.20-3.97 (m, 2H), 3.97-3.84 (m, 2H), 3.84-3.63 (m, 2H), 3.55-3.29 (m, 6H), 3.04-2.78 (m, 2H), 2.65-2.56 (m, 1H), 2.47-2.39 (m, 1H), 2.39 (s, 3H), 2.11-1.96 (m, 1H). | 0.094/13.7 |

TABLE 1-continued

| EX # | Structure | LCMS/ ¹H NMR (500 MHz, methanol-d₄, unless otherwise indicated) | hGal-3 / hCRBN IC$_{50}$ (µM) |
|---|---|---|---|
| 33 | 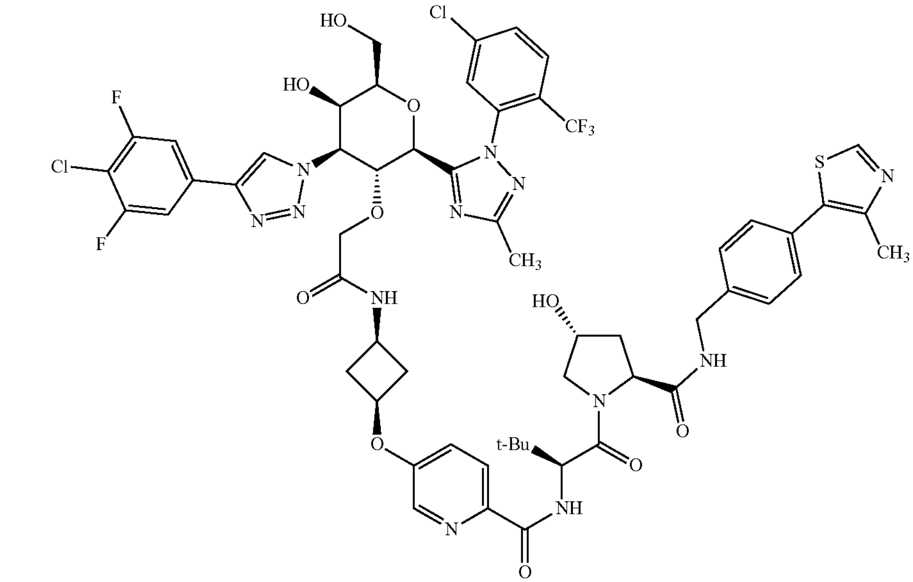 [SMILES: Cc1nc([C@@H]2O[C@H](CO)[C@H](O)[C@H](n3cc(-c4cc(F)c(Cl)c(F)c4)nn3)[C@H]2OCC(=O)N[C@H]2C[C@@H](Oc3ccc(C(=O)N[C@H](C(=O)N4C[C@H](O)C[C@H]4C(=O)NCc4ccc(-c5scnc5C)cc4)C(C)(C)C)nc3)C2)n(-c2cc(Cl)ccc2C(F)(F)F)n1] | (M + H)⁺ = 1281.3; ¹H NMR (500 MHz, DMSO-d₆) δ 9.10 (s, 1H), 8.99 (s, 1H), 8.63 (t, J = 6.1 Hz, 1H), 8.37 (d, J = 9.7 Hz, 1H), 8.22 (d, J = 2.8 Hz, 1H), 8.05 (d, J = 9.2 Hz, 1H), 8.03-7.92 (m, 3H), 7.82 (d, J = 9.0 Hz, 2H), 7.49-7.14 (m, 5H), 6.96 (s, 1H), 5.52 (d, J = 6.0 Hz, 1H), 5.25-5.13 (m, 2H), 4.88 (t, J = 9.9 Hz, 1H), 4.80-4.65 (m, 2H), 4.55-4.35 (m, 5H), 4.27 (dd, J = 15.8, 5.6 Hz, 1H), 4.02-3.91 (m, 1H), 3.86-3.62 (m, 5H), 3.62-3.55 (m,1H), 2.77-2.62 (m, 2H), 2.53-2.49 (m, 2H), 2.46 (s, 3H), 2.37 (s, 3H), 2.13-2.05 (m, 1H), 2.02-1.90 (m, 1H), 1.87-1.79 (m, 1H), 1.79-1.66 (m, 1H), 1.00 (s, 9H). | 1.01/ND |
| 34 | 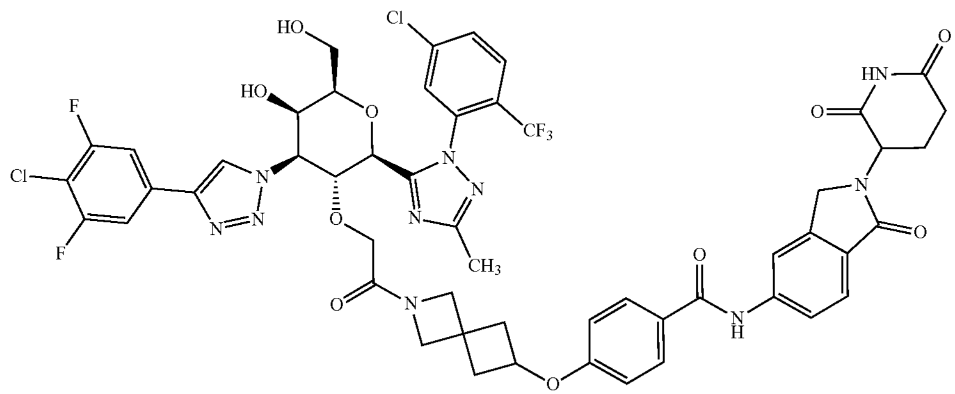 [SMILES: Cc1nc([C@@H]2O[C@H](CO)[C@H](O)[C@H](n3cc(-c4cc(F)c(Cl)c(F)c4)nn3)[C@H]2OCC(=O)N2CC3(CC(Oc4ccc(C(=O)Nc5ccc6c(c5)CN(C5CCC(=O)NC5=O)C6=O)cc4)C3)C2)n(-c2cc(Cl)ccc2C(F)(F)F)n1] | (M + H)⁺ = 1134.8; ¹H NMR (500 MHz, DMSO-d₆) δ 10.99 (s, 1H), 10.41 (d, J = 5.3 Hz, 1H), 9.13 (d, J = 9.7 Hz, 1H), 8.14 (s, 1H), 8.07 (dd, J = 8.6, 5.2 Hz, 1H), 8.01-7.92 (m, 4H), 7.89 (dd, J = 15.0, 8.7 Hz, 2H), 7.86-7.80 (m, 1H), 7.72 (d, J = 8.3 Hz, 1H), 6.92 (dd, J = 18.8, 8.4 Hz, 2H), 5.49 (dd, J = 8.8, 6.0 Hz, 1H), 5.27-5.15 (m, 1H), 5.10 (dd, J = 13.2, 5.2 Hz, 1H), 4.85-4.70 (m, 2H), 4.71-4.62 (m, 1H), 4.55-4.40 (m, 2H), 4.34 (d, J = 17.3 Hz, 1H), 3.97-3.89 (m, 1H), 3.84-3.54 (m, 7H), 3.55-3.49 (m, 2H), 2.98-2.86 (m, 1H), 2.67-2.55 (m, 3H), 2.47-2.40 (m, 1H), 2.39 (d, J = 6.8 Hz, 3H), 2.23-2.11 (m, 1H), 2.09-1.97 (m, 2H). | 0.110/1.02 |

TABLE 1-continued

| EX # | Structure | LCMS/ ¹H NMR (500 MHz, methanol-d₄, unless otherwise indicated) | hGal-3 / hCRBN IC$_{50}$ (μM) |
|---|---|---|---|
| 35 | 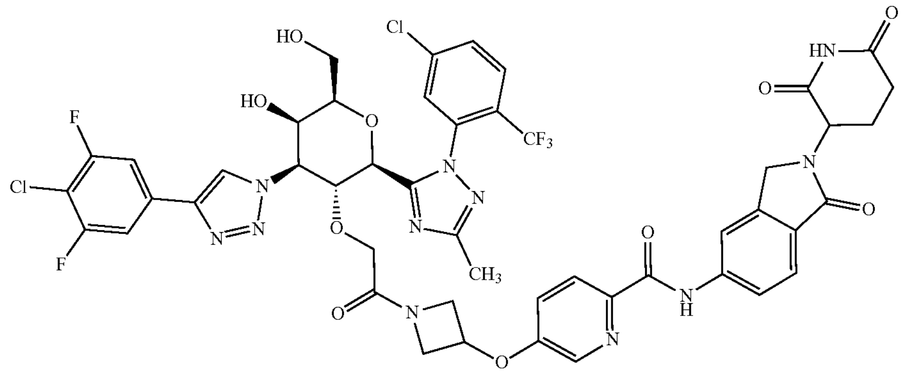 [SMILES: Cc1nc([C@@H]2O[C@H](CO)[C@H](O)[C@H](n3cc(-c4cc(F)c(Cl)c(F)c4)nn3)[C@H]2OCC(=O)N2CC(Oc3ccc(C(=O)Nc4ccc5c(c4)CN(C4CCC(=O)NC4=O)C5=O)nc3)C2)n(-c2cc(Cl)ccc2C(F)(F)F)n1] | (M + H)⁺ = 1096.5; ¹H NMR (500 MHz, DMSO-d₆) δ 11.00 (s, 1H), 10.77 (d, J = 3.8 Hz, 1H), 9.08 (d, J = 32.6 Hz, 1H), 8.23 (d, J = 8.2 Hz, 2H), 8.11 (d, J = 8.5 Hz, 1H), 8.08-8.01 (m, 1H), 7.97 (d, J = 9.2 Hz, 2H), 7.94-7.81 (m, 2H), 7.74 (t, J = 10.2 Hz, 2H), 7.33 (dd, J = 14.9, 8.9 Hz, 1H), 5.51 (dd, J = 15.3, 6.1 Hz, 1H), 5.24-5.15 (m, 1H), 5.15-4.98 (m, 2H), 4.77 (bs, 2H), 4.53-4.41 (m, 2H), 4.35 (d, J = 17.2 Hz, 1H), 4.29-4.07 (m, 2H), 3.95-3.87 (m, 1H), 3.90-3.63 (m, 4H), 3.46-3.34 (m, 3H), 2.96-2.82 (m, 1H), 2.66-2.59 (m, 1H), 2.47-2.41 (m, 1H), 2.38 (d, J = 7.0 Hz, 3H), 2.09-1.96 (m, 1H). | 0.077/0.498 |

TABLE 2

| | ELISA Gal-3 Degradation Assay in THP-1 Cells | | | |
|---|---|---|---|---|
| | Cell Lystate (IC$_{50}$) µM | | Supernatant (IC$_{50}$) µM | |
| Ex # | test 1 | test 2 | test 1 | test 2 |
| 3 | <0.01 | <0.01 | <0.01 | 0.048 |
| 4 | <0.01 | <0.01 | 0.068 | 0.096 |
| 5 | <0.01 | <0.01 | <0.01 | <0.01 |
| 6 | <0.01 | <0.01 | 0.039 | 0.015 |
| 8 | 0.075 | 0.111 | 0.281 | 0.038 |
| 10 | 25.290 | 24.090 | 0.019 | 0.019 |
| 10 | 12.650 | 11.830 | 0.041 | 0.104 |
| 11 | <0.01 | <0.01 | 0.035 | 0.027 |
| 18 | 0.017 | 0.017 | 0.013 | 0.014 |
| 20 | 0.351 | 0.311 | 0.051 | 0.042 |
| 21 | 0.052 | 0.003 | 1.039 | 0.023 |
| 22 | 21.530 | 4.022 | 3.398 | 3.342 |
| 23 | <0.01 | <0.01 | 0.019 | <0.01 |
| 25 | >30 | >30 | 1.696 | 0.522 |
| 26 | 0.017 | 0.017 | 0.009 | 0.009 |
| 27 | 0.045 | 0.086 | | 0.040 |
| 30 | 2.848 | 23.510 | 0.854 | 0.050 |
| 31 | 4.989 | 0.021 | 0.050 | 0.014 |
| 32 | 0.933 | 8.632 | 1.251 | 1.578 |
| 33 | 21.820 | >30 | >30 | >30 |
| 34 | 0.010 | 0.012 | 4.582 | 0.210 |
| 35 | 0.238 | 0.015 | 0.314 | 0.338 |

We claim:

1. A compound of Formula (I):

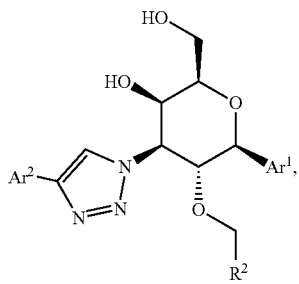

or a pharmaceutically acceptable salt thereof, wherein:
Ar$^1$ is independently

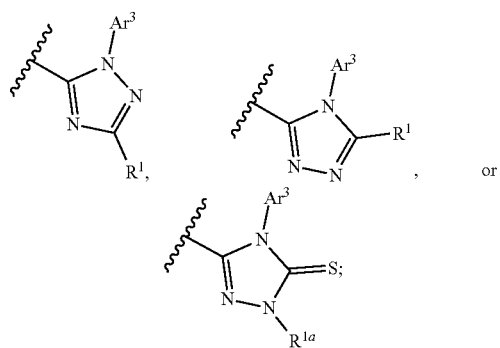

Ar$^2$ is independently phenyl or naphthyl; and wherein each ring moiety is substituted with 1 to 5 substituents selected from cyano, halogen, C$_{1-4}$ alkyl, C$_{1-4}$ alkoxy, C$_{1-4}$ haloalkyl, and C$_{1-4}$ haloalkoxy;

Ar$^3$ is independently phenyl, pyridinyl, quinolone, isoquinoline, or benzothaizolyl, wherein each ring moiety is substituted with 0 to 3 substituents selected from cyano, halogen, C$_{1-4}$ alkyl, C$_{1-4}$ haloalkyl;

R$^1$ and R$^{1a}$ are independently H or C$_{1-4}$ alkyl;

R$^2$ is independently —C(=O)NR$^3$R$^4$ or —OR$^4$;

R$^3$ is independently H, C$_{1-4}$ alkyl, or C$_{1-4}$ haloalkyl;

R$^4$ is independently -(L$^1$)$_{1-4}$-L$^2$-C(=O)NHR$^5$, -(L$^1$)$_{1-4}$-L$^2$-NHC(=O)R$^5$, (L$^1$)$_{1-4}$-NHC(=O)-L$^2$-OR$^5$,

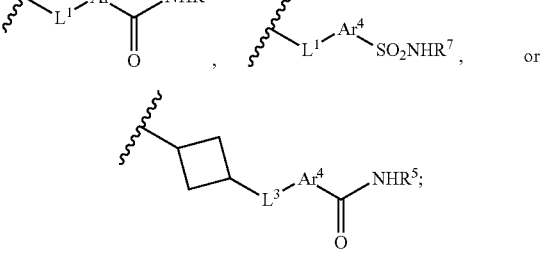

althernatively, —NR$^3$R$^4$ is independently

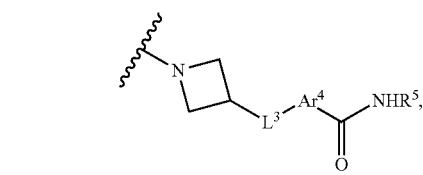

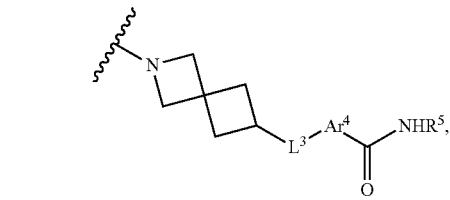

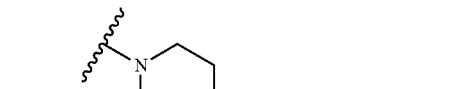

L$^1$ is independently C$_{1-3}$ alkylene or —C$_{1-3}$ alkylene-O—;
L$^2$ is independently a bond or C$_{1-3}$ alkylene;
L$^3$ is independently —O—, —CH$_2$—, —CH$_2$O—, —OCH$_2$—, or —CH$_2$OCH$_2$—;
Ar$^4$ is independently phenylene or pyridinylene; and wherein each ring moiety is substituted with 0 to 2 substituents selected from cyano, halogen, C$_{1-4}$ alkyl, C$_{1-4}$ haloalkyl, C$_{1-4}$ alkoxy, and C$_{1-4}$ haloalkoxy;

$R^5$ is independently

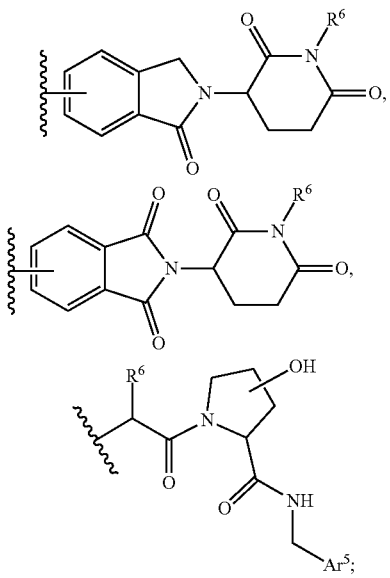

$R^6$ is independently H or $C_{1-4}$ alkyl;

$R^7$ is independently indolyl substituted with 0 to 2 substituents selected from cyano, halogen, $C_{1-4}$ alkyl, $C_{1-4}$ haloalkyl, $C_{1-4}$ alkoxy, and $C_{1-4}$ haloalkoxy; and $Ar^5$ is independently phenylene or pyridinylene; and wherein each ring moiety is substituted with a thiazolyl substituted with 0 to 2 substituents selected from cyano, halogen, $C_{1-4}$ alkyl, $C_{1-4}$ haloalkyl, $C_{1-4}$ alkoxy, and $C_{1-4}$ haloalkoxy.

2. A compound of claim 1, wherein:

$Ar^1$ is

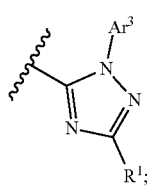

$Ar^2$ is independently phenyl substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy; and $Ar^3$ is independently phenyl substituted with 0 to 3 substituents selected from cyano, halogen, $C_{1-4}$ alkyl, $C_{1-4}$ haloalkyl, $C_{1-4}$ alkoxy, $C_{1-4}$ haloalkoxy and $C_{3-6}$ cycloalkyl.

3. A compound of claim 2, wherein:

$Ar^2$ is independently phenyl substituted with 1 to 4 substituents selected from F, Cl and Br;

$Ar^3$ is independently phenyl substituted with 0 to 3 substituents selected from Cl, $CH_3$, $CF_3$, and $-OCF_3$;

$R^3$ is independently H, $C_{1-3}$ alkyl, or $C_{1-3}$ haloalkyl;

$R^4$ is independently $-L^1-L^2-C(=O)NHR^5$, $-(L^1)_{1-3}-L^2-NHC(=O)R^5$, $(L^1)_{1-3}-NHC(=O)-L^2-OR^5$,

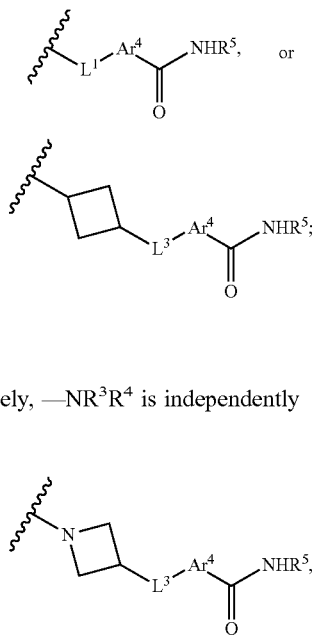

and althernatively, $-NR^3R^4$ is independently

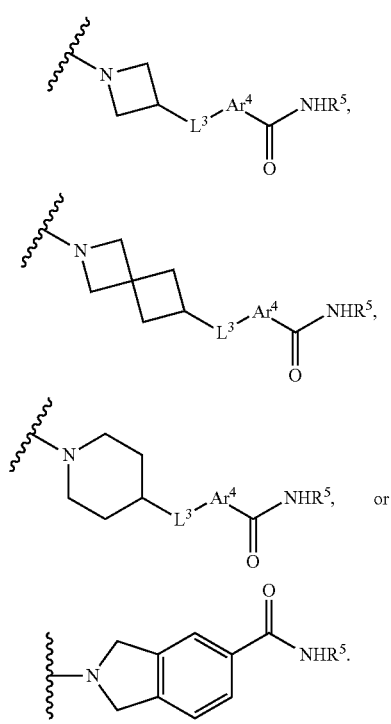

4. A compound of claim 3, wherein:

$Ar^2$ is independently

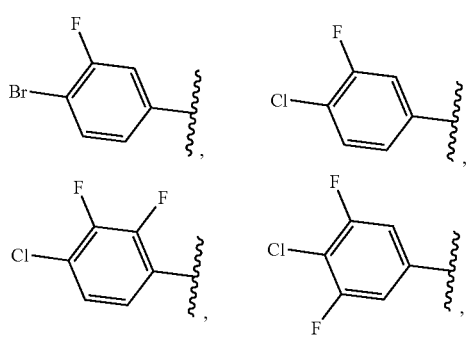

-continued
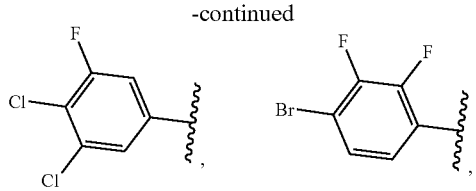
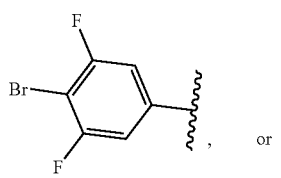
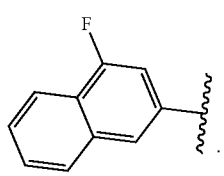
5. A compound of claim 4, wherein:
Ar³ is independently
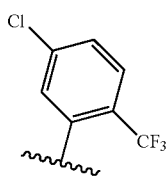
6. A compound of claim 1, wherein the compound is of Formula (Ia):
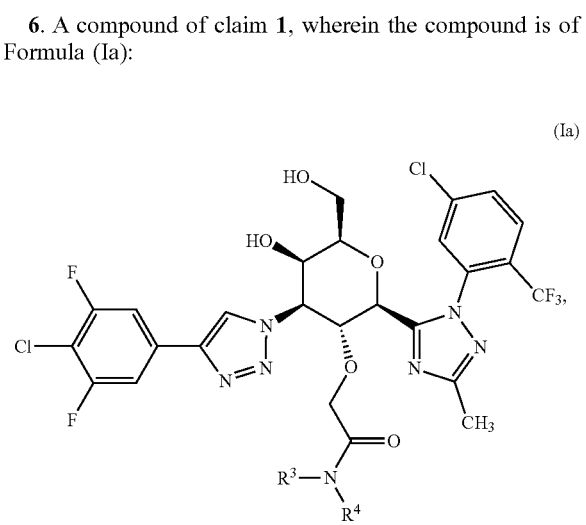
or a pharmaceutically acceptable salt thereof, wherein:
R³ is independently H or —CH₂Cl;
R⁴ is independently —CH₂CH₂OCH₂C(=O)NHR⁵, —(CH₂CH₂O)₁₋₃ (CH₂)₁₋₂NHC(=O)R⁵, —(CH₂CH₂O)₁₋₃(CH₂)₂NHC(=O)CH₂OR⁵,
althernatively, —NR³R⁴ is independently -continued
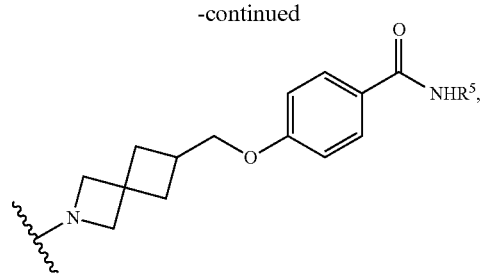
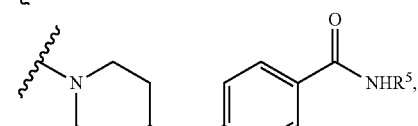
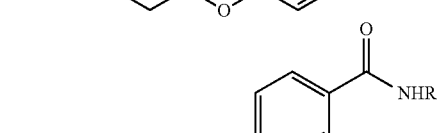
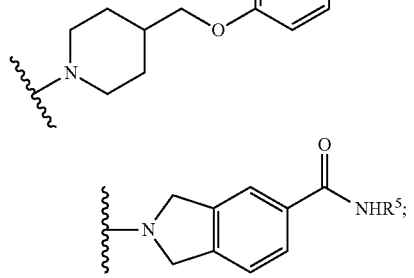
$R^5$ is independently
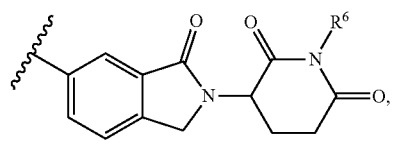
-continued
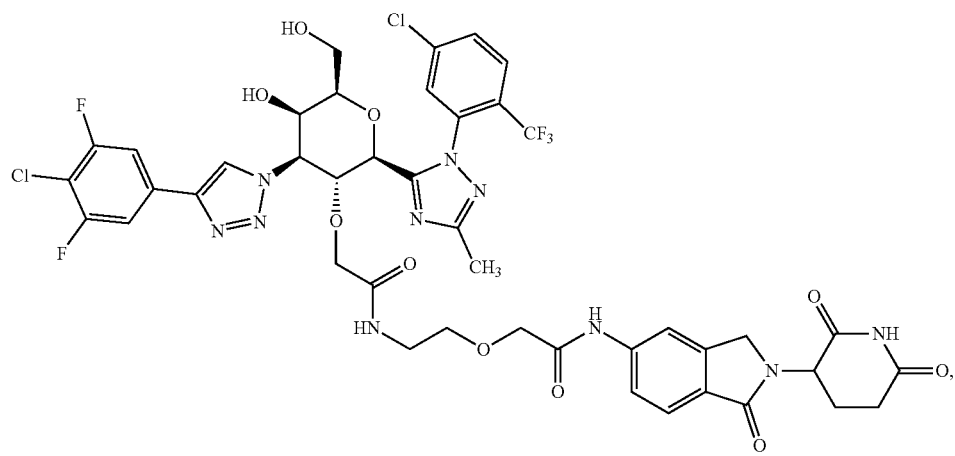
and
$R^6$ is independently H or $CH_3$.
7. A compound of claim 1, wherein the compound is selected from:

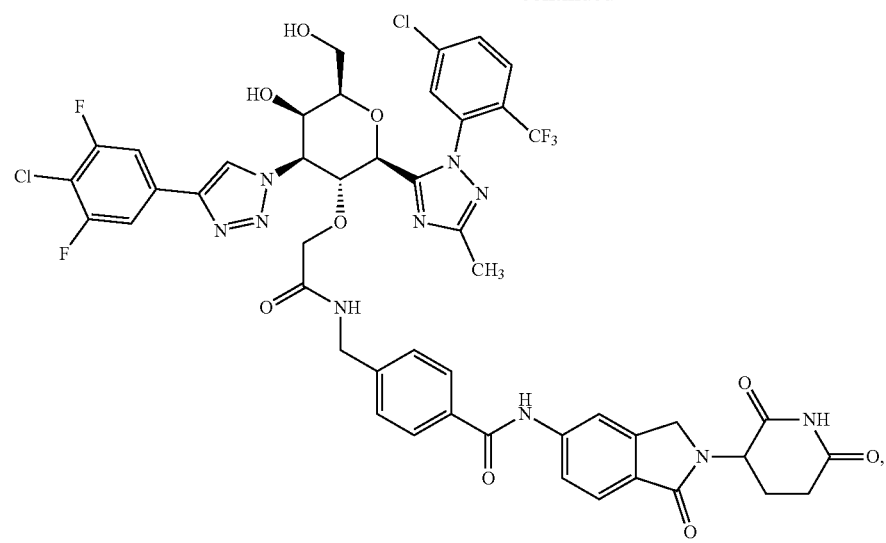
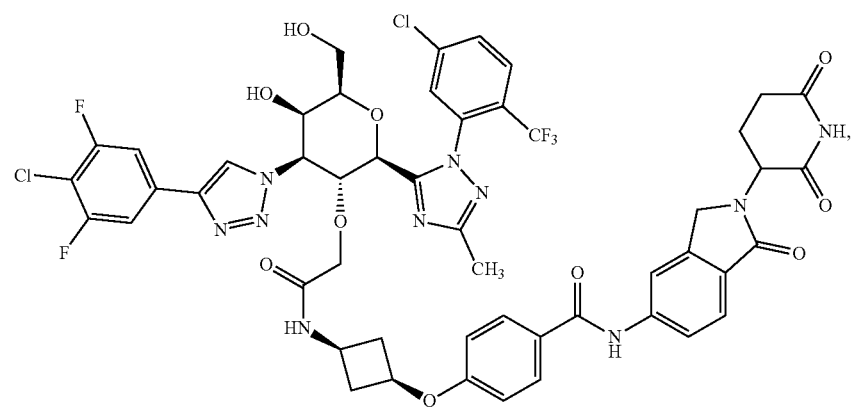
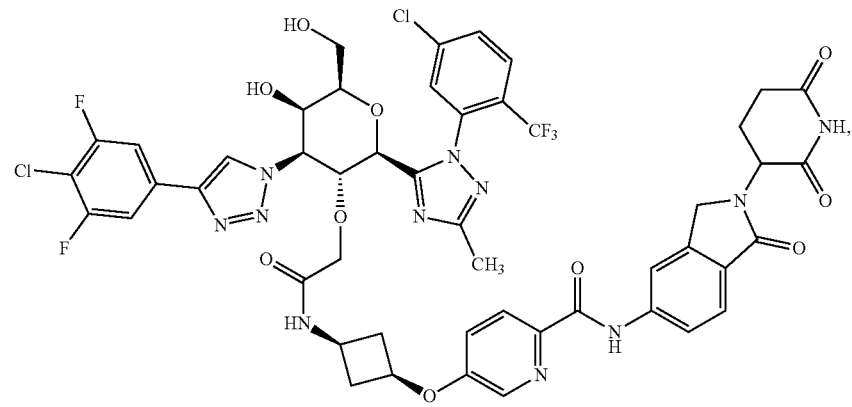

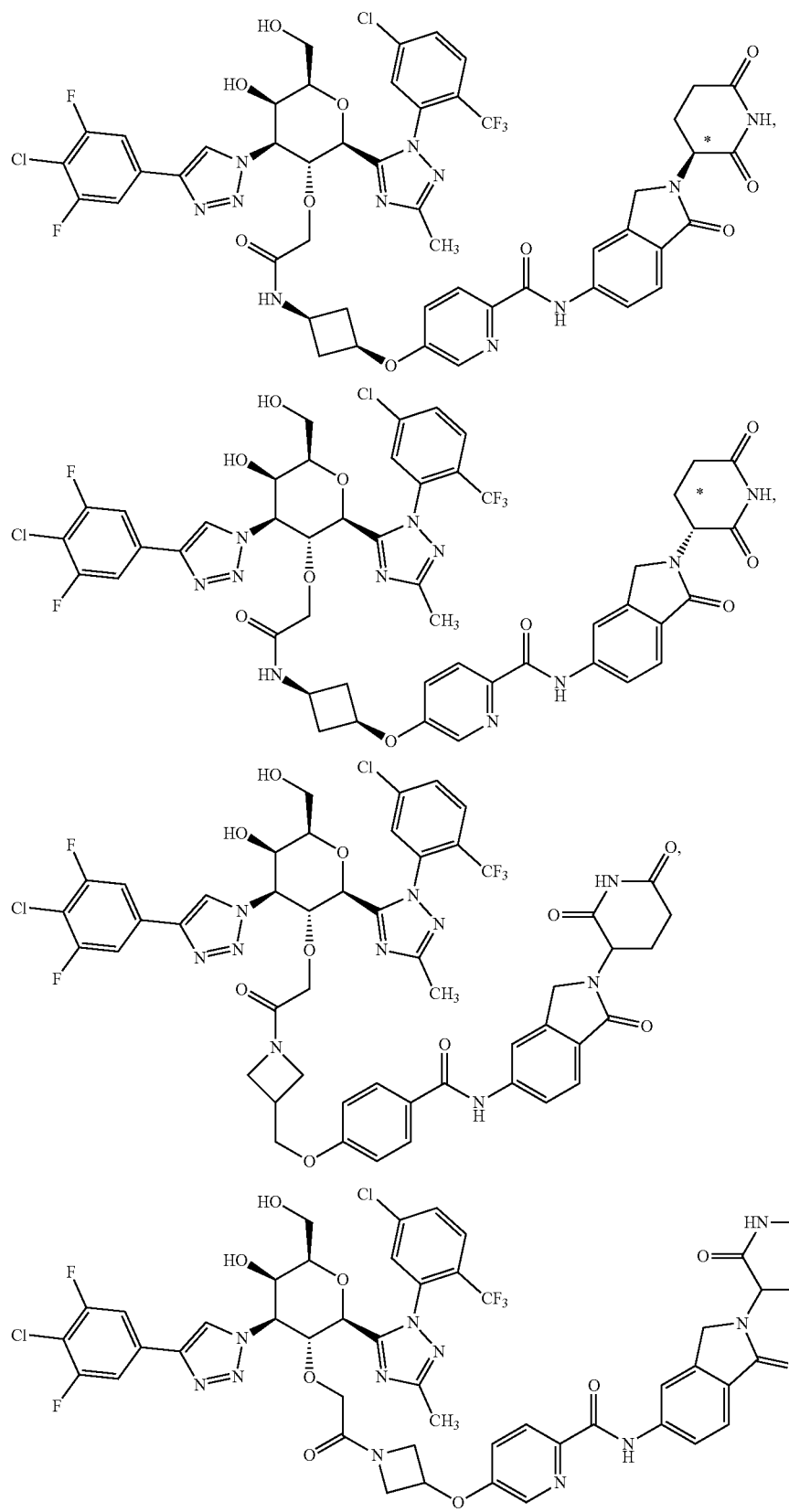

-continued
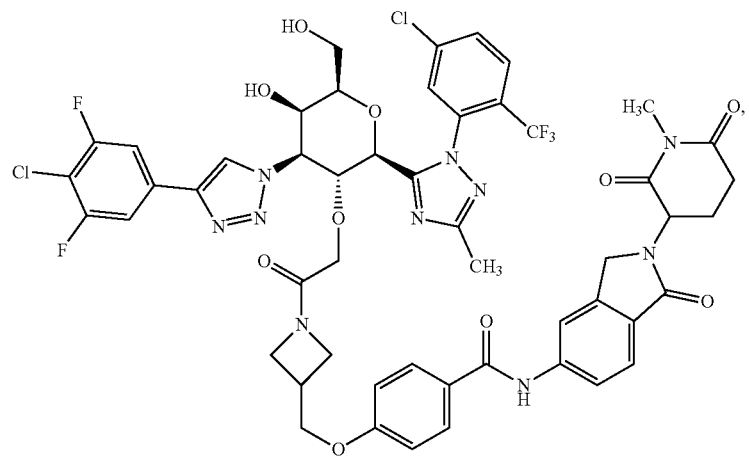
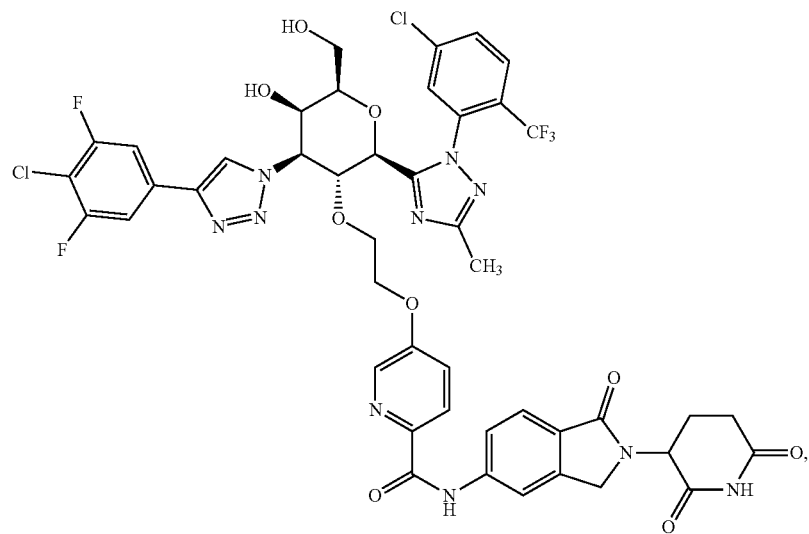
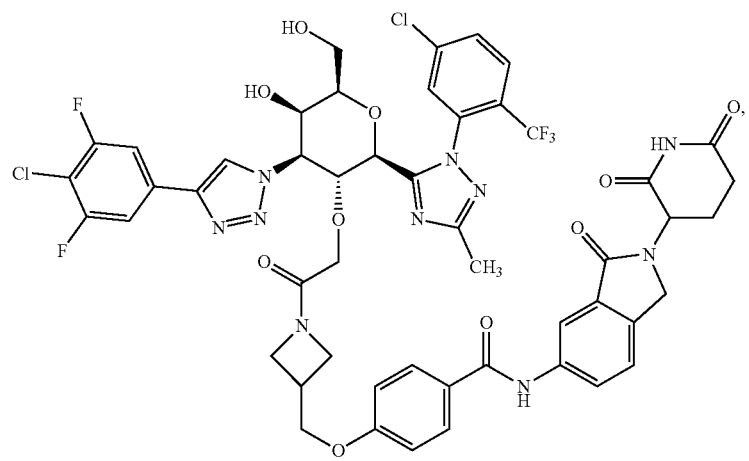

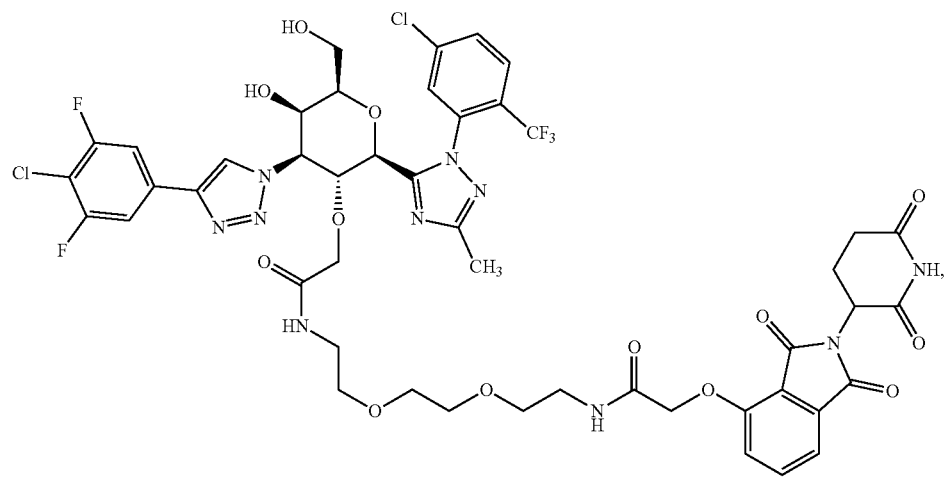
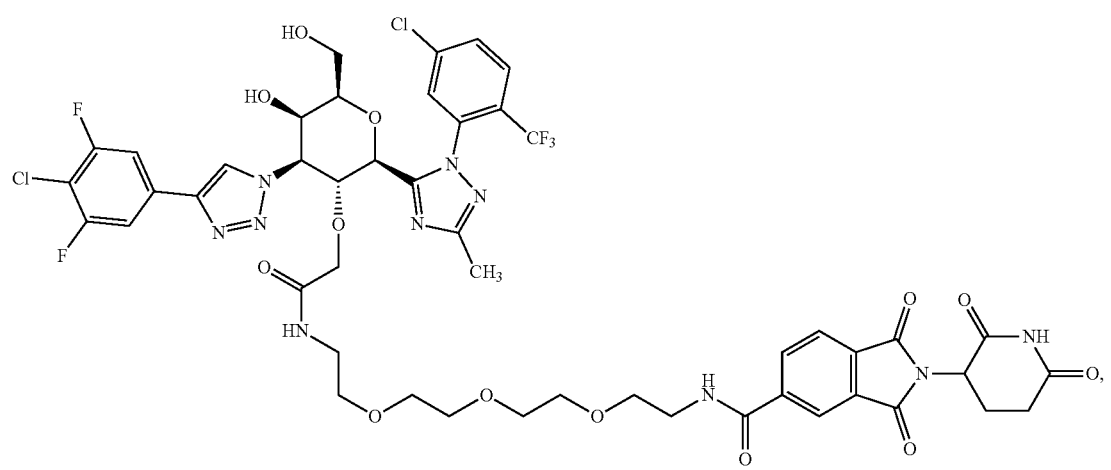
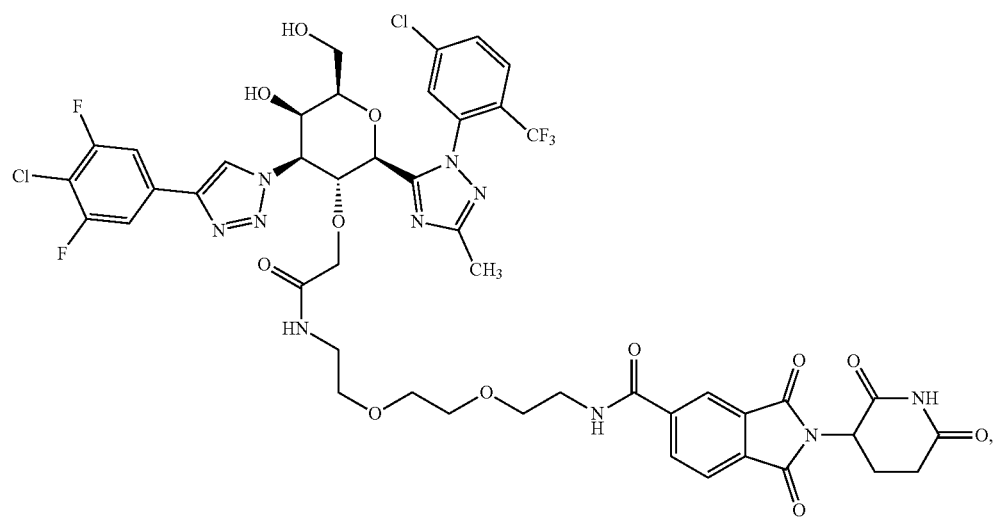

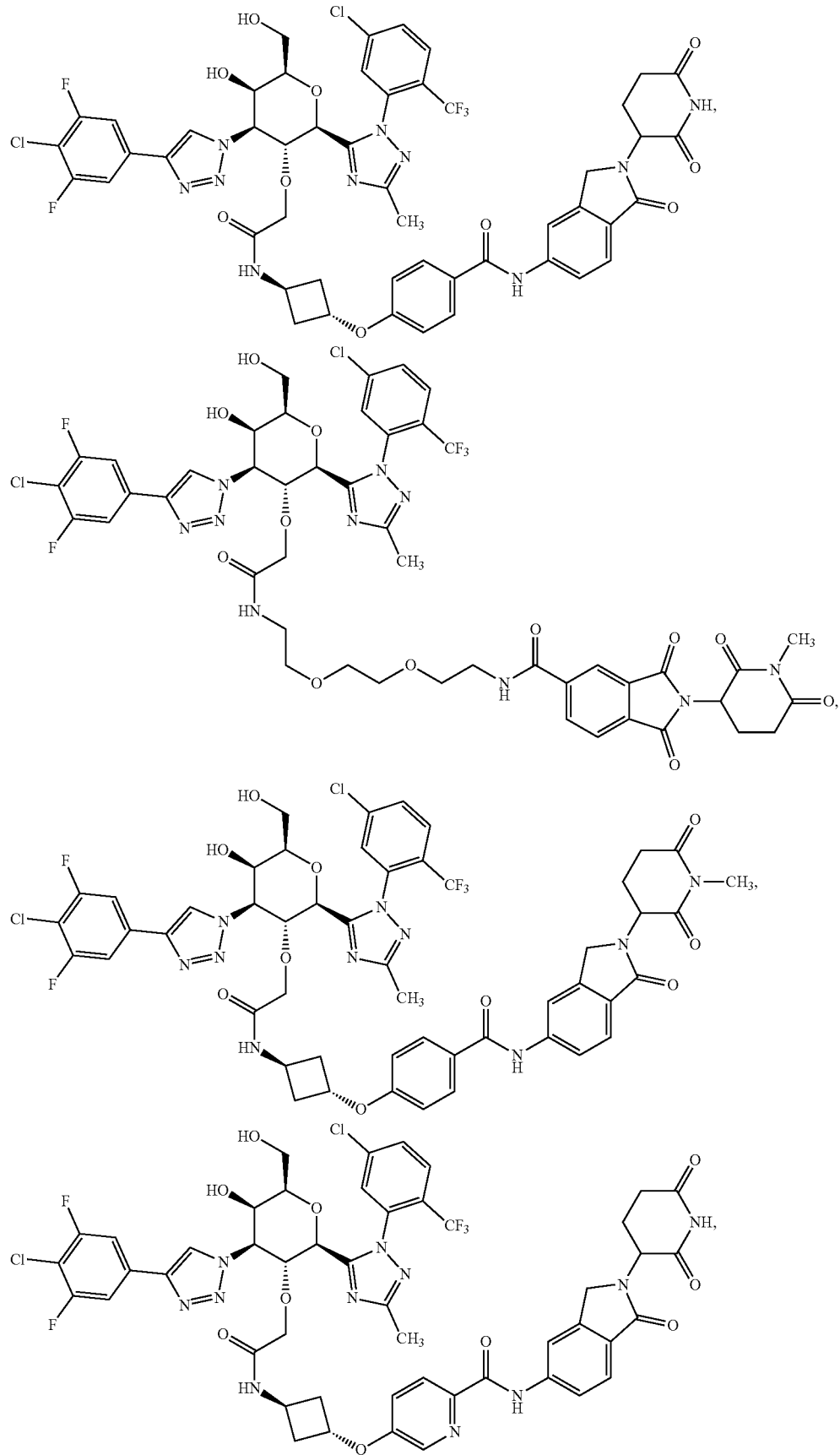

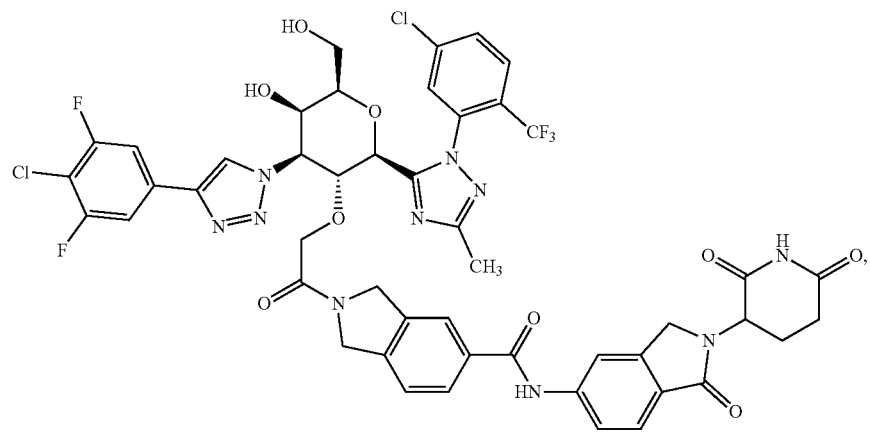
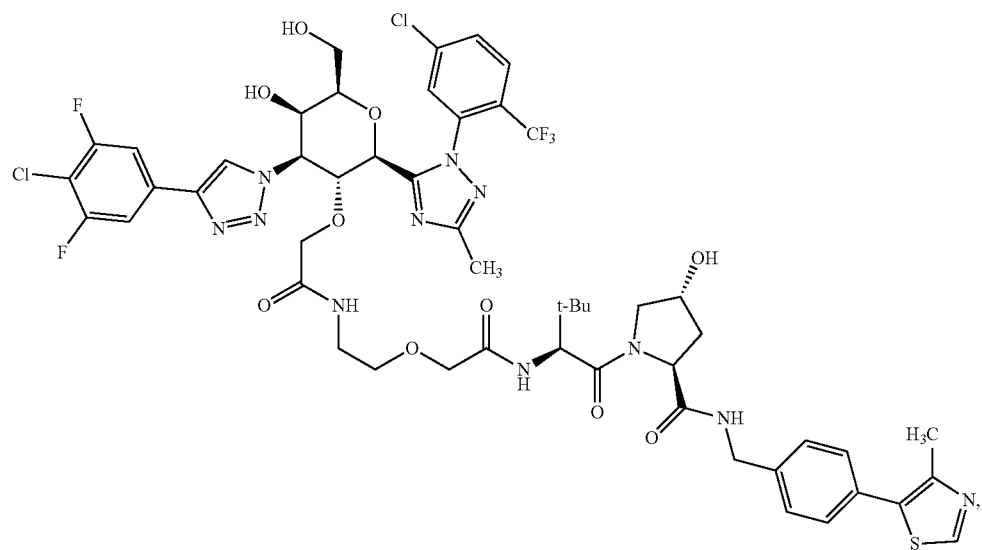
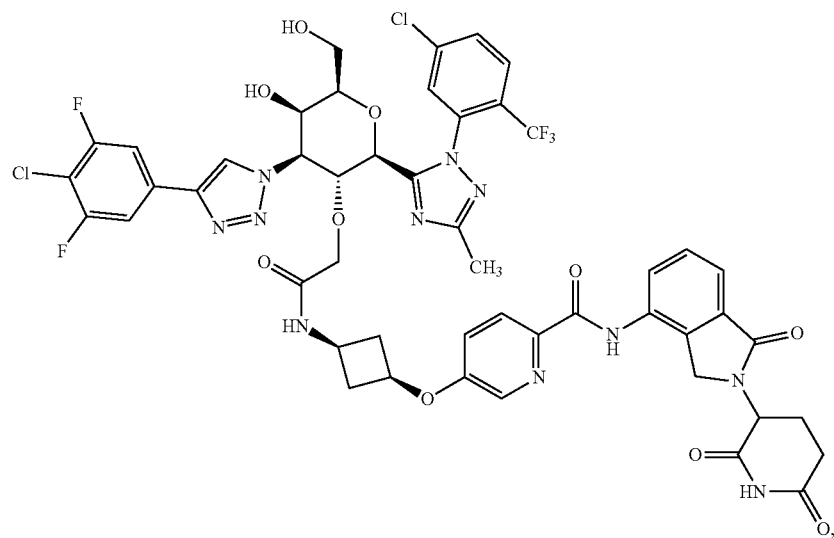

-continued
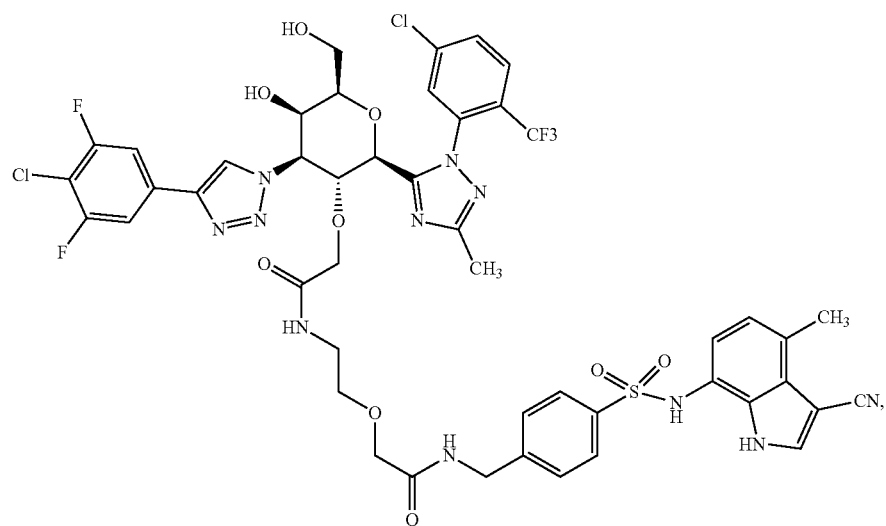
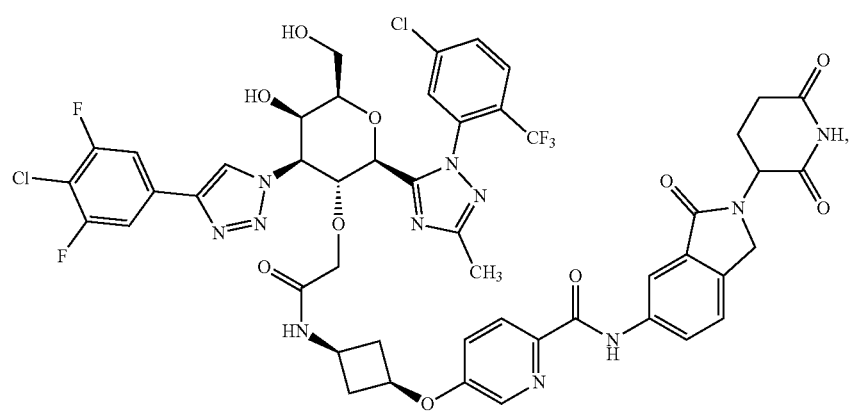
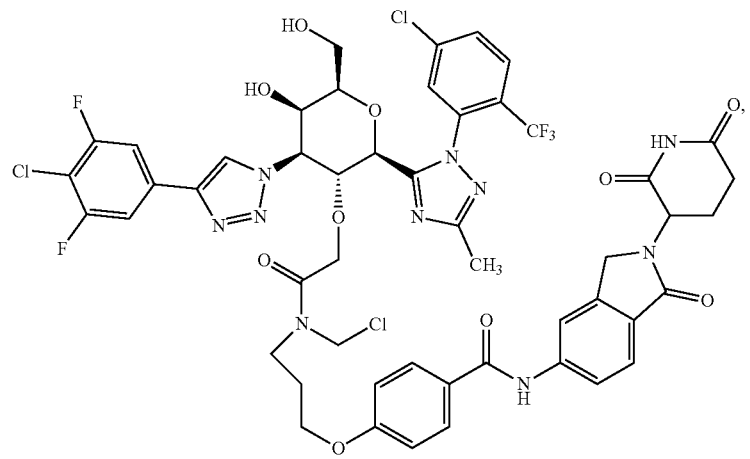

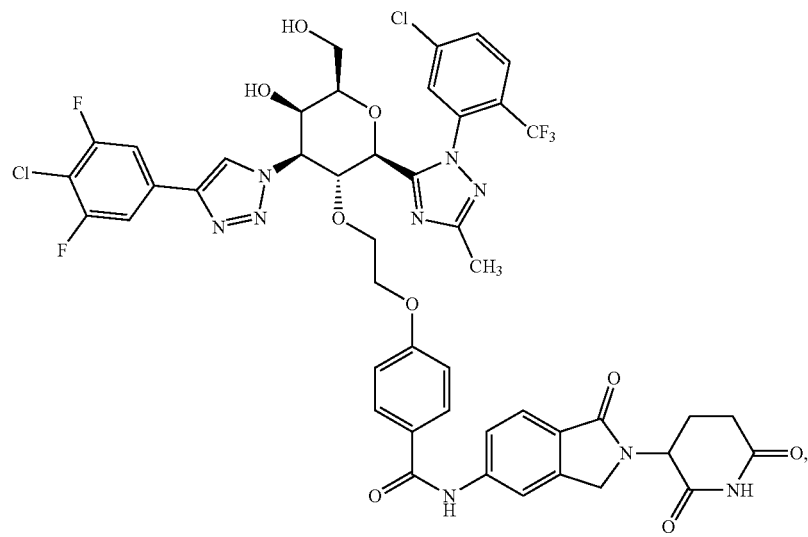
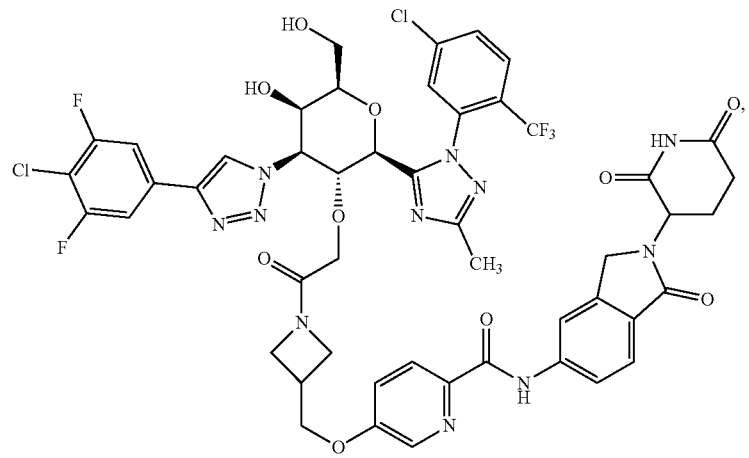
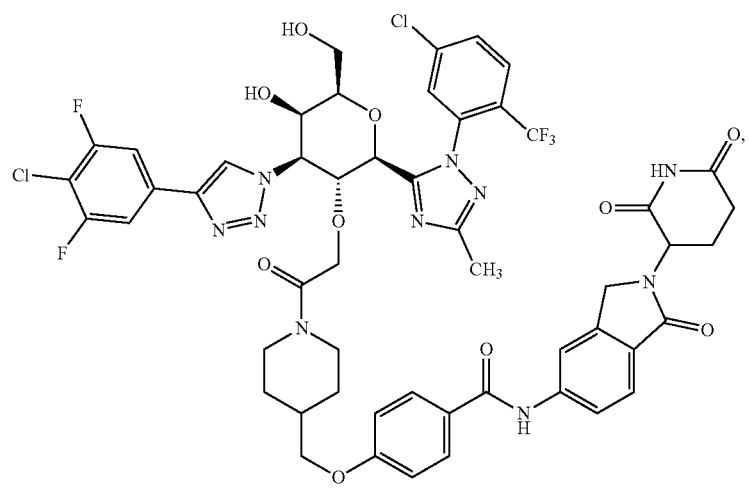

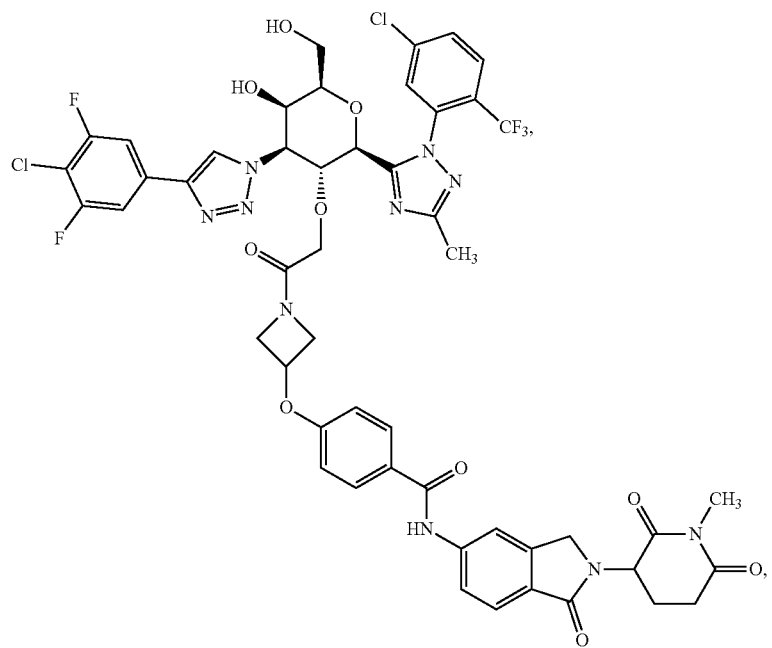
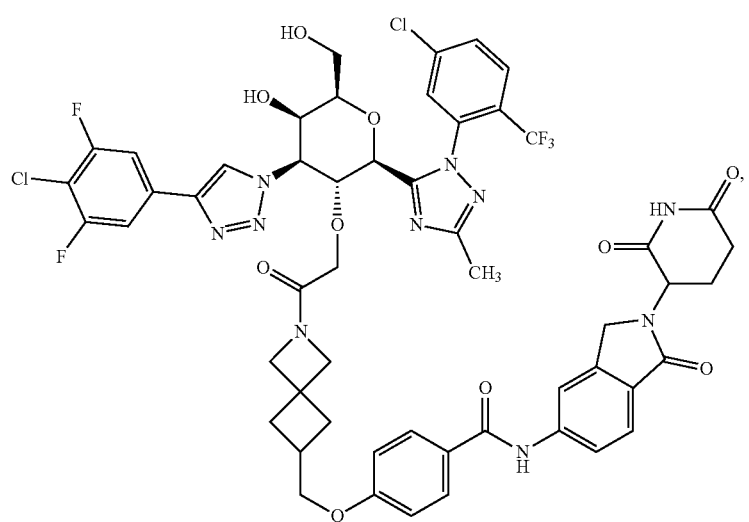

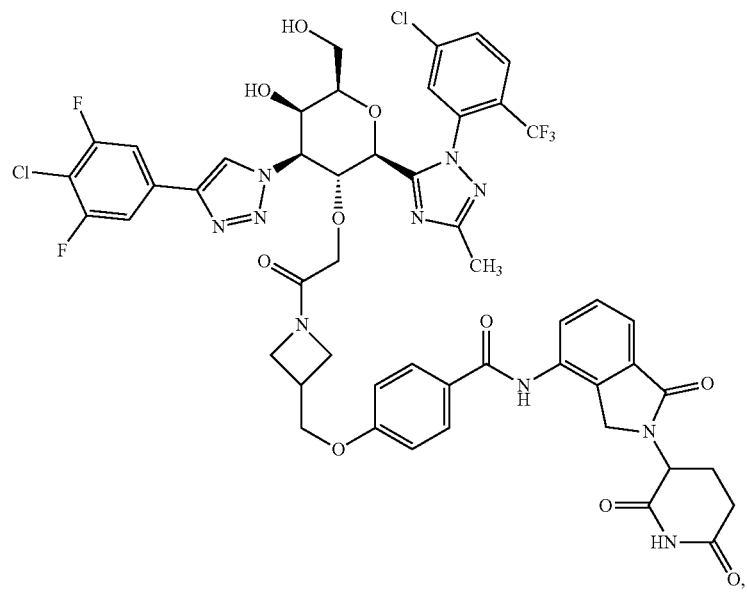
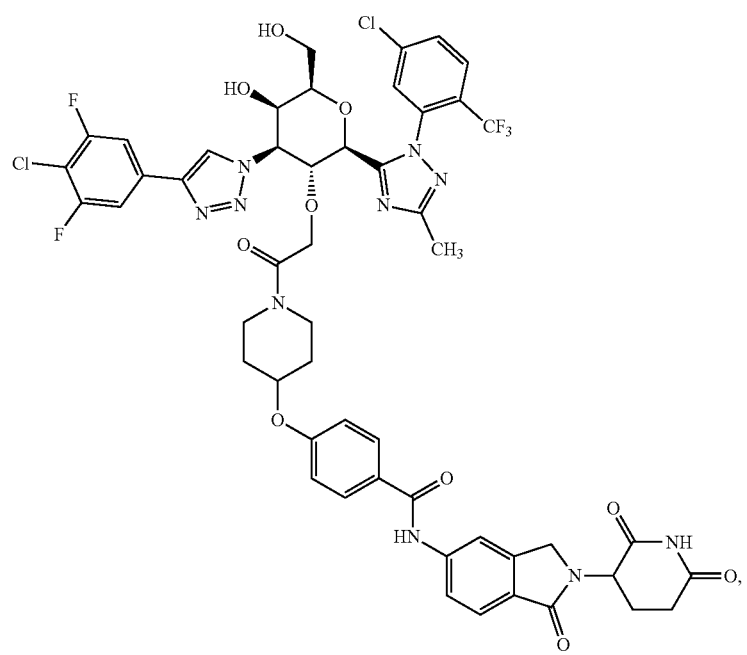

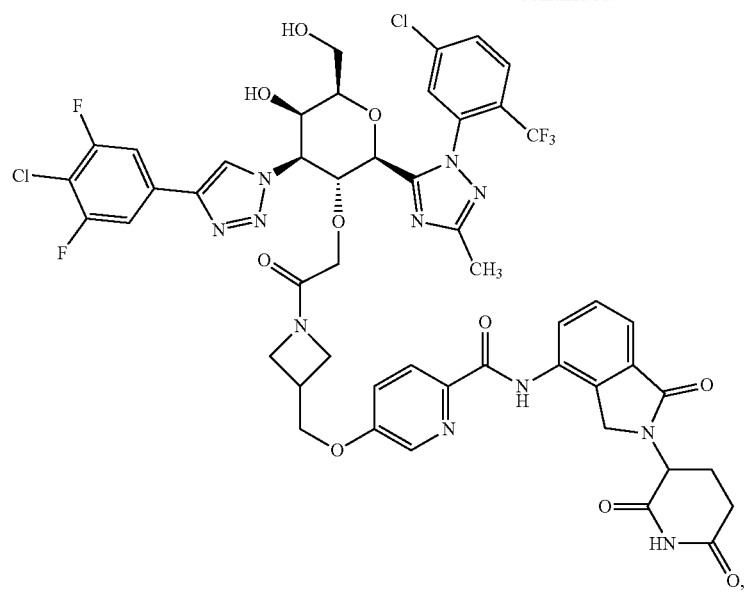
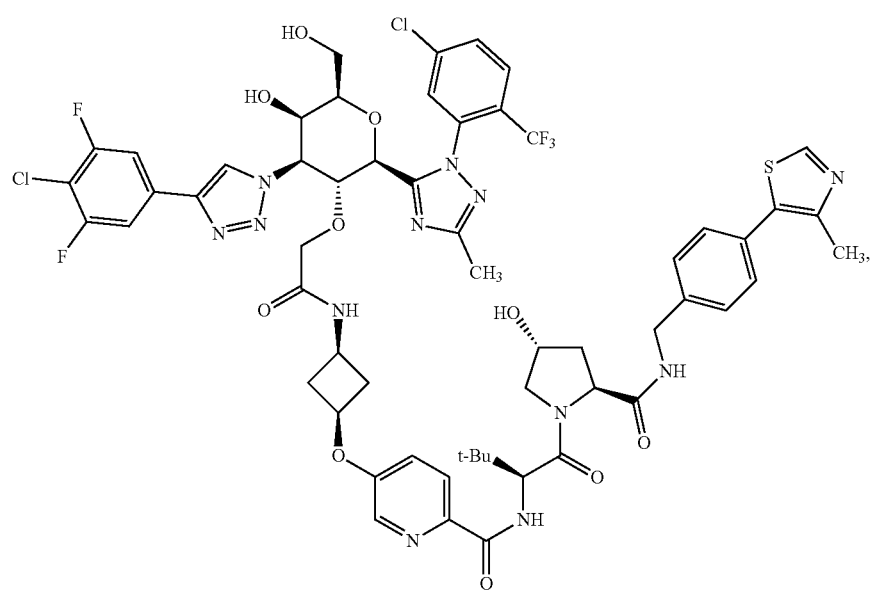
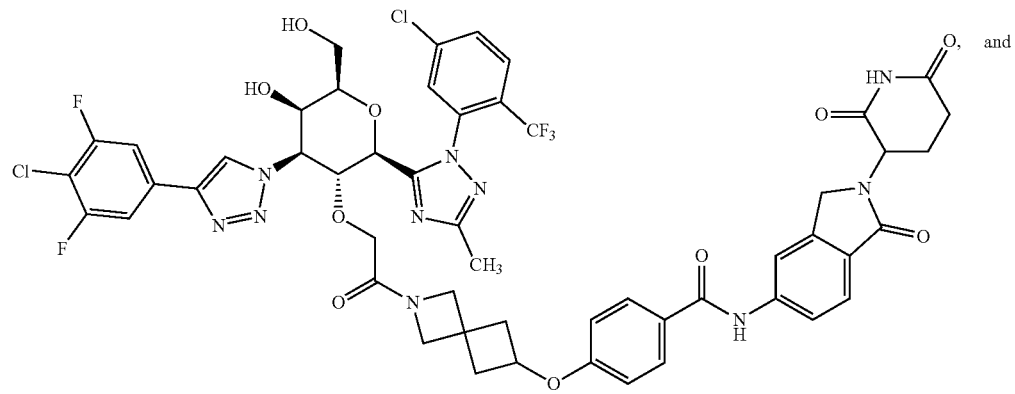

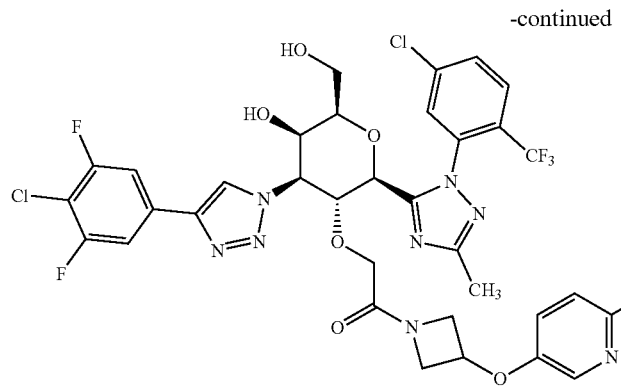
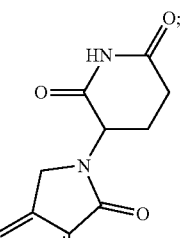

or a pharmaceutically acceptable salt thereof.

8. A composition comprising a therapeutically effective amount of a compound or a pharmaceutically acceptable salt thereof of claim 1, and one or more pharmaceutically acceptable carriers.

9. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 1, or a pharmaceutically acceptable salt thereof of to a patient.

10. A method for treating a disease or condition selected from renal fibrosis, pulmonary fibrosis, hepatic fibrosis, arterial fibrosis, and systemic sclerosis; comprising administering a therapeutically effective amount of a compound of claim 1, or a pharmaceutically acceptable salt thereof of to a patient.

11. A composition comprising a therapeutically effective amount of a compound or a pharmaceutically acceptable salt thereof of claim 6, and one or more pharmaceutically acceptable carriers.

12. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 6, or a pharmaceutically acceptable salt thereof of to a patient.

13. A method for treating a disease or condition is selected from renal fibrosis, pulmonary fibrosis, hepatic fibrosis, arterial fibrosis, and systemic sclerosis; comprising administering a therapeutically effective amount of a compound of claim 6, or a pharmaceutically acceptable salt thereof of to a patient.

14. A composition comprising a therapeutically effective amount of a compound or a pharmaceutically acceptable salt thereof of claim 7, and one or more pharmaceutically acceptable carriers.

15. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder; cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 7, or a pharmaceutically acceptable salt thereof of to a patient.

16. A method for treating a disease or condition is selected from renal fibrosis, pulmonary fibrosis, hepatic fibrosis, arterial fibrosis, and systemic sclerosis; comprising administering a therapeutically effective amount of a compound of claim 7, or a pharmaceutically acceptable salt thereof of to a patient.

* * * * *